US012629517B2

(12) United States Patent
Forsell

(10) Patent No.: US 12,629,517 B2
(45) Date of Patent: *May 19, 2026

(54) METHOD FOR CONTROLLING FLOW OF SPERMS IN A UTERINE TUBE

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 361 days.

This patent is subject to a terminal disclaimer.

(21) Appl. No.: 18/207,705

(22) Filed: Jun. 9, 2023

(65) Prior Publication Data

US 2024/0009454 A1 Jan. 11, 2024

Related U.S. Application Data

(63) Continuation of application No. 16/266,130, filed on Feb. 4, 2019, now Pat. No. 11,672,977, which is a
(Continued)

(51) Int. Cl.
| | |
|---|---|
| *A61F 6/20* | (2006.01) |
| *A61B 17/12* | (2006.01) |
| *A61B 17/135* | (2006.01) |
| *A61M 60/148* | (2021.01) |
| *A61N 1/05* | (2006.01) |
| *A61N 1/36* | (2006.01) |
(Continued)

(52) U.S. Cl.
CPC .... *A61N 1/36007* (2013.01); *A61B 17/12009* (2013.01); *A61B 17/1355* (2013.01); *A61F 6/20* (2013.01); *A61F 6/202* (2013.01); *A61M 60/148* (2021.01); *A61N 1/0521* (2013.01); *A61B 2017/00163* (2013.01); *A61B 2017/00212* (2013.01); *A61B 2017/00221*

(2013.01); *A61B 2017/00411* (2013.01); *A61B 2017/00991* (2013.01); *A61F 2/0009* (2013.01); *A61F 2/0031* (2013.01); *A61F 6/00* (2013.01); *A61F 6/06* (2013.01); *A61F 6/14* (2013.01); *A61F 6/204* (2013.01); *A61F 6/206* (2013.01); *A61F 6/22* (2013.01); *A61N 1/403* (2013.01)

(58) Field of Classification Search
CPC ...... A61F 6/00; A61F 6/06; A61F 6/20; A61F 6/202; A61F 6/204; A61F 6/206; A61F 6/208; A61B 2017/00212; A61B 2017/00411; A61B 17/12009; A61N 1/0521; A61N 1/36007
See application file for complete search history.

(56) References Cited

U.S. PATENT DOCUMENTS 9,949,871 B2 * 4/2018 Forsell ..................... A61F 6/20

* cited by examiner

*Primary Examiner* — Keri J Nelson

(57) ABSTRACT

An apparatus for controlling a flow of sperms in a uterine tube formed by a uterine tube wall of a patient's uterine tube comprises an implantable constriction device for gently constricting (i.e. without substantially hampering the blood circulation in the uterine tube wall) at least one portion of the uterine tube wall to influence the flow in the uterine tube, and a stimulation device for stimulating the wall portion of the uterine tube wall. A control device controls the stimulation device to stimulate the wall portion, as the constriction device constricts the wall portion, to cause contraction of the wall portion constricted by the constriction device to further influence the flow in the uterine tube. The apparatus can be used for restricting or stopping the flow in the uterine tube, or for actively moving the fluid in the uterine tube, with a low risk of injuring the uterine tube.

20 Claims, 38 Drawing Sheets

Related U.S. Application Data continuation of application No. 12/285,808, filed on Oct. 14, 2008, now Pat. No. 10,195,325.

(60) Provisional application No. 60/960,716, filed on Oct. 11, 2007.

(51) Int. Cl.

| | |
|---|---|
| *A61B 17/00* | (2006.01) |
| *A61F 2/00* | (2006.01) |
| *A61F 6/00* | (2006.01) |
| *A61F 6/06* | (2006.01) |
| *A61F 6/14* | (2006.01) |
| *A61F 6/22* | (2006.01) |
| *A61N 1/40* | (2006.01) |

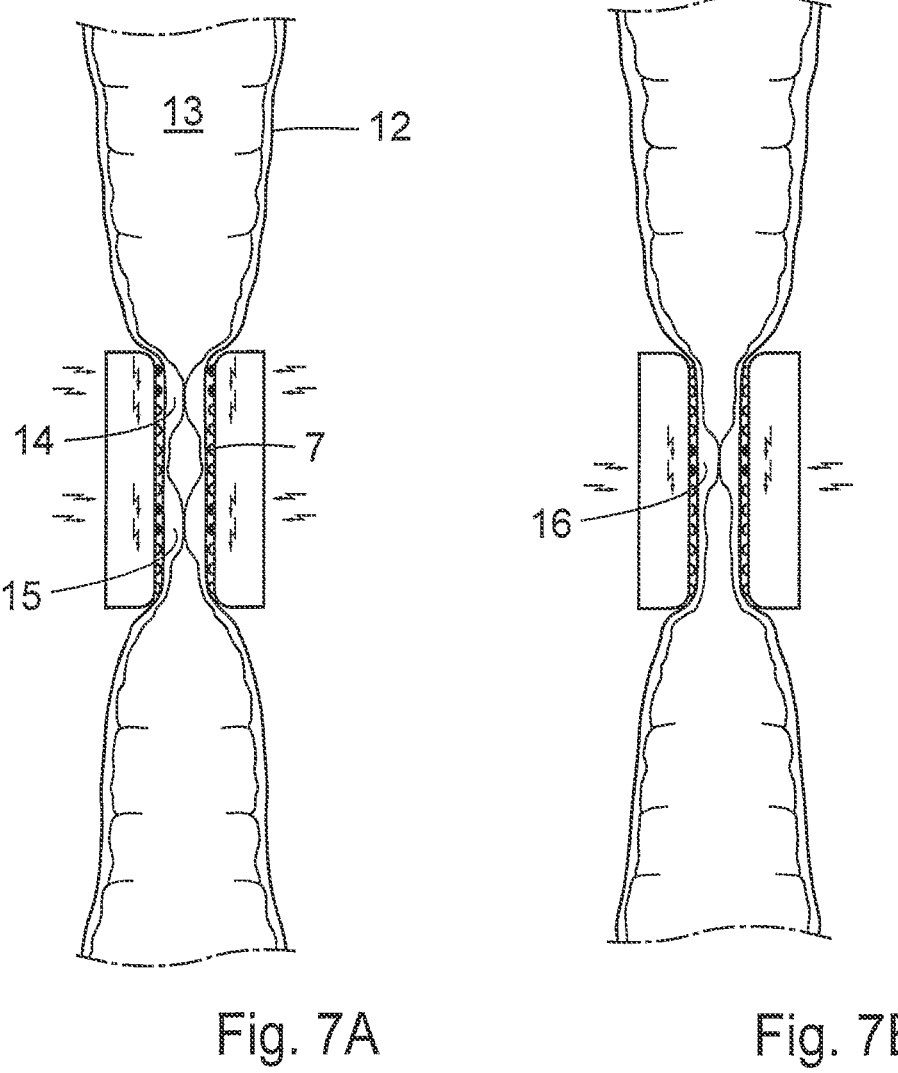
Fig. 7A                    Fig. 7B

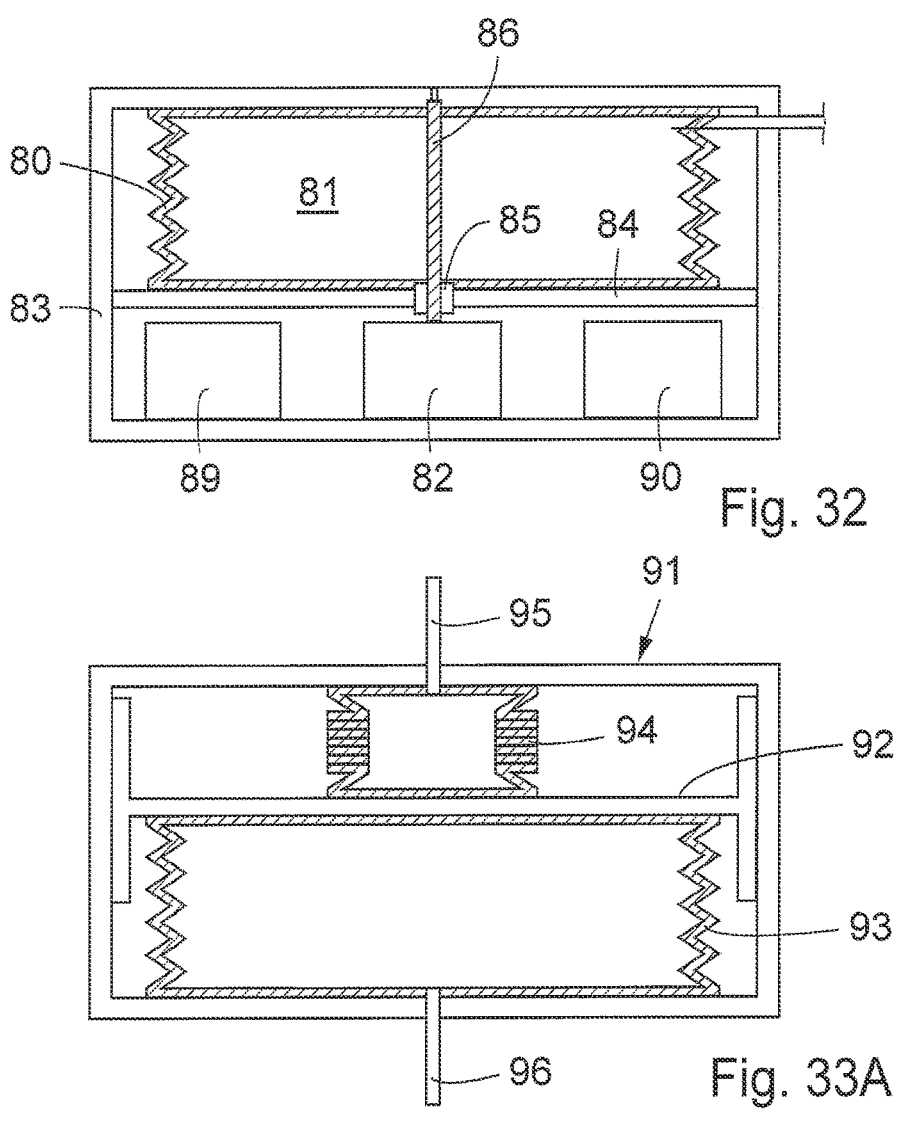
Fig. 32
Fig. 33A
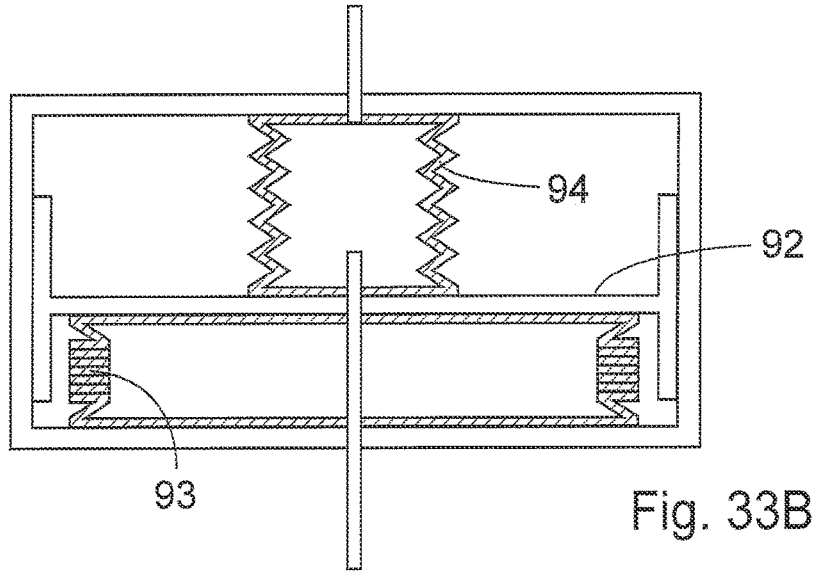
Fig. 33B

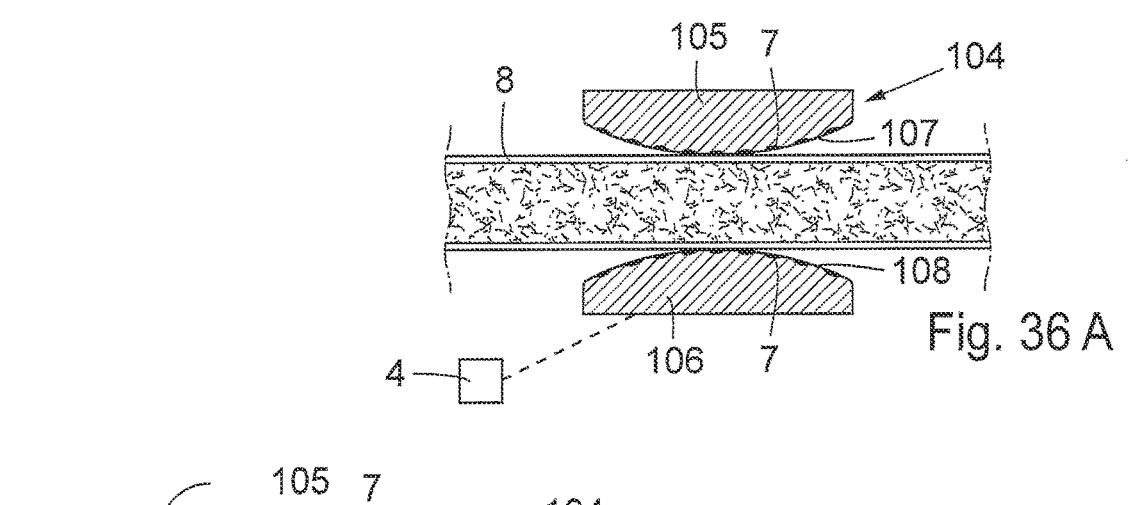
Fig. 36 A
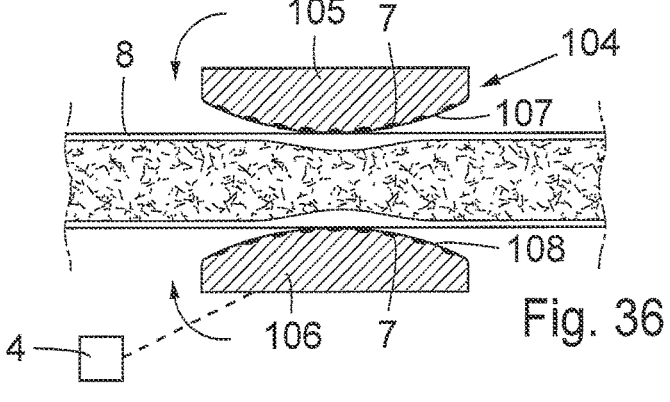
Fig. 36 B
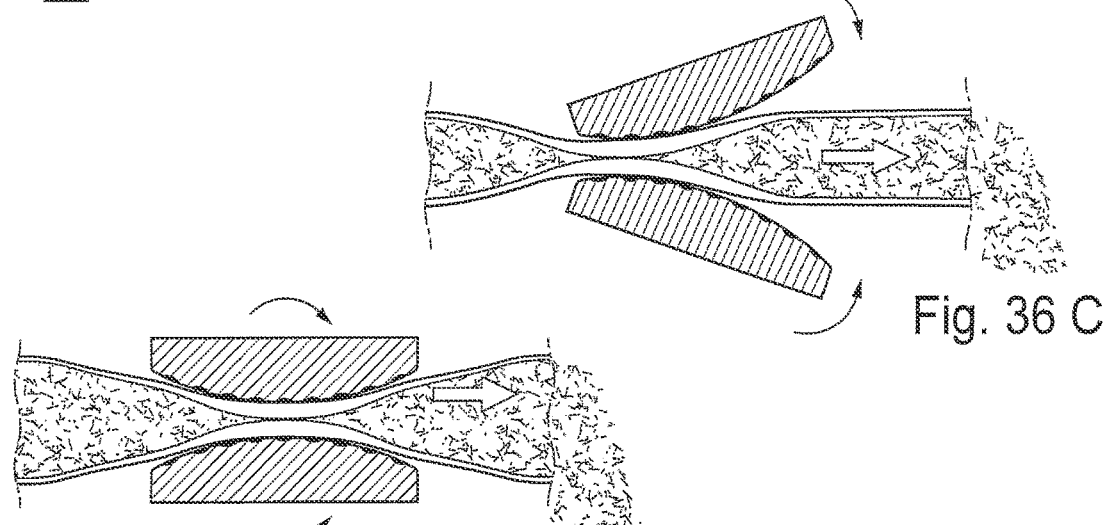
Fig. 36 C
Fig. 36 D
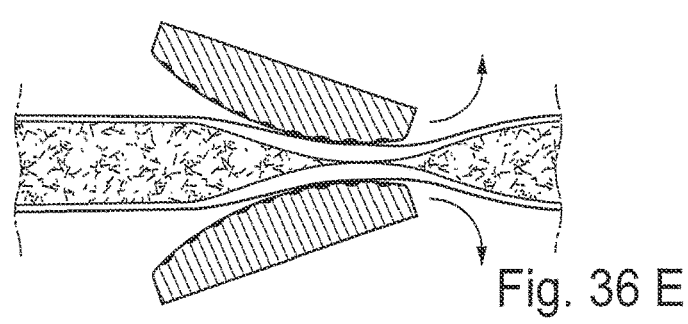
Fig. 36 E

2

2a  2b  2c  2d  2e  2f  2g  2h  2i  2j  2k  2l  2m  2n

1000

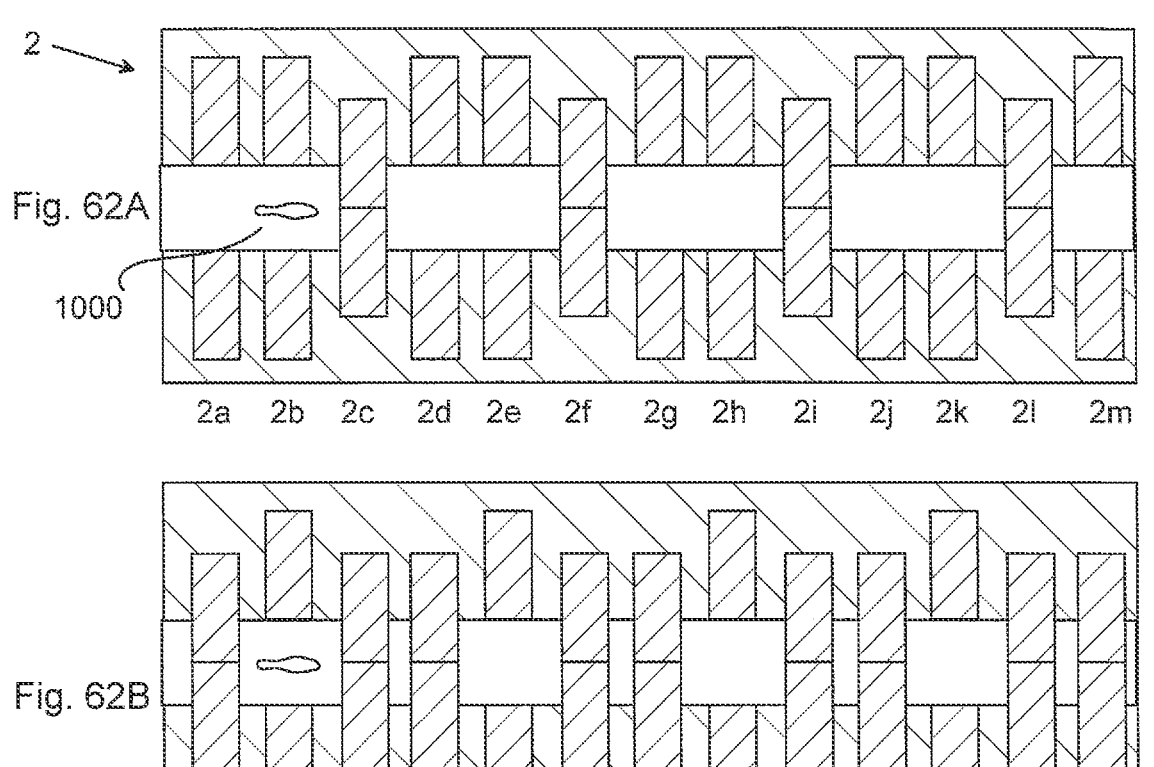
Fig. 62A
2
1000
2a  2b  2c  2d  2e  2f  2g  2h  2i  2j  2k  2l  2m
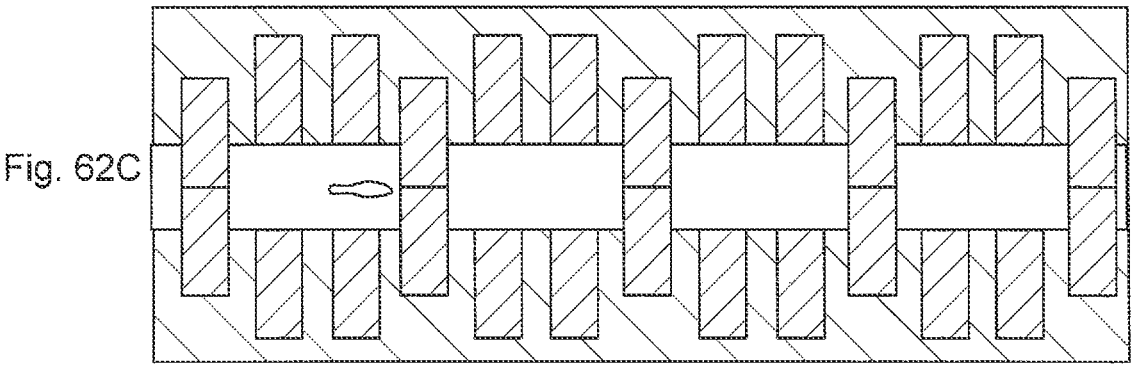
Fig. 62B
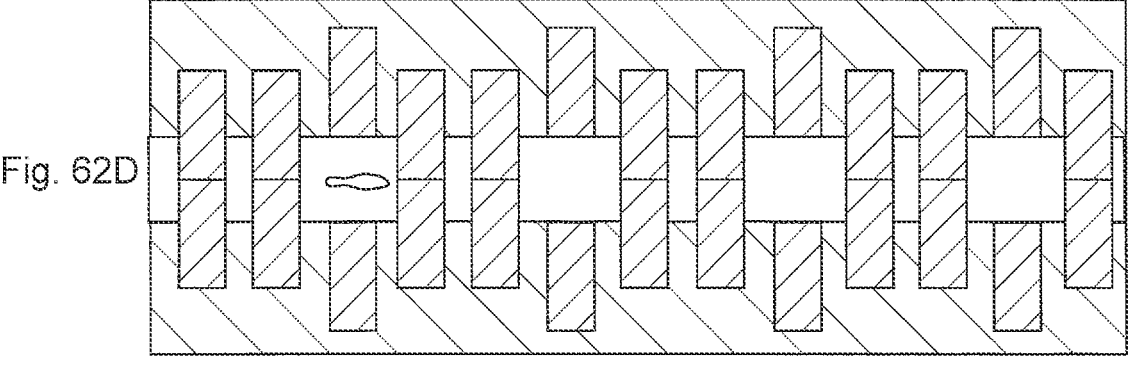
Fig. 62C
Fig. 62D

METHOD FOR CONTROLLING FLOW OF SPERMS IN A UTERINE TUBE

This application is a continuation of U.S. application Ser. No. 16/266,130, filed 4 Feb. 2019, which is a continuation of U.S. application Ser. No. 12/285,808, filed 14 Oct. 2008, which claims priority from Provisional Application 60/960, 716 filed 11 Oct. 2007. The entire contents of the above applications are hereby incorporated by reference in the application.

FIELD OF THE INVENTION

The present invention relates to controlling the flow of fluids and/or other bodily matter in bodily organs, and in particular, to an apparatus for controlling the flow of sperms in the uterine tubes of a female patient.

BACKGROUND OF THE INVENTION

The invention adapted to affect the transportation of sperm in the uterine tube may help women to avoid pregnancy by preventing the sperm to reach the egg by preventing the sperm to reach the egg for a predetermined amount of time, thus affect the flow of the sperm. The lifetime of a sperm is normally 3-5 days. Furthermore the transportation of egg takes so long time in the uterine tube that any egg reaching the proximal part of the uterine tube is most likely not viable any more.

Conceptive drugs may cause blood clots and other serious complications. A safer more permanent but still adjustable device has an important role to fill.

SUMMARY OF THE INVENTION

The object of the present invention is to provide an apparatus for controlling the movement of sperms in the uterine tubes of a female patient.

In accordance with this object of the present invention, there is provided an apparatus for controlling a flow of sperms in an uterine tube of a female patient, the apparatus comprising: an implantable constriction device for gently constricting at least one portion of the uterine tube wall to at least partly constrict the uterine tube, a stimulation device for stimulating the wall portion of the uterine tube to further constrict and influence the uterine tube, and a control device for controlling the stimulation device to stimulate the uterine tube wall portion, as the constriction device constricts the uterine tube wall portion, to cause contraction of the uterine tube wall portion to further constrict and influence the flow of sperms in the uterine tube.

The present invention provides an advantageous combination of constriction and stimulation devices, which results in a two-stage influence on the sperms in the uterine tube. Thus, the constriction device may gently constrict the uterine tube wall by applying a relatively weak force against the wall portion, and the stimulation device may stimulate the constricted wall portion to achieve the desired final influence on the flow in the uterine tube. The phrase "gently constricting a portion of the uterine tube wall" is to be understood as constricting the wall portion without substantially hampering the blood circulation in the uterine tube wall.

However, it is possible the apparatus comprise either the constriction device or the stimulation device. Therefore all the embodiments described in this application should be understood to exists in three versions. Only stimulation device or only constriction device or the combination thereof. The term uterine tube of course relates to either one or preferable the two uterine tubes. The device may beused either to promote or prevent pregnancy, affecting the flow of sperm in two different directions, wherein preventing the sperm reaching the egg prevents pregnancy.

Preferably, the stimulation device is adapted to stimulate different areas of the wall portion as the constriction device constricts the wall portion, and the control device controls the stimulation device to intermittently and individually stimulate the areas of the wall portion. This intermittent and individual stimulation of different areas of the wall portion of the organ allows tissue of the wall portion to maintain substantially normal blood circulation during the operation of the apparatus of the invention.

In most applications using the present invention, there will be daily adjustments of the implanted constriction device. Therefore, in a preferred embodiment of the invention, the constriction device is adjustable to enable adjustment of the constriction of the wall portion as desired, wherein the control device controls the constriction device to adjust the constriction of the wall portion. The control device may control the constriction and stimulation devices independently of each other, and simultaneously. Optionally, the control device may control the stimulation device to stimulate, or to not stimulate the wall portion while the control device controls the constriction device to change the constriction of the wall portion.

Initially, the constriction device may be calibrated by using the control device to control the stimulation device to stimulate the wall portion, while controlling the constriction device to adjust the constriction of the wall portion until the desired restriction of the flow of sperms in the uterine tube is obtained.

Flow Restriction

The apparatus of the present invention is well suited for restricting the flow of sperms in the uterine tube of a female patient. Thus, in a principal embodiment of the invention, the constriction device is adapted to constrict the wall portion to at least restrict the flow in the uterine tube, and the control device controls the stimulation device to cause contraction of the constricted wall portion, so that the flow in the uterine tube is at least further restricted. Specifically, the constriction device is adapted to constrict the wall portion to a constricted state in which the blood circulation in the constricted wall portion is substantially unrestricted and the flow in the uterine tube is at least restricted, and the control device controls the stimulation device to cause contraction of the wall portion, so that the flow in the uterine tube is at least further restricted when the wall portion is kept by the constriction device in the constricted state.

The constriction and stimulation devices may be controlled to constrict and stimulate, respectively, to an extent that depends on the flow restriction that is desired to be achieved in a specific application of the apparatus of the invention. Thus, in accordance with a first flow restriction option, the control device controls the constriction device to constrict the wall portion, such that flow in the uterine tube is restricted but not stopped, and controls the stimulation device to stimulate the constricted wall portion to cause contraction thereof, such that flow of sperms in the uterine tube is further restricted but not stopped. More precisely, the control device may control the stimulation device in a first mode to stimulate the constricted wall portion to further restrict but not stop the flow in the uterine tube and to:

a) control the stimulation device in a second mode to cease the stimulation of the wall portion to increase the flow in the uterine tube; or b) control the stimulation and constriction devices in the second mode to cease the stimulation of the wall portion and release the wall portion to restore the flow in the uterine tube.

In accordance with a second flow restriction option, the control device controls the constriction device to constrict the wall portion, such that flow in the uterine tube is restricted but not stopped, and controls the stimulation device to stimulate the constricted wall portion to cause contraction thereof, such that flow in the uterine tube is stopped. More precisely, the control device may control the stimulation device in a first mode to stimulate the constricted wall portion to further restrict but not stop the flow in the uterine tube and to:

a) control the stimulation device in a second mode to cease the stimulation of the wall portion to allow flow in the uterine tube; or b) control the stimulation and constriction devices in the second mode to cease the stimulation of the wall portion and release the wall portion to restore the flow in the uterine tube.

In accordance with a third flow restriction option, the control device controls the constriction device to constrict the wall portion, such that the flow of sperms in the uterine tube is substantially stopped, and controls the stimulation device to stimulate the constricted wall portion to cause contraction thereof, such that the flow in the uterine tube is completely stopped. More precisely, the control device may control the stimulation device in a first mode to stimulate the constricted wall portion to completely stop the flow in the uterine tube and to:

a) control the stimulation device in a second mode to cease the stimulation of the wall portion to allow flow in the uterine tube; or b) control the stimulation and constriction devices in the second mode to cease the stimulation of the wall portion and release the wall portion to restore the flow in the uterine tube.

For example, the third flow restriction option may be applied where the present invention is used for controlling sperm flow of a patient who has difficulties getting pregnant. Thus, the restriction and stimulation devices may be implanted on any part of the patient's uterine tubes. The control device may control the constriction device to gently flatten a portion of the uterine tubes to at least almost completely stop the sperm flow, and controls the stimulation device to stimulate the flattened portion to insure that the sperm flow is completely stopped. Since the control device controls the stimulation device to intermittently and individually stimulate the areas of the wall portion, as stated above, the risk of the implanted constriction device injuring the uterine tubes over time is significantly reduced or even eliminated, and it is insured that the effect of the stimulation is maintained over time. When the time for getting pregnant is at an optimum, the control device controls the constriction and stimulation devices to release the portion of the uterine tubes and cease the stimulation, whereby sperms may pass the portion of the uterine tubes.

Where the stimulation device stimulates the constricted wall portion to contract, such that the sperm flow in the uterine tube is stopped, the control device suitably controls the stimulation device to simultaneously and cyclically stimulate a first length of the constricted wall portion and a second length of the constricted wall portion, which is located downstream of the first length, wherein the control device controls the stimulation device to progressively stimulate the first length in the upstream direction of the uterine tube and to progressively stimulate the second length in the downstream direction of the uterine tube.

The control device may control the stimulation device to change the stimulation of the wall portion in response to a sensed physical parameter of the patient or functional parameter of the apparatus. For example, the control device may control the stimulation device to increase the intensity of the stimulation of the wall portion in response to a sensed pressure increase in the uterine tube, such that the flow in the uterine tube remains stopped. Any sensor for sensing a physical parameter of the patient, such as a pressure in the patient's body that relates to the pressure in the uterine tube may be provided, wherein the control device controls the stimulation device in response to signals from the sensor. Such a sensor may for example sense the pressure in the patient's abdomen, the pressure against the implanted constriction device or the pressure on the uterine tube wall of the bodily organ.

For example, a pressure sensor may be applied where the present invention is used for controlling sperm flow of a patient. Thus, the constriction and stimulation devices may be applied on the patient's uterine tubes In accordance with a fourth flow restriction option, the control device controls the constriction device to constrict the wall portion, such that the flow in the uterine tube is stopped. More precisely, the control device may control the constriction device in a first mode to constrict the constricted wall portion to stop the flow in the uterine tube and in a second mode to cease the constriction of the wall portion to restore flow in the uterine tube. In this case, the control device only controls the stimulation device to stimulate the wall portion when needed. A sensor for sensing a physical parameter of the patient's body that relates to the pressure in the uterine tube may be provided, wherein the control device controls the stimulation device in response to signals from the sensor. Such a physical parameter may be a pressure in the patient's abdomen and the sensor may be a pressure sensor.

In some applications of the invention, the implanted constriction device may be designed to normally keep the patient's wall portion of the uterine tubes in the constricted state. In this case, the control device may be used when needed, conveniently by the patient, to control the stimulation device to stimulate the constricted uterine tube wall portion, preferably while adjusting the stimulation intensity, to cause contraction of the wall portion, such that the flow in the uterine tube is at least further restricted or stopped, and to control the stimulation device to cease the stimulation. More precisely, the control device may:

a) control the stimulation device in a first mode to stimulate the constricted wall portion to further restrict the flow in the uterine tube, and control the stimulation device in a second mode to cease the stimulation of the wall portion to increase the flow in the uterine tube; or b) control the stimulation device in a first mode to stimulate the constricted wall portion to stop the flow in the uterine tube, and control the stimulation device in a second mode to cease the stimulation of the wall portion to allow flow in the uterine tube.

Either the first mode or the second mode may be temporary.

The constriction device may include a plurality of separate constriction elements adapted to constrict any wall portions of a series of wall portions of the uterine tube wall, respectively. The control device may control the constriction device to activate the constriction elements in random or in accordance with a predetermined sequence. In this case, the stimulation device includes stimulation elements positioned on the constriction elements, wherein the control device controls the stimulation device to activate the stimulation elements to stimulate any wall portions of the series of wall portions constricted by said constriction elements to contract the organ to close the organ's uterine tube.

Alternatively, the control device controls the constriction device to activate the constriction elements to constrict all of the wall portions of the series of wall portions, and controls the stimulation device to activate the stimulation elements to stimulate any constricted wall portions in random or in accordance with a predetermined sequence to close the organ's uterine tube. The design of the constriction device in the form of a plurality of separate constriction elements makes possible to counteract growth of hard fibrosis where the constriction device is implanted.

Movement of Sperms in a Uterine Tube

The apparatus of the invention can be used for actively moving the sperms in the uterine tube of a patient, as described in the embodiments of the invention listed below. Either to promote or prevent pregnancy.

1) The control device controls the constriction device to close the uterine tube, either at an upstream end or a downstream end of the wall portion, and then controls the constriction device to constrict the remaining part of the wall portion to move the sperms in the uterine tube.

1a) In accordance with a first alternative of the above noted embodiment (1), the control device controls the stimulation device to stimulate the wall portion as the constriction device constricts the remaining part of the wall portion.

1 b) In accordance with a second alternative, the constriction device is adapted to constrict the wall portion to restrict but not stop the flow in the uterine tube. The control device controls the stimulation device to stimulate the wall portion constricted by the constriction device to close the uterine tube, either at an upstream end or a downstream end of the wall portion, and simultaneously controls the constriction device to increase the constriction of the wall portion to move the sperms in the uterine tube.

2) The constriction device is adapted to constrict the wall portion to restrict or vary the flow in the uterine tube, and the control device controls the stimulation device to progressively stimulate the constricted wall portion, in the downstream or upstream direction of the uterine tube, to cause progressive contraction of the wall portion to move the sperms in the uterine tube.

3) The control device controls the constriction device to vary the constriction of the different areas of the wall portion, such that the wall portion is progressively constricted in the downstream or upstream direction of the uterine tube to move the sperms in the uterine tube. The constriction device may include at least one elongated constriction element that extends along the wall portion, wherein the control device controls the elongated constriction element to progressively constrict the wall portion in the downstream or upstream direction of the uterine tube.

3a) In accordance with a preferred alternative of the above noted embodiment (3), the control device controls the stimulation device to progressively stimulate the constricted wall portion to cause progressive contraction thereof in harmony with the progressive constriction of the wall portion performed by the constriction device. Where the constriction device includes at least one elongated constriction element the control device controls the elongated constriction element to progressively constrict the wall portion in the downstream or upstream direction of the uterine tube. Suitably, the elongated constriction element comprises contact surfaces dimensioned to contact a length of the wall portion, when the constriction device constricts the wall portion, and the stimulation device comprises a plurality of stimulation elements distributed along the contact surfaces, such that the stimulation elements stimulate the different areas of the wall portion along the length of the wall portion, when the control device controls the stimulation device to stimulate the wall portion.

4) The constriction device is adapted to constrict any one of a series of wall portions of the uterine tube wall to at least restrict the flow in the uterine tube. The control device controls the constriction device to successively constrict the wall portions of the series of wall portions to move the sperms in the uterine tube in a peristaltic manner.

4a) In accordance with a first alternative of embodiment (4), the constriction device includes a plurality of constriction elements adapted to constrict the wall portions of the uterine tube wall, respectively. The control device controls the constriction device to activate the constriction elements one after the other, so that the wall portions of the series of wall portions are successively constricted along the organ, whereby the sperms in the uterine tube is moved.

4b) In accordance with a second alternative of embodiment (4), the constriction device includes at least one constriction element that is moveable along the wall of the organ to successively constrict the wall portions of the series of wall portions, wherein the control device controls the constriction device to cyclically move the constriction element along the wall portions of the series of wall portions. Preferably, the constriction device comprises a plurality of constriction elements, each of which is moveable along the wall of the organ to successively constrict the wall portions of the series of wall portions, wherein the control device controls the constriction device to cyclically move the constriction elements one after the other along the wall portions of the series of wall portions. Specifically, the constriction device includes a rotor carrying the constriction elements, and the control device controls the rotor to rotate, such that each constriction element cyclically constricts the wall portions of the series of wall portions. Each constriction element suitably comprises a roller for rolling on the wall of the organ to constrict the latter.

4c) In accordance with a preferred alternative of the above noted embodiment (4), the stimulation device stimulates any of the wall portions of the series of wall portions constricted by the constriction device, to close the uterine tube. Where the constriction device includes at least one constriction element, the stimulation device suitably includes at least one stimulation element positioned on the constriction element for stimulating the wall portion constricted by the constriction element to close the uterine tube.

Where the constriction device includes a plurality of constriction elements, the stimulation device suitably includes stimulation elements positioned on the constriction elements for stimulating the wall portions constricted by the constriction elements to close the uterine tube.

5) The constriction device is adapted to constrict any one of a series of wall portions of the uterine tube wall to restrict the flow in the uterine tube, wherein the constriction device includes a plurality of constriction elements adapted to constrict the wall portions of the uterine tube wall, respectively, and the stimulation device includes stimulation elements positioned on the constriction elements for stimulating the wall portions constricted by the constriction elements to close the uterine tube. The control device controls the constriction device to activate the constriction elements to constrict the wall portions of the series of wall portions without completely closing the organ's uterine tube, and controls the stimulation device to activate the stimulation elements to stimulate the wall portions one after the other, so that the wall portions of the series of wall portions are successively contracted along the organ to move the sperms in the uterine tube.

6) The constriction device comprises a first constriction element for constricting the wall portion at an upstream end thereof, a second constriction element for constricting the wall portion at a downstream end thereof, and a third constriction element for constricting the wall portion between the upstream and downstream ends thereof. The control device controls the first, second and third constriction elements to constrict and release the wall portion independently of one another. More specifically, the control device controls the first or second constriction element to constrict the wall portion at the upstream or downstream end thereof to close the uterine tube, and controls the third constriction element to constrict the wall portion between the upstream and downstream ends thereof, whereby the sperms contained in the wall portion between the upstream and downstream ends thereof is moved downstream or upstream in the uterine tube. Optionally, the control device controls the stimulation device to stimulate the wall portion between the upstream and downstream ends thereof, when the third constriction element constricts the wall portion.

6a) In accordance with a first alternative, the control device controls the first constriction element to constrict the wall portion at the upstream end thereof to restrict the flow in the uterine tube and controls the stimulation device to stimulate the constricted wall portion at the upstream end to close the uterine tube. With the uterine tube closed at the upstream end of the constricted wall portion, the control device controls the third constriction element to constrict the wall portion between the upstream and downstream ends thereof, and optionally controls the stimulation device to simultaneously stimulate the wall portion as the latter is constricted by the third constriction element. As a result, the sperms contained in the wall portion between the upstream and downstream ends thereof are moved downstream in the uterine tube.

6b) In accordance with a second alternative, the control device controls the second constriction element to constrict the wall portion at the downstream end thereof to restrict the flow in the uterine tube and controls the stimulation device to stimulate the constricted wall portion at the downstream end to close the uterine tube. With the uterine tube closed at the downstream end of the constricted wall portion, the control device controls the third constriction element to constrict the wall portion between the upstream and downstream ends thereof, and optionally controls the stimulation device to simultaneously stimulate the wall portion as the latter is constricted by the third constriction element. As a result, the sperms contained in the wall portion between the upstream and downstream ends thereof are moved upstream in the uterine tube.

In any of the above noted embodiments (1) to (6b), the stimulation device may stimulate the wall portion with electric pulses.

With the tubular shape of the uterine tubes, a particularly long wall portion thereof may be surgically prepared to extend in zigzag with adjacent walls stitched together by two parallel rows of stitches and with the adjacent walls cut through between the two rows of stitches. As a result, the uterine tube of this long wall portion of the organ can be significantly expanded. In this case, the constriction device of the apparatus of the invention is able to move a considerably larger volume of fluid each time it constricts the long wall portion of the organ.

The various solutions described above under the headline: "Flow restriction" to stop the flow in the uterine tube of the organ may also be used in any of the above noted embodiments (1a), (1b), (4a), (5), (6), (6a) and (6b).

Stimulation

When stimulating neural or muscular tissue there is a risk of injuring or deteriorating the tissue over time, if the stimulation is not properly performed. The apparatus of the present invention is designed to reduce or even eliminate that risk. Thus, in accordance with the present invention, the control device controls the stimulation device to intermittently stimulate different areas of the wall portion of the uterine tube, such that at least two of these areas are stimulated at different points of time that is, the stimulation is shifted from one area to another area over time. In addition, the control device controls the stimulation device, such that an area of the different areas that currently is not stimulated has time to restore substantially normal blood circulation before the stimulation device stimulates the area again. Furthermore, the control device controls the stimulation device to stimulate each area during successive time periods, wherein each time period is short enough to maintain satisfactory blood circulation in the area until the lapse of the time period. This gives the advantage that the apparatus of the present invention enables continuous stimulation of the wall portion of the uterine tube to achieve the desired flow control, while essentially maintaining over time the natural physical properties of the uterine tube without risking injuring the organ.

Also, by physically changing the places of stimulation on the organ over time as described above it is possible to create an advantageous changing stimulation pattern on the uterine tube, in order to achieve a desired flow control.

The control device may control the stimulation device to stimulate one or more of the areas of the wall portion at a time, for example by sequentially stimulating the different areas. Furthermore, the control device may control the stimulation device to cyclically propagate the stimulation of the areas along the wall portion, preferably in accordance with a determined stimulation pattern. To achieve the desired reaction of the uterine tube wall during the stimulation thereof, the control device may control the stimulation device to, preferably cyclically, vary the intensity of the stimulation of the wall portion.

In a preferred embodiment of the invention, the control device controls the stimulation device to intermittently stimulate the areas of the wall portion with pulses that preferably form pulse trains. At least a first area and a second area of the areas of the wall portion may be repeatedly stimulated with a first pulse train and a second pulse train, respectively, such that the first and second pulse trains over time are shifted relative to each other. For example, the first area may be stimulated with the first pulse train, while the second area is not stimulated with said second pulse train, and vice versa. Alternatively, the first and second pulse trains may be shifted relative to each other, such that the first and second pulse trains at least partially overlap each other.

The pulse trains can be configured in many different ways. Thus, the control device may control the stimulation device to vary the amplitudes of the pulses of the pulse trains, the duty cycle of the individual pulses of each pulse train, the width of each pulse of the pulse trains, the length of each pulse train, the repetition frequency of the pulses of the pulse trains, the repetition frequency of the pulse trains, the number of pulses of each pulse train, and/or the off time periods between the pulse trains. Several pulse trains of different configurations may be employed to achieve the desired effect.

In case the control device controls the stimulation device to vary the off time periods between pulse trains that stimulate the respective area of the wall portion, it is also possible to control each off time period between pulse trains to last long enough to restore substantially normal blood circulation in the area when the latter is not stimulated during the off time periods.

Electric Stimulation

In accordance with a preferred embodiment of the invention, the stimulation device is an electrically powered stimulation device that electrically stimulates the uterine tube wall portion of the patient's bodily organ, preferably with electric pulses. This embodiment is particularly suited for applications in which the wall portion includes muscle fibers that react to electrical stimula. In this embodiment, the control device controls the stimulation device to stimulate the wall portion with electric pulses preferably in the form of electric pulse trains, when the wall portion is in the constricted state, to cause contraction of the wall portion. Of course, the configuration of the electric pulse trains may be similar to the above described pulse trains and the control device may control the stimulation device to electrically stimulate the different areas of the wall of the uterine tube in the same manner as described above.

The electric stimulation device suitably comprises at least one, preferably a plurality of electrical elements, such as electrodes, for engaging and stimulating the wall portion with electric pulses. Optionally, the electrical elements may be placed in a fixed orientation relative to one another. The control device controls the electric stimulation device to electrically energize the electrical elements, one at a time, or groups of electrical elements at a time. Preferably, the control device controls the electric stimulation device to cyclically energize each element with electric pulses. Optionally, the control device may control the stimulation device to energize the electrical elements, such that the electrical elements are energized one at a time in sequence, or such that a number or groups of the electrical elements are energized at the same time. Also, groups of electrical elements may be sequentially energized, either randomly or in accordance with a predetermined pattern.

The electrical elements may form any pattern of electrical elements. Preferably, the electrical elements form an elongate pattern of electrical elements, wherein the electrical elements are applicable on the patient's wall of the uterine tube, such that the elongate pattern of electrical elements extends lengthwise along the wall of the uterine tube, and the elements abut the respective areas of the wall portion. The elongate pattern of electrical elements may include one or more rows of electrical elements extending lengthwise along the wall of the uterine tube. Each row of electrical elements may form a straight, helical or zig-zag path of electrical elements, or any form of path. The control device may control the stimulation device to successively energize the electrical elements longitudinally along the elongate pattern of electrical elements in a direction opposite to, or in the same direction as that of, the flow in the patient's uterine tube.

Optionally, the control device may control the stimulation device to successively energize the electrical elements from a position substantially at the center of the constricted wall portion towards both ends of the elongate pattern of electrical elements. Where the uterine tube is to be kept closed for a relatively long time, the control device may control the stimulation device to energize the electrical elements, such that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the uterine tube and without moving fluid or gas in any direction in the uterine tube.

The control device suitably controls the stimulation device to energize the electrical elements, such that the electrical elements currently energized form at least one group of adjacent energized electrical elements. In accordance with a first alternative, the elements in the group of energized electrical elements form one path of energized electrical elements. The path of energized electrical elements may extend at least in part around the patient's uterine tubes. In a second alternative, the elements of the group of energized electrical elements may form two paths of energized electrical elements extending on mutual sides of the patient's uterine tube, preferably substantially transverse to the flow direction in the uterine tube. In a third alternative, the elements of the group of energized electrical elements may form more than two paths of energized electrical elements extending on different sides of the patient's uterine tube, preferably substantially transverse to the flow direction in the patient's uterine tube.

In accordance with a preferred embodiment of the invention, the electrical elements form a plurality of groups of elements, wherein the groups form a series of groups extending along the patient's organ in the flow direction in the patient's uterine tube. The electrical elements of each group of electrical elements may form a path of elements extending at least in part around the patient's uterine tube. In a first alternative, the electrical elements of each group of electrical elements may form more than two paths of elements extending on different sides of the patient's uterine tube, preferably substantially transverse to the flow direction in the patient's uterine tube. The control device may control the stimulation device to energize the groups of electrical elements in the series of groups in random, or in accordance with a predetermined pattern. Alternatively, the control device may control the stimulation device to successively energize the groups of electrical elements in the series of groups in a direction opposite to, or in the same direction as that of, the flow in the patient's uterine tube, or in both said directions starting from a position substantially at the center of the constricted wall portion. For example, groups of energized electrical elements may form advancing waves of energized electrical elements, as described above; that is, the control device may control the stimulation device to energize the groups of electrical elements, such that energized electrical elements form two waves of energized electrical elements that simultaneously advance from the center of the constricted wall portion in two opposite directions towards both ends of the elongate pattern of electrical elements.

A structure may be provided for holding the electrical elements in a fixed orientation. Although the structure may be separate from the constriction device, it is preferable that the structure is integrated in the constriction device, which is a practical design and facilitates implantation of the constriction and stimulation devices. Where the electrical elements form an elongate pattern of electrical elements, the structure may be applicable on the patient's uterine tube such that the elongate pattern of electrical elements extends along the uterine tube in the same direction as that of the flow in the patient's uterine tube and the elements abut the respective areas of the wall portion of the uterine tube.

Thermal Stimulation

In another embodiment of the invention, the stimulation device thermally stimulates the wall portion of the uterine tube. Thus, the control device may control the stimulation device to cool the wall portion, when the wall portion is constricted, to cause contraction of the wall portion. For example, the constriction device may constrict the wall portion to at least restrict the flow in the uterine tube, and the control device may control the stimulation device to cool the constricted wall portion to cause contraction thereof, such that the flow in the uterine tube is at least further restricted, or further restricted but not stopped, or stopped. Alternatively, the control device may control the stimulation device to heat the wall portion, when the wall portion is constricted and contracted, to cause expansion of the wall portion. Where the wall portion includes a blood vessel, the control device may control the stimulation device to cool the blood vessel to cause contraction thereof, or heat the blood vessel to cause expansion thereof. Where applicable, thermal stimulation may be practised in any of the embodiments of the present invention, and the thermal stimulation may be controlled in response to various sensors, for example strain, motion or pressure sensors.

Sensor Controlled Constriction and/or Stimulation Device

As mentioned above, the apparatus may comprise at least one implantable sensor, wherein the control device controls the constriction device and/or the stimulation device in response to signals from the sensor. Generally, the sensor directly or indirectly senses at least one physical parameter of the patient, or at least one functional parameter of the apparatus, or at least one functional parameter of a medical implant in the patient.

Many different kinds of sensor for sensing physical parameters may be used. For example motion sensors for sensing uterine tube motion, i.e. natural contractions, uterine tube contractions, pressure sensors for sensing pressure in the organ, strain sensors for sensing strain of the uterine tube, flow sensors for sensing fluid flow in the uterine tube of the organ, spectro-photometrical sensors, Ph-sensors for sensing acidity or alkalinity of the fluid in the uterine tube, oxygen-sensors sensors for sensing the oxygen content of the fluid in the uterine tube, or sensors for sensing the distribution of the stimulation on the stimulated uterine tube. Any conceivable sensors for sensing any other kind of useful physical parameter may be used.

Many different kinds of sensors that sense functional parameters of the apparatus may also be used for the control of the constriction device and/or the stimulation device. For example sensors for sensing electric parameters of implanted electric components of the apparatus, or sensors for sensing the performance of implanted motors of the apparatus.

The sensor may comprise a pressure sensor for sensing as the physical parameter a pressure in the patient's body that relates to the pressure in the uterine tube of the patient, wherein the control device controls the constriction device and/or stimulation device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909, incorporated herein by reference. For example, the control device may control the constriction device and/or stimulation device to change the constriction of the patient's uterine tube wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the uterine tube during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Adjustable Constriction Device

In several alternative embodiments of the invention, the constriction device is adjustable. In these embodiments, there is an operation device for operating the adjustable constriction device to change the constriction of the patient's uterine tube wall portion, and the constriction and stimulation devices form a constriction/stimulation unit. Preferably, the constriction and stimulation devices of the constriction/ stimulation unit are integrated in a single piece suitable for implantation. The constriction device of the unit comprises contact surfaces dimensioned to contact a length of a uterine tube wall portion, and the stimulation device of the unit comprises a plurality of stimulation elements provided on and distributed along the contact surfaces. When the control device controls the stimulation device to stimulate the wall portion, the stimulation elements stimulate different areas of the wall portion along the length of the wall portion. The stimulation elements preferably comprise electric elements, as described above, for stimulating the wall portion with electric pulses. However, in most applications of the present invention, other kinds of stimulations, such as thermal stimulation, could be suitable to employ.

The operation device operates the adjustable constriction device of the constriction/stimulation unit in a manner that depends on the design of the constriction device, as will be explained by the following examples of embodiments. 1) The constriction device comprises at least two elongated clamping elements having the contact surfaces and extending along the wall portion on different sides of the organ, and the operation device operates the clamping elements to clamp the uterine tube wall portion between the clamping elements to constrict the wall portion.

2) The constriction device comprises one elongate clamping element having the contact surfaces and extending along the wall portion on one side of the uterine tube, and the operation device operates the clamping element to clamp the wall portion between the clamping element and the bone or tissue of the patient to constrict the wall portion.

3) The constriction device comprises at least two engagement elements having the contact surfaces and positioned on different sides of the uterine tube, and the operation device rotates the engagement elements, such that the engagement elements engage and constrict the wall portion of the uterine tube.

4) The constriction device comprises at least two articulated clamping elements having the contact surfaces and positioned on different sides of the uterine tube, and the operation device moves the clamping elements towards each other to clamp the wall portion of the uterine tube between the clamping elements, to constrict the wall portion.

5) The constriction device comprises at least two separate clamping elements having the contact surfaces, at least one of the clamping elements being pivoted, such that it may turn in a plane in which the loop of the constriction member extends, and the operation device turns the pivoted clamping element to change the size of the constriction opening.

6) The constriction device comprises at least one elongated constriction member having the contact surfaces, and forming means for forming the constriction member into at least a substantially closed loop around the uterine tube, wherein the loop defines a constriction opening. The operation device operates the constriction member in the loop to change the size of the constriction opening.

6a) The elongated constriction member comprises a belt having the contact surfaces, and the operation device operates the belt to change the longitudinal extension of the belt in the loop to change the size of the constriction opening. The forming means may form the constriction member or belt into a loop having at least one predetermined size.

6b) The elongated constriction member is operable to change the size of the constriction opening, such that the outer circumferential confinement surface of the constriction device is changed, or, alternatively, is unchanged.

6c) The elongated constriction member is elastic and varies in thickness as seen in a cross-section there through, and is operable to turn around the longitudinal extension of the constriction member.

6d) The elongated constriction member comprises two substantially or partly semi-circular frame elements having the contact surfaces and hinged together, such that the semi-circular elements are swingable relative to each other from a fully open state in which they substantially or partly form a circle to a fully folded state in which they substantially form a semi-circle.

7) The constriction device is adapted to bend the wall portion of the uterine tube to constrict the latter.

In the above noted embodiments (1) to (7), it is important that the constriction device is designed to constrict said length of the uterine tube wall portion of the patient's uterine tube. For this purpose, the constriction device may include two or more of the described constriction elements/members to be applied in a row along said length of the wall portion, wherein said row extends in the direction of flow in the uterine tube of the uterine tube. Preferably, such constriction elements/members are non-inflatable and mechanically operable or adjustable.

In the above noted embodiments (1) to (7), the operation device may either mechanically or hydraulically adjust the constriction device of the constriction/stimulation unit. Also, the operation device may comprise an electrically powered operation device for operating the constriction device. For many applications of the present invention, the operation device suitably operates the constriction device, such that the through-flow area of the uterine tube assumes a size in the constricted state that enables the stimulation device to contract the wall portion such that the flow in the uterine tube is stopped.

Mechanical Operation

Where the operation device mechanically operates the constriction device of the constriction/stimulation unit, it may be non-inflatable. Furthermore, the operation device may comprise a servo system, which may include a gearbox. The term "servo system" encompasses the normal definition of a servo mechanism, i.e., an automatic device that controls large amounts of power by means of very small amounts of power, but may alternatively or additionally encompass the definition of a mechanism that transfers a weak force acting on a moving element having a long stroke into a strong force acting on another moving element having a short stroke. Preferably, the operation device operates the constriction device in a non-magnetic and/or non-manual manner. A motor may be operatively connected to the operation device. The operation device may be operable to perform at least one reversible function and the motor may be capable of reversing the function.

Hydraulic Operation

Where the operation device hydraulically operates the constriction device of the constriction/stimulation unit, it includes hydraulic means for adjusting the constriction device.

In an embodiment of the invention, the hydraulic means comprises a reservoir and an expandable/contractible cavity in the constriction device, wherein the operation device distributes hydraulic fluid from the reservoir to expand the cavity, and distributes hydraulic fluid from the cavity to the reservoir to contract the cavity. The cavity may be defined by a balloon of the constriction device that abuts the uterine tube wall portion of the patient's uterine tube, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/ cylinder mechanism.

Where the hydraulic means comprises a cavity in the constriction device, the apparatus of the invention can be designed in accordance with the options listed below.

1) The reservoir comprises first and second wall portions, and the operation device displaces the first and second wall portions relative to each other to change the volume of the reservoir, such that fluid is distributed from the reservoir to the cavity, or from the cavity to the reservoir.

1 a) The first and second wall portions of the reservoir are displaceable relative to each other by at least one of a magnetic device, a hydraulic device or an electric control device.

2) The operation device comprises a pump for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) The apparatus comprises a fluid conduit between the pump and the cavity, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. The apparatus further comprises a motor for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, the operation device distributes hydraulic fluid between the reservoir and the cylinder/piston mechanism to adjust the constriction device.

In a special embodiment of the invention, the operation device comprises a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir. The reverse servo is particularly suited for manual operation thereof.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operable to distribute hydraulic fluid between the main reservoir and the hydraulic means to adjust the constriction device. More specifically, the main reservoir is provided with first and second wall portions operatively connected to the first and second wall portions of the expandable servo reservoir, such that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the servo and main reservoirs are dimensioned, such that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaceable relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means comprises a hydraulically operable mechanical construction, the operation device may include the reverse servo described above. In a further embodiment of the invention, the hydraulic means include first and second hydraulically interconnected expandable/contractible reservoirs. The first reservoir is operatively connected to the constriction device, such that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, such that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements having the above-mentioned contact surfaces and extending along the wall portion on different sides of the uterine tube. The hydraulic means, which may include the reverse servo described above, hydraulically moves the elongated clamping elements towards the wall portion to constrict the wall portion. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Design of Control Device

The control device suitably controls the constriction/stimulation unit from outside the patient's body. Preferably, the control device is operable by the patient. For example, the control device may comprise a manually operable switch for switching on and off the constriction/stimulation unit, wherein the switch is adapted for subcutaneous implantation in the patient to be manually or magnetically operated from outside the patient's body. Alternatively, the control device may comprise a hand-held wireless remote control, which is conveniently operable by the patient to switch on and off the constriction/stimulation unit. The wireless remote control may also be designed for application on the patient's body like a wristwatch. Such a wristwatch type of remote control may emit a control signal that follows the patient's body to implanted signal responsive means of the apparatus.

Where the control device wirelessly controls the constriction/stimulation unit from outside the patient's body, the wireless control function is preferably performed in a non-magnetic manner, i.e., the control device controls the constriction device of the constriction/stimulation unit in a non-magnetic manner. The patient may use the remote control to control the constriction/stimulation unit to adjust the stimulation intensity and/or adjust the constriction of the wall portion. The wireless remote control may comprise at least one external signal transmitter or transceiver and at least one internal signal receiver or transceiver implantable in the patient.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above control signals may comprise wave signals, for example a sound wave signal, an ultrasound wave signal, an electromagnetic wave signal, an infrared light signal, a visible light signal, an ultra violet light signal, a laser light signal, a microwave signal, a radio wave signal, an x-ray radiation signal or a gamma radiation signal. Alternatively, the control signal may comprise an electric or magnetic field, or a combined electric and magnetic field.

As mentioned above, the control signal may follow the patient's body to implanted signal responsive means of the apparatus.

The control device may include a programmable internal control unit, such as a microprocessor, implantable in the patient for controlling the constriction/stimulation unit. The control device may further include an external control unit intended to be outside the patient's body, wherein the internal control unit is programmable by the external control unit. For example, the internal control unit may be programmable for controlling the constriction/stimulation unit over time, suitably in accordance with an activity schedule program. The apparatus of the invention may comprise an external data communicator and an implantable internal data communicator communicating with the external data communicator, wherein the internal communicator feeds data related to the constriction/stimulation unit back to the external data communicator or the external data communicator feeds data to the internal data communicator.

Source of Energy

The present invention also presents a solution for supplying energy for use in connection with the operation of the constriction/stimulation unit. Thus, in a broad sense, the present invention provides an apparatus for controlling a flow of sperms in a uterine tube formed by a uterine tube wall of a patient's uterine tube, wherein the apparatus comprises an implantable constriction device for gently constricting a portion of the uterine tube wall to influence the flow in the uterine tube, a stimulation device for intermittently and individually stimulating different areas of the wall portion, as the constriction device constricts the wall portion, to cause contraction of the wall portion to further influence the flow in the uterine tube, wherein the constriction and stimulation devices form an operable constriction/stimulation unit, a source of energy, and a control device operable from outside the patient's body to control the source of energy to release energy for use in connection with the operation of the constriction/stimulation unit. In a simple form of the invention, the source of energy, such as a battery or accumulator, is implantable in the patient's body.

Transmission of Wireless Energy

In a more sophisticated form of the invention, which is preferable, the source of energy is external to the patient's body and the control device controls the external source of energy to release wireless energy. In this sophisticated form of the invention, the apparatus comprises an energy-transmission device that transmits the released wireless energy from outside the patient's body to inside the patient's body. Among many things the wireless energy may comprise electromagnetic energy, an electric field, an electromagnetic field or a magnetic field, or a combination thereof, or electromagnetic waves. The energy-transmission device may transmit wireless energy for direct use in connection with the operation of the constriction/stimulation unit, as the wireless energy is being transmitted. For example, where an electric motor or pump operates the constriction device, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy for driving the motor or pump. Such components may include coils integrated in the motor or pump, or materials influenced by magnetic fields, or permanent magnets, wherein the magnetic or electromagnetic field influences the coils to generate a current for driving the motor or pump, or influences the material or permanent magnets to create kinetic energy for driving the motor or pump.

Preferably, the energy-transmission device transmits energy by at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or ultrasound wave signal. The wireless signal may be a digital or analogue signal, or a combination of a digital and analogue signal.

Transforming Wireless Energy

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. In this case, the energy-transforming device may include a piezo-electric element for transforming the sound waves into electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function differently from or similar to the energy-transmission device. In a special embodiment, the energy-transforming device comprises at least one element, such as at least one semiconductor, having a positive region and a negative region, exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy-transforming device may transform the energy of the first form directly or indirectly into the energy of the second form. An implantable motor or pump for operating the constriction device of the constriction/stimulation unit may be provided, wherein the motor or pump is powered by the energy of the second form. The constriction device may be operable to perform at least one reversible function and the motor may be capable of reversing the function. For example, the control device may shift polarity of the energy of the second form to reverse the motor.

The energy-transforming device may directly power the motor or pump with the transformed energy, as the energy of the second form is being transformed from the energy of the first form. Preferably, the energy-transforming device directly operates the constriction/stimulation unit with the energy of the second form in a non-magnetic, non-thermal or non-mechanical manner.

Normally, the constriction/stimulation unit comprises electric components that are energized with electrical energy. Other implantable electric components of the apparatus may be at least one voltage level guard or at least one constant current guard. Therefore, the energy-transforming device may transform the energy of the first form into a direct current or pulsating direct current, or a combination of a direct current and pulsating direct current. Alternatively, the energy-transforming device may transform the energy of the first form into an alternating current or a combination of a direct and alternating current.

The apparatus of the invention may comprise an internal source of energy implantable in the patient for supplying energy for the operation of the constriction/stimulation unit. The apparatus may further comprise an implantable switch operable to switch from an "off" mode, in which the internal source of energy is not in use, to an "on" mode, in which the internal source of energy supplies energy for the operation of the constriction/stimulation unit, and/or for energizing implanted electronic components of the apparatus. The switch may be operable by the energy of the first form transmitted by the energy-transmission device or by the energy of the second form supplied by the energy-transforming device. The described switch arrangement reduces power consumption of the apparatus between operations.

The internal source of energy may store the energy of the second form supplied by the energy-transforming device. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the apparatus of the invention comprises an implantable stabilizer for stabilizing the energy of the second form. Where the energy of the second form is electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Although the constriction/stimulation unit in the embodiments described above is designed as a single piece, which is most practical for implantation, it should be noted that as an alternative the constriction device and stimulation device could be designed as separate pieces. Any one of the constriction and stimulation units described above may alternatively be replaced by two or more separate constriction/stimulation elements, which are controlled independently of one another.

In one embodiment, the apparatus comprises an implantable constriction device for constricting each one of the female's uterine tubes to restrict the passageway thereof, and a control device for controlling said constriction device to constrict the uterine tube such that an sperm appearing in the passageway of the uterine tube is prevented from entering the uterine cavity, and to release the uterine tube such that an sperm existing in the passageway of the uterine tube is allowed to enter the uterine cavity. The constriction device may gently constrict at least one portion of the uterine tube wall of the uterine tube to restrict the passageway thereof, and an implantable stimulation device may be provided for stimulating the uterine tube wall portion, wherein the control device controls said stimulation device to stimulate the uterine tube wall portion, as said constriction device constricts the uterine tube wall portion, to cause contraction of the uterine tube wall portion to further restrict the passageway of the uterine tube.

Alternatively, the sperm flow control apparatus comprises an implantable constriction device for gently constricting at least one portion of the uterine tube wall of each one of the female's uterine tubes to restrict the passageway thereof, a stimulation device for stimulating the uterine tube wall portion of the uterine tube, and a control device for controlling said stimulation device to stimulate the uterine tube wall portion, as said constriction device constricts the uterine tube wall portion, to cause contraction of the uterine tube wall portion to further restrict the passageway of the uterine tube to prevent an sperm existing in the uterine tube from entering the uterine cavity.

Alternatively, the sperm flow control apparatus comprises an implantable stimulation device for stimulating a portion of the uterine tube wall of each one of the female's uterine tubes, and a control device for controlling said stimulation device to stimulate the uterine tube wall portion of the uterine tube to cause contraction of the uterine tube wall portion, such that the passageway of the uterine tube is restricted to prevent an sperm appearing in the uterine tube from entering the uterine cavity, and to cease stimulating the uterine tube wall portion of the uterine tube to allow an sperm existing in the passageway of the uterine tube to enter the uterine cavity.

The present invention also provides a method for using an apparatus as described above to control a flow of sperms in a female patient's uterine tube, the method comprising:

providing a wireless remote control adapted to control the constriction device and/or stimulation device from outside the patient's body, and

operating the wireless remote control by the patient, when the patient wants to influence the flow of sperms in the uterine tube.

The present invention also provides a method for controlling a flow of sperms in a female patient's uterine tube, the method comprising:

a) gently constricting at least one portion of the uterine tube wall to influence the flow in the uterine tube, and b) stimulating the constricted wall portion to cause contraction of the wall portion to further influence the flow of sperm in the uterine tube.

The present invention also provides a method for controlling a flow of sperms in a female patient's uterine tube, the method comprising:

stimulating the wall portion to cause contraction of the wall portion to influence the flow of sperm in the uterine tube.

Said stimulation device may be combined with a constriction device described above in the all the method embodiments described herein as well as use all the different method embodiments related to the stimulation device described herein.

The present invention also provides a method for controlling a flow of sperms in a female patient's uterine tube, the method comprising:

constricting at least one portion of the uterine tube wall to influence the flow of sperm in the uterine tube.

Said constriction device may be combined with a stimulation device in the all the method embodiments described herein, as well as use all the different method embodiments related to the constriction device and methods described herein.

The invention also provides an apparatus:

for controlling a flow of sperms in an uterine tube of a female patient, the apparatus comprising:

a stimulation device for stimulating the wall portion of the uterine tube wall to constrict and influence the flow of sperm in an uterine tube, and a control device for controlling the stimulation device to stimulate the uterine tube wall portion, to cause contraction of the uterine tube wall portion to constrict and influence the flow of sperms in the uterine tube.

Said stimulation device may be combined with a constriction device described above in the all the embodiments described herein as well as use all the different embodiments related to the stimulation device described herein.

The invention also provides an apparatus:

for controlling a flow of sperms in an uterine tube of a female patient, the apparatus comprising:

an implantable constriction device for constricting at least one portion of the uterine tube wall to at least partly constrict the uterine tube, and a control device for controlling the constriction device to constricts the uterine tube wall portion, to cause contraction of the uterine tube wall portion to influence the flow of sperms in the uterine tube.

Said constriction device may be combined with a stimulation device described above in the all the embodiments described herein, as well as use all the different embodiments related to the constriction device described herein.

Furthermore an embodiment using an apparatus for controlling a flow of sperms in an uterine tube of a female patient, the apparatus comprising:

an implantable restriction device for constricting at least one portion of the uterine tube wall to at least partly constrict the uterine tube, wherein said restriction device is adapted to resestrict more than one area of the uterine tube to prevent living sperm to pass all the restriction areas.

Said restriction device may comprise:

a) a constriction device for constricting the wall portion of the uterine tube wall to constrict the uterine tube to prevent living sperm to pass all the constricted areas.

b) a stimulation device for stimulating the wall portion of the uterine tube wall to restrict the uterine tube to prevent living sperm to pass all the restriction areas.

Said restriction device mayb also comprise a restriction device comprises two or more restriction areas, wherein said restriction device are adapted to switch the restriction between the two or more restriction areas, and further adapted to cause sperm being looked in a restricted portion of the uterine tube having one down stream and one up stream restriction to always prevent living sperm to pass all the restriction areas.

1. Another method for controlling a flow of sperms in an uterine tube of a female patient, the apparatus comprising: an implantable restriction device, the methiod comprising the steps of:

constricting at least one portion of the uterine tube wall to at least partly constrict the uterine tube, resestricting more than one area of the uterine tube to prevent living sperm to pas all the restriction areas, wherein said restriction device comprise: a restriction device for constricting the wall portion of the uterine tube wall to constrict the uterine tube to prevent living sperm to pas all the constricted areas alternatively, wherein said restriction device comprise: a stimulation device for stimulating the wall portion of the uterine tube wall to restrict the uterine tube to prevent living sperm to pas all the restriction areas. The may be provided between the two or more restriction areas, causing sperm being looked in a restricted portion of the uterine tube having one down stream and one up stream restriction to prevent living sperm to pas all the restricted areas.

BRIEF DESCRIPTION OF THE DRAWINGS

FIGS. 7A and 7B show different steps of an electric stimulation mode performed by the apparatus of FIG. 2, while the apparatus is constricting a uterine tube wall of a patient's uterine tube.

FIG. 32 is a cross-sectional view of a reservoir having a variable volume controlled by a remote control motor.

FIGS. 33A and 33B are perspective views of a reverse servo in accordance with a particular embodiment of the hydraulic operation principle shown in FIG. 31C.

FIGS. 36A-36E schematically illustrate different operation stages of an embodiment of the invention, in which a constriction device and a stimulation device co-operate to move the sperms in the uterine tube of a patient's uterine tube.

FIG. 55C is an end view of the embodiment of FIG. 55B.

FIGS. 62A-D show a second embodiment of a constriction device.

DETAILED DESCRIPTION OF THE INVENTION

Figure 1A:
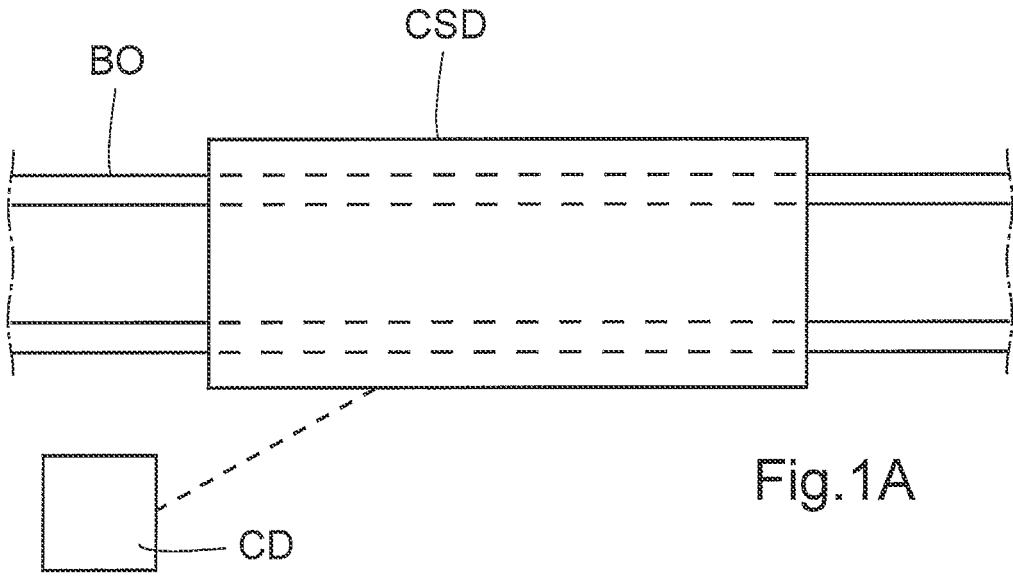
FIGS. 1A, 1B, 1C, 1D and 1E schematically illustrate different states of operation of a general embodiment of an apparatus according to the present invention.

Referring to the drawing figures, like reference numerals designate identical or corresponding elements throughout the several figures.

Figure 1B:
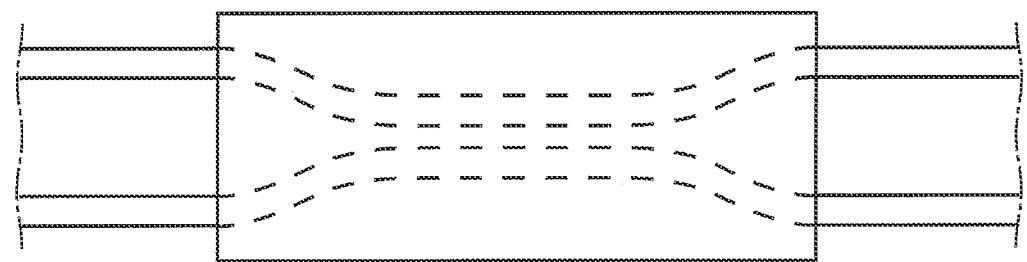
Figure 1C:
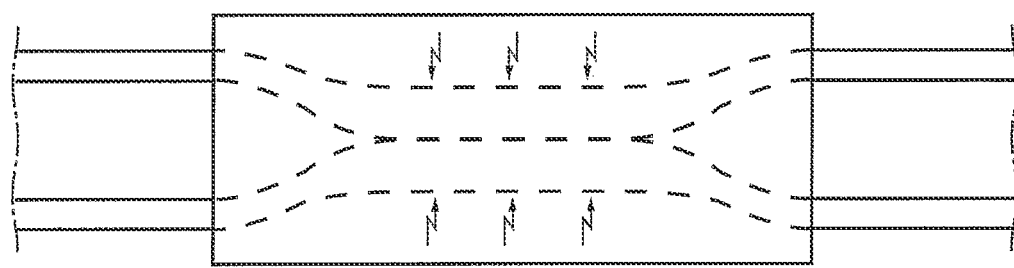

FIGS. 1A, 1B and 1C schematically illustrate different states of operation of a generally designed apparatus according to the present invention, when the apparatus is applied on a wall portion of a uterine tube designated BO. The apparatus includes a constriction device and a stimulation device, which are designated CSD, and a control device designated CD for controlling the constriction and stimulation devices CSD. FIG. 1A shows the apparatus in an inactivation state, in which the constriction device does not constrict the uterine tube BO and the stimulation device does not stimulate the uterine tube BO. FIG. 1B shows the apparatus in a constriction state, in which the control device CD controls the constriction device to gently constrict the wall portion of the uterine tube BO to a constricted state, in which the blood circulation in the constricted wall portion is substantially unrestricted and the flow in the uterine tube of the wall portion is restricted. FIG. 1C shows the apparatus in a stimulation state, in which the control device CD controls the stimulation device to stimulate different areas of the constricted wall portion, so that almost the entire wall portion of the uterine tube BO contracts (thickens) and closes the uterine tube.

Figure 1D:
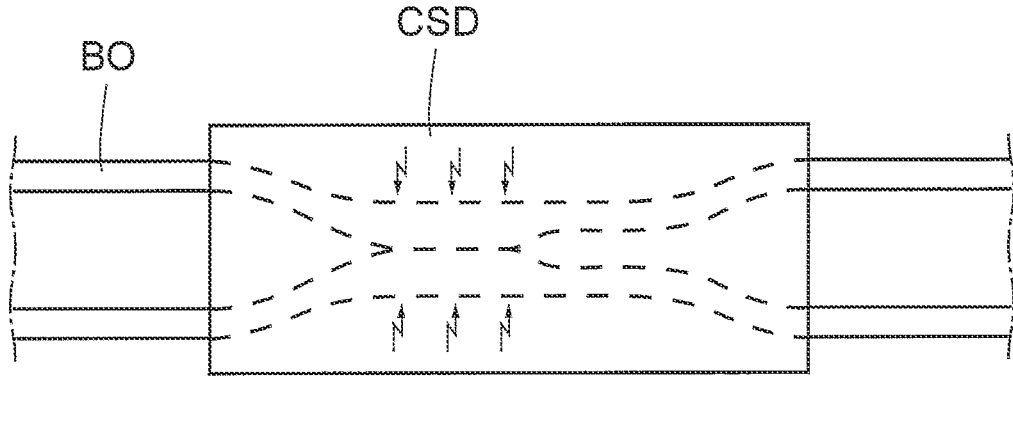
Figure 1E:
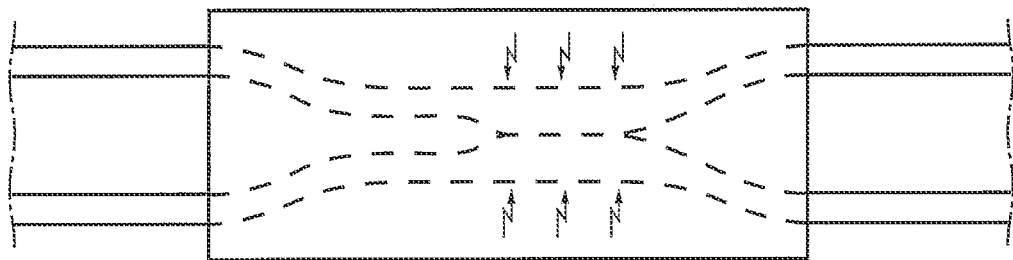

FIGS. 1D and 1E show how the stimulation of the constricted wall portion can be cyclically varied between a first stimulation mode, in which the left area of the wall portion (see FIG. 1D) is stimulated, while the right area of the wall portion is not stimulated, and a second stimulation mode, in which the right area of the wall portion (see FIG. 1E) is stimulated, while the left area of the wall portion is not stimulated, in order to maintain over time satisfactory blood circulation in the constricted wall portion.

It should be noted that the stimulation modes shown in FIGS. 1D and 1E only constitute a principle example of how the constricted wall portion of the uterine tube BO may be stimulated. Thus, more than two different areas of the constricted wall portion may be simultaneously stimulated in cycles or successively stimulated. Also, groups of different areas of the constricted wall portion may be successively stimulated.

Figures 1F, 1G, 1H:
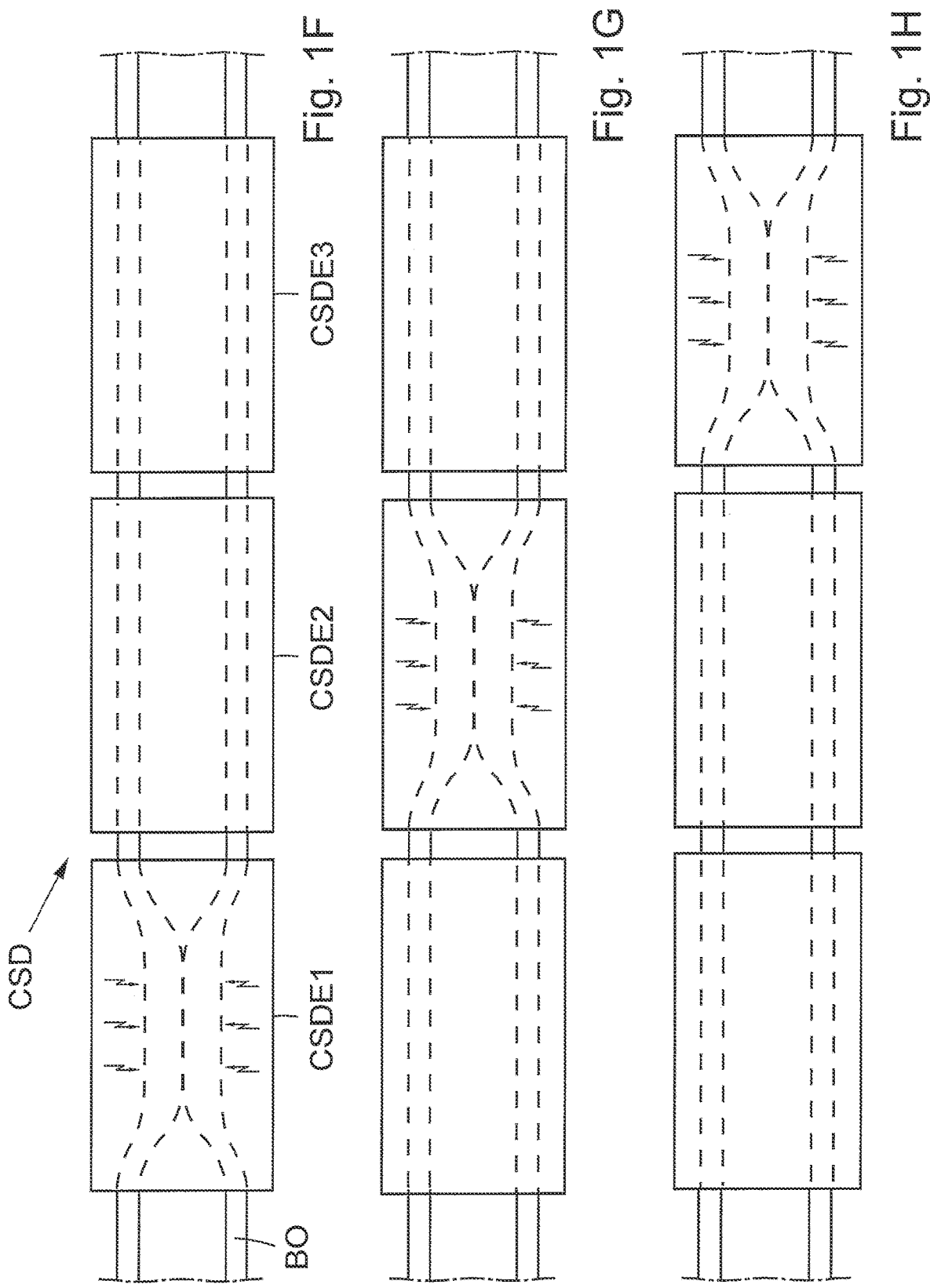
FIGS. 1F, 1G and 1H illustrate different states of operation of a modification of the general embodiment.

FIGS. 1F, 1G and 1H illustrate different states of operation of a modification of the general embodiment shown in FIGS. 1A-1E, wherein the constriction and stimulation devices CSD include several separate constriction/stimulation elements, here three elements CSDE1, CSDE2 and CSDE3. FIG. 1F shows how the element CSDE1 in a first state of operation is activated to both constrict and stimulate the uterine tube BO, so that the uterine tube of the uterine tube BO is closed, whereas the other two elements CSDE2 and CSDE3 are inactivated. FIG. 1G shows how the element CSDE2 in a second following state of operation is activated, so that the uterine tube of the uterine tube BO is closed, whereas the other two elements CSDE1 and CSDE3 are inactivated. FIG. 1H shows how the element CSDE3 in a following third state of operation is activated, so that the uterine tube of the uterine tube BO is closed, whereas the other two elements CSDE1 and CSDE2 are inactivated. By shifting between the first, second and third states of operation, either randomly or in accordance with a predetermined sequence, different portions of the uterine tube can by temporarily constricted and stimulated while maintaining the uterine tube closed, whereby the risk of injuring the uterine tube is minimized. It is also possible to activate the elements CSDE1-CSDE3 successively along the uterine tube to move sperms in the uterine tube.

Figures 1I, 1K, 1L:
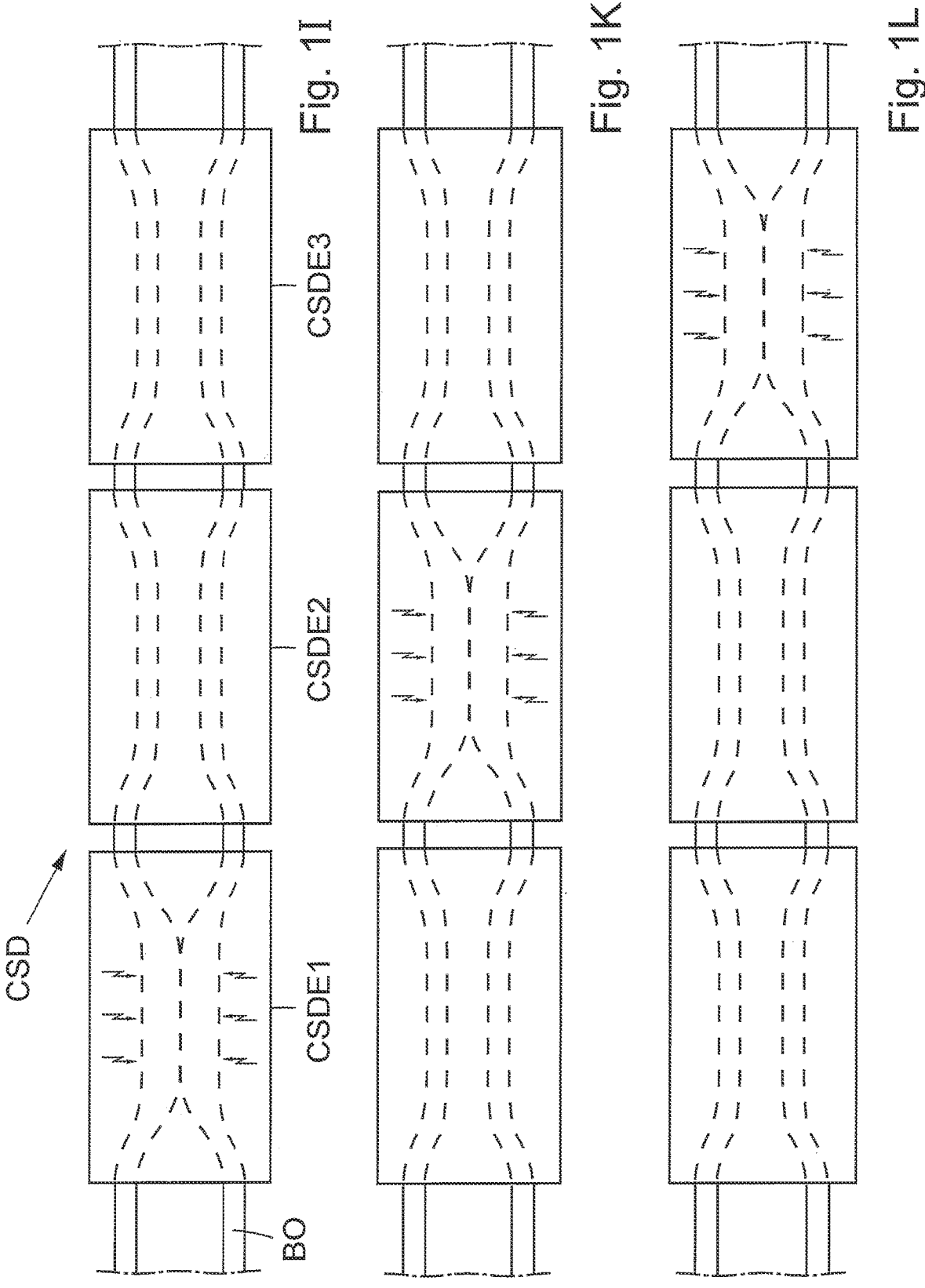
FIGS. 1I, 1K and 1L illustrate an alternative mode of operation of the modification of the general embodiment.

FIGS. 1I, 1K and 1L illustrate an alternative mode of operation of the modification of the general embodiment. Thus, FIG. 1I shows how the element CSDE1 in a first state of operation is activated to both constrict and stimulate the uterine tube BO, so that the uterine tube BO is closed, whereas the other two elements CSDE2 and CSDE3 are activated to constrict but not stimulate the uterine tube BO, so that the uterine tube BO is not completely closed where the elements CSDE2 and CSDE3 engage the uterine tube BO. FIG. 1K shows how the element CSDE2 in a second following state of operation is activated to both constrict and stimulate the uterine tube BO, so that the uterine tube BO is closed, whereas the other two elements CSDE1 and CSDE3 are activated to constrict but not stimulate the organ BO, so that the uterine tube BO is not completely closed where the elements CSDE1 and CSDE3 engage the uterine tube BO. FIG. 1L shows how the element CSDE3 in a following third state of operation is activated to both constrict and stimulate the uterine tube BO, so that the uterine tube BO is closed, whereas the other two elements CSDE1 and CSDE2 are activated to constrict but not stimulate the uterine tube BO, so that the uterine tube BO is not completely closed where the elements CSDE1 and CSDE2 engage the uterine tube BO. By shifting between the first, second and third states of operation, either randomly or in accordance with a predetermined sequence, different portions of the uterine tube can by temporarily stimulated while maintaining the uterine tube closed, whereby the risk of injuring the uterine tube is reduced. It is also possible to activate the stimulation of the elements CSDE1-CSDE3 successively along the uterine tube BO to move fluids and/or other bodily matter in the uterine tube.

Figure 3:
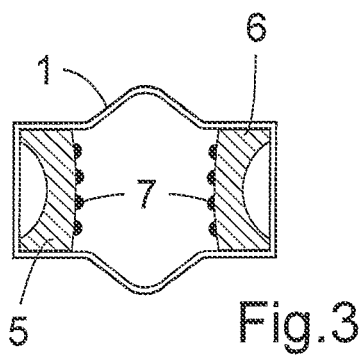
FIG. 3 is a cross-section along line III-III in FIG. 2.
Figure 2:
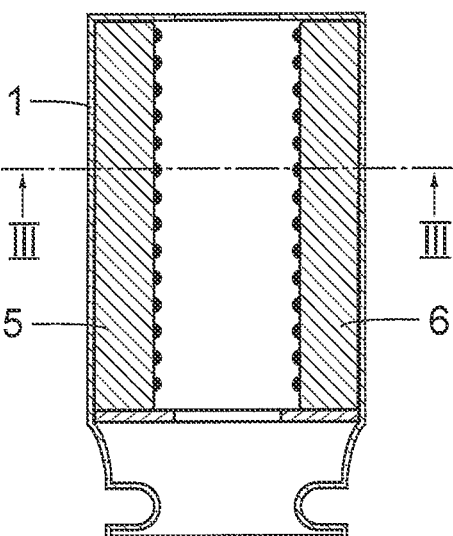
FIG. 2 is a longitudinal cross-section of a preferred embodiment of the apparatus according to the invention including a constriction device and an electric stimulation device.
Figure 4:
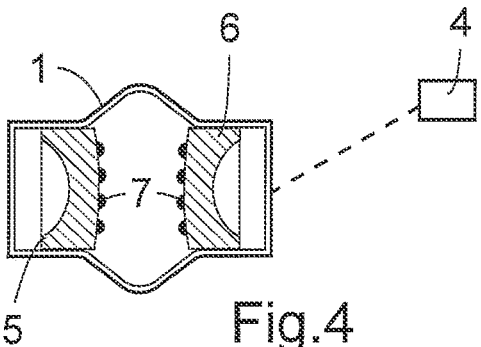
FIG. 4 is the same cross-section shown in FIG. 3, but with the apparatus in a different state of operation.

FIGS. 2-4 show basic components of an embodiment of the apparatus according to the invention for controlling a flow of sperms in a uterine tube formed by a uterine tube wall of a patient's uterine tube. The apparatus comprises a tubular housing 1 with open ends, a constriction device 2 arranged in the housing 1, a stimulation device 3 integrated in the constriction device 2, and a control device 4 (indicated in FIG. 4) for controlling the constriction and stimulation devices 2 and 3. The constriction device 2 has two elongate clamping elements 5, 6, which are radially movable in the tubular housing 1 towards and away from each other between retracted positions, see FIG. 3, and clamping positions, see FIG. 4. The stimulation device 3 includes a multiplicity of electrical elements 7 positioned on the clamping elements 5, 6, so that the electrical elements 7 on one of the clamping elements 5, 6 face the electrical elements 7 on the other clamping element. Thus, in this embodiment the constriction and stimulation devices form a constriction/stimulation unit, in which the constriction and stimulation devices are integrated in a single piece.

The constriction and stimulation devices may also be separate from each other. In this case, a structure may be provided for holding the electrical elements 7 in a fixed orientation relative to one another. Alternatively, the electrical elements 7 may include electrodes that are separately attached to the wall portion of the patient's uterine tube.

Figure 5A:
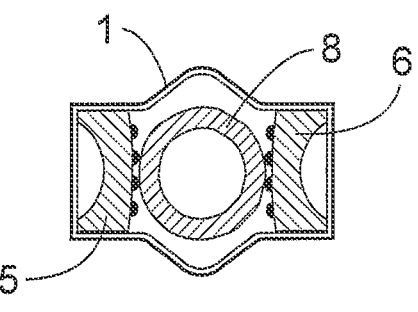
FIGS. 5A, 5B and 5C are cross-sections of the embodiment of FIG. 2 showing different states of operations with the apparatus applied on a uterine tube wall of a patient's uterine tube.
Figure 5B:
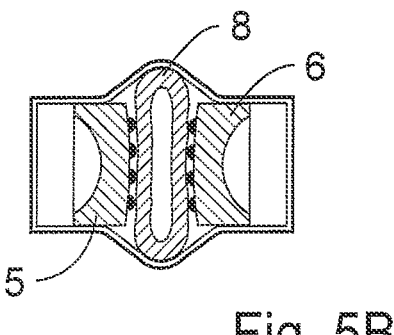
Figure 5C:
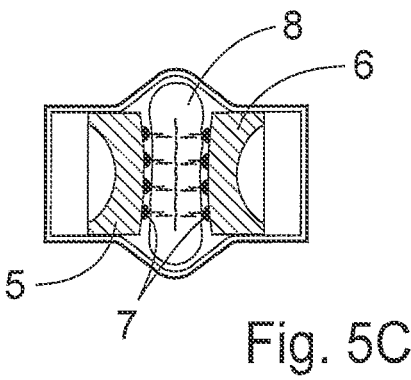

FIGS. 5A-5C illustrate in principle the function of the apparatus of FIG. 2 when the apparatus is applied on a portion 8 of a tubular uterine tube wall of a patient's uterine tube. Thus, FIG. 5A shows the apparatus in a non-clamping state, in which the clamping elements 5, 6 are in their retracted positions and the wall portion 8 extends through the open ends of the housing 1 without being constricted by the clamping elements 5, 6. FIG. 5B shows the apparatus in a clamping state, in which the clamping elements 5, 6 have been moved from their retracted positions to their clamping positions, in which the clamping elements 5, 6 gently constrict the wall portion 8 to a constricted state, in which the blood circulation in the constricted wall portion 8 is substantially unrestricted and the flow in the uterine tube of the wall portion 8 is restricted. FIG. 5C shows the apparatus in a stimulation state, in which the clamping elements 5, 6 constrict the wall portion 8 and the electrical elements 7 of the stimulation device 3 electrically stimulate different areas of the wall portion 8, so that the wall portion 8 contracts (thickens) and closes the uterine tube.

When the apparatus is in its stimulation state, it is important to stimulate the different areas of the wall portion 8 in a manner so that they essentially maintains their natural physical properties over time to prevent the areas from being injured. Consequently, the control device 4 controls the stimulation device 3 to intermittently stimulate each area of the wall portion 8 during successive time periods, wherein each time period is short enough to maintain over time satisfactory blood circulation in the area. Furthermore, the control device 4 controls the stimulation of the areas of the wall portion 8, so that each area that currently is not stimulated restores substantially normal blood circulation before it is stimulated again. To maintain over time the effect of stimulation, i.e., to keep the uterine tube closed by maintaining the wall portion 8 contracted, the control device 4 controls the stimulation device 3 to stimulate one or more of the areas at a time and to shift the stimulation from one area to another over time. The control device 4 may control the stimulation device 3 to cyclically propagate the stimulation of the areas along the tubular wall portion 8, for example, in accordance with a determined stimulation pattern. To achieve the desired reaction of the uterine tube wall during the stimulation thereof, the control device may control the stimulation device to, preferably cyclically, vary the intensity of the stimulation of the wall portion 8.

In the embodiment of FIGS. 2-4, the electrical elements 7 form a series of fourteen groups of electrical elements 7 extending longitudinally along each elongate clamping element 5 and 6, respectively, see FIG. 2. The electrical elements 7 of each group of electrical elements 7 form a first path of four electrical elements 7 positioned in a row on clamping element 5 and extending tranverse thereto, and a second path of four electrical elements 7 positioned in a row on clamping element 6 and extending tranverse thereto. Thus, the two paths of electrical elements 7 extend on mutual sides of the patient's uterine tube. The control device 4 controls the stimulation device 3 to successively energize the groups of electrical elements 7 in the series of groups in a direction opposite to or, alternatively, in the same direction as that of the flow in the uterine tube of the patient's uterine tube. Of course, the number of electrical elements 7 of each path of electrical elements 7 can be greater or smaller than four, and several parallel rows electrical elements 7 can form each path of electrical elements 7.

Figure 6A:
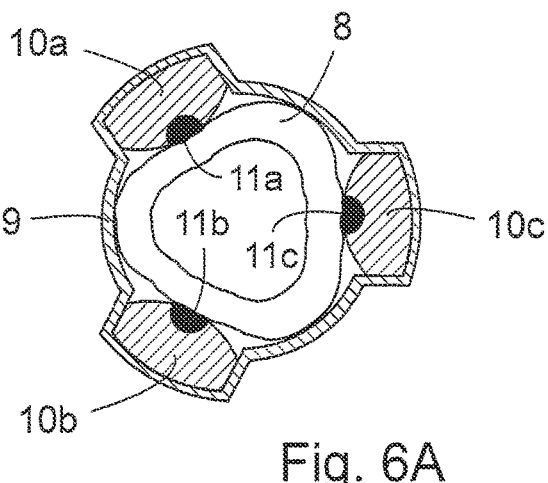
FIGS. 6A, 6B and 6C are cross-sections of a modification of the embodiment of FIG. 2 showing different states of operations with the apparatus applied on a uterine tube wall of a patient's uterine tube.
Figure 6B:
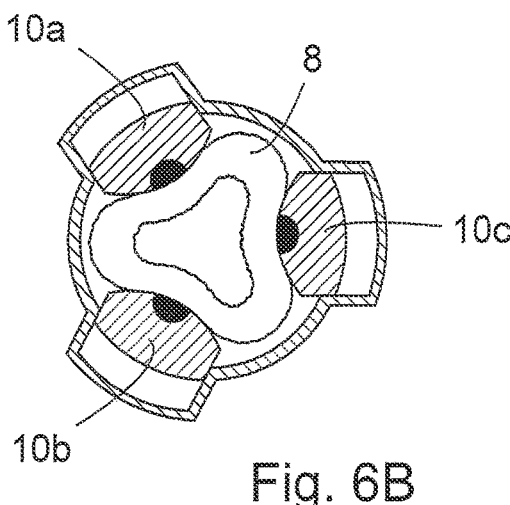
Figure 6C:
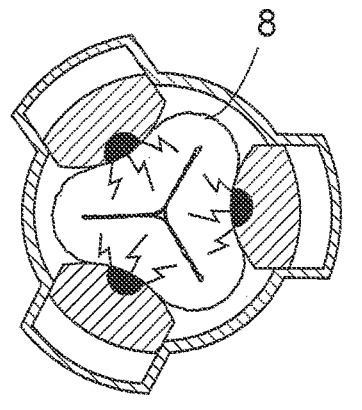

FIGS. 6A-6C show another embodiment of the invention which includes a tubular housing 9 and three elongate clamping elements 10a, 10b, 10c, which are radially movable in the tubular housing 9 towards and away from a central axis thereof between retracted positions, see FIG. 6A, and clamping positions, see FIG. 6B. The three clamping elements 10a-10c are symmetrically disposed around the central axis of the housing 9. The stimulation device of this embodiment includes electrical elements 11a, 11b, 11c that form a series of groups of elements extending longitudinally along the elongate clamping elements 10a-10c, wherein the electrical elements 11a-11c of each group of electrical elements form a path of three electrical elements 11a, 11b and 11c extending circumferentially around the central axis of the housing 9. The three electrical elements 11a-11c of each group are positioned on the three clamping elements 10a-10c, respectively. Thus, the path of three electrical elements 11a-11c extends around the patient's uterine tube. Of course, the number of electrical elements 11a-11c of each path of electrical elements can be greater than three, and several parallel rows electrical elements 11a-11c can form each path of electrical elements.

FIGS. 7A and 7B show different steps of an electric stimulation mode performed by the apparatus of FIG. 2 while the clamping elements 5, 6 of the apparatus are constricting a portion of a tubular uterine tube wall of a patient's uterine tube 12 to restrict the flow in the uterine tube 13 of the organ 12. For the sake of clarity only the clamping elements 5, 6 of the constriction device 2 are shown in FIGS. 7A, 7B. Thus, FIG. 7A illustrates how energized electrical elements 7 of groups of electrical elements electrically stimulate a first portion 14 and a second portion 15 of the tubular wall to contract and close the uterine tube 13. FIG. 7B illustrates how energized electrical elements 7 of other groups of electrical elements electrically stimulate a third portion 16 of the tubular wall different from the first and second portions to contract and close the uterine tube 13, while the electrical stimulation of the first and second portions 14, 15 of the tubular wall has been ceased, so that substantially normal blood circulation in the first and second portions is restored. In this manner, the electric stimulation of the constricted tubular wall is shifted over time from one portion of the tubular wall to another to insure recurrent restoration of blood circulation in the constricted tubular wall.

The control device 4 controls the stimulation device 3 to energize the electrical elements 7 with electric biphasic pulses, i.e., combined positive and negative pulses. The desired stimulation effect is achieved by varying different pulse parameters. Thus, the control device 4 controls the stimulation device 3 to vary the pulse amplitude (voltage), the off time period between successive pulses, the pulse duration and the pulse repetition frequency. The pulse current should be between 1 to 30 mA. For neural stimulation, a pulse current of about 5 mA and a pulse duration of about 300 μs are suitable, whereas a pulse current of about 20 mA and a pulse duration of about 30 μs are suitable for muscular stimulation. The pulse repetition frequency suitably is about 10 Hz. For example, as illustrated in the Pulse/time diagram P/t of FIG. 8A, a pulse combination including a negative pulse PS of short duration and high amplitude (voltage), and a positive pulse PL of long duration and low amplitude following the negative pulse may be cyclically repeated to form a pulse train of such pulse combinations. The energy content of the negative pulse PS should be substantially equal to the energy content of the positive pulse PL.

Figure 8A:
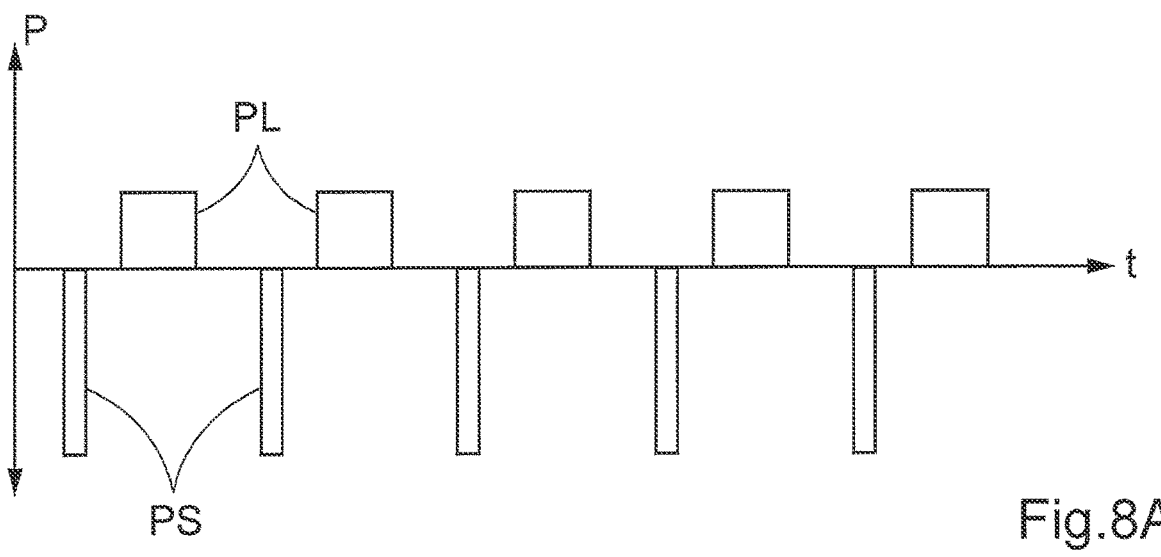
FIG. 8A is a pulse/time diagram showing electric stimulation pulses generated by the apparatus of the invention for stimulating a uterine tube wall of a patient's uterine tube.
Figure 8B:
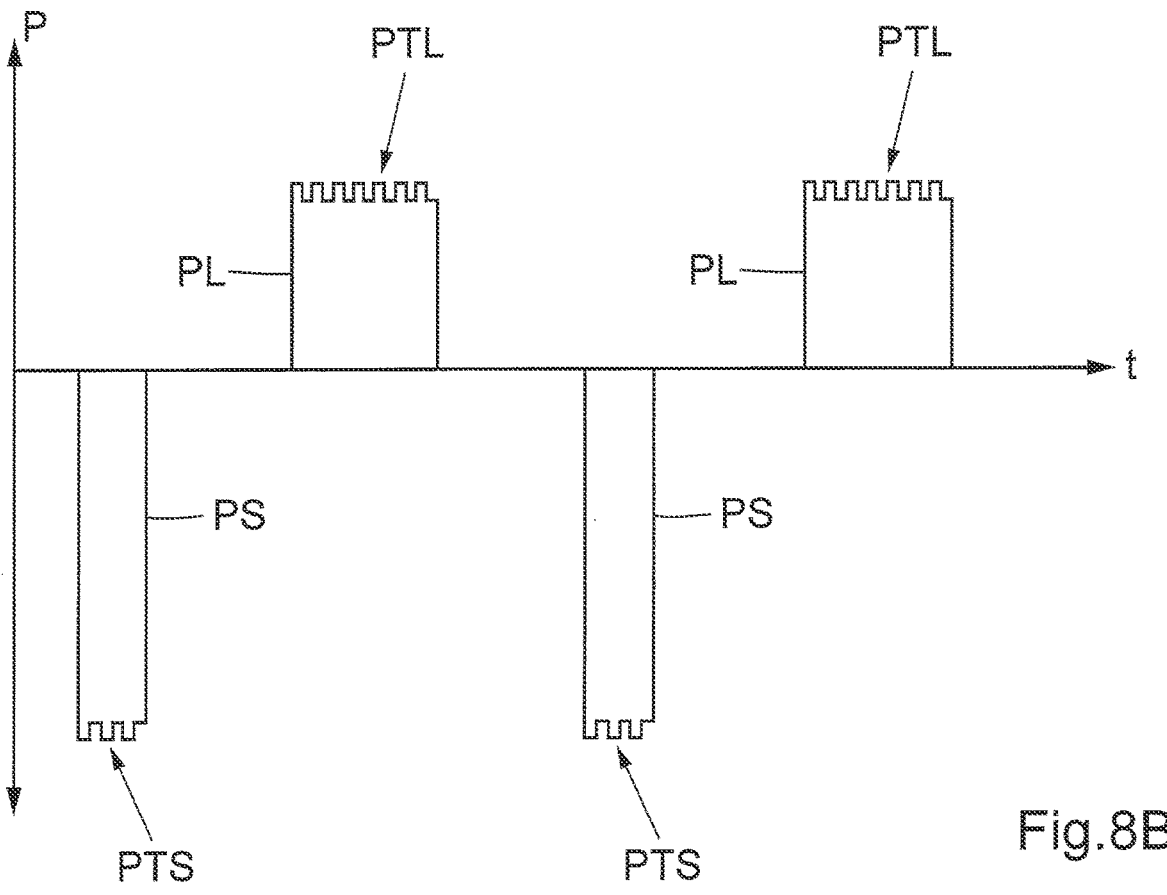
FIG. 8B is pulse/time diagram showing a modification of the electric stimulation shown in FIG. 8A, in which pulses of mixed frequencies and/or amplitudes are employed.

FIG. 8B is a pulse/time diagram showing a modification of the electric stimulation shown in FIG. 8A. Thus, the pulse combination of FIG. 8A is mixed with a pulse train combination having a first relatively long pulse train PTL of high frequency/low amplitude pulses, appearing simultaneously with the positive pulse PL of the pulse combination of FIG. 8A, and a second relatively short pulse train PTS of high frequency/low amplitude appearing simultaneously with the negative pulse PS of the pulse combination shown in FIG. 8A. As a result, the high frequency/low amplitudes pulse trains PTL and PTS are superimposed on the positive and negative pulses PL and PS of FIG. 8A, as illustrated in FIG. 8B. The pulse configuration of FIG. 8B, and variations thereof, is beneficial to use in connection with the stimulation of the uterine tube, in order to achieve the desired stimulation effect.

Figures 9A, 9B:
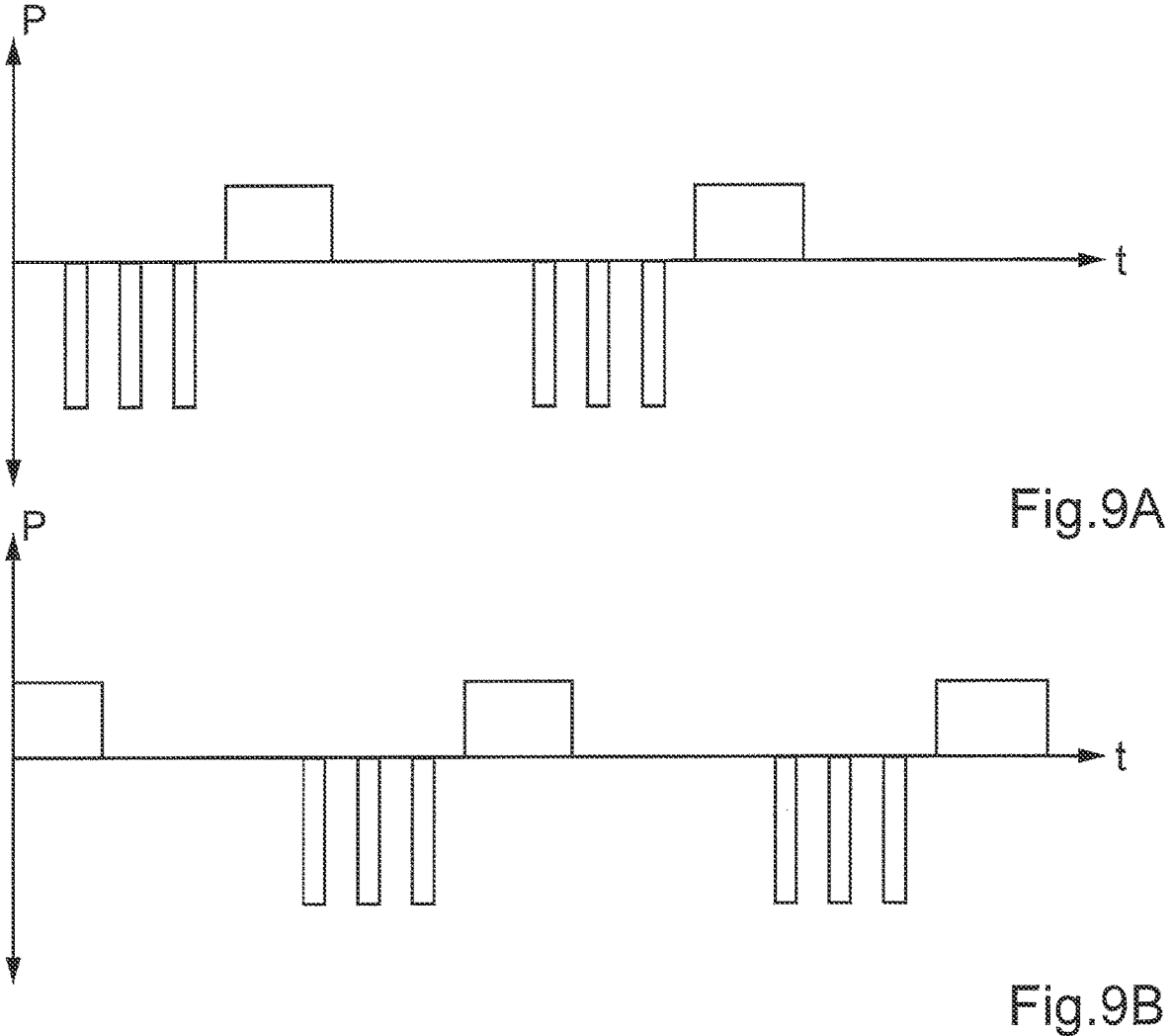
FIGS. 9A and 9B show two pulse/time diagrams, respectively, representing electric stimulation of two different areas of the uterine tube wall with pulses forming pulse trains.

Preferably, the electric pulses form pulse trains, as illustrated in the Pulse/time diagrams P/t of FIGS. 9A, 9B, 9C and 9D. The Pulse/time diagram P/t of FIG. 9A represents an individual area of the wall portion of the patient's uterine tube which is stimulated with a pulse train 18A. The pulse train 18A includes three initial negative pulses, each of which is of short duration and high amplitude (voltage), and one positive pulse of long duration and low amplitude following the negative pulses. After a delay to enable the area of the uterine tube to restore substantially normal blood circulation, the pulse train 18A is repeated.

The Pulse/time diagram P/t of FIG. 9B represents another individual area of the wall portion, which is stimulated with a pulse train 18B having the same configuration as the pulse train 18A. The pulse trains 18A and 18B are shifted relative to each other, so that they partially overlap one another to ensure that the constricted wall portion always is stimulated to contract as desired.

Figures 10A, 10B:
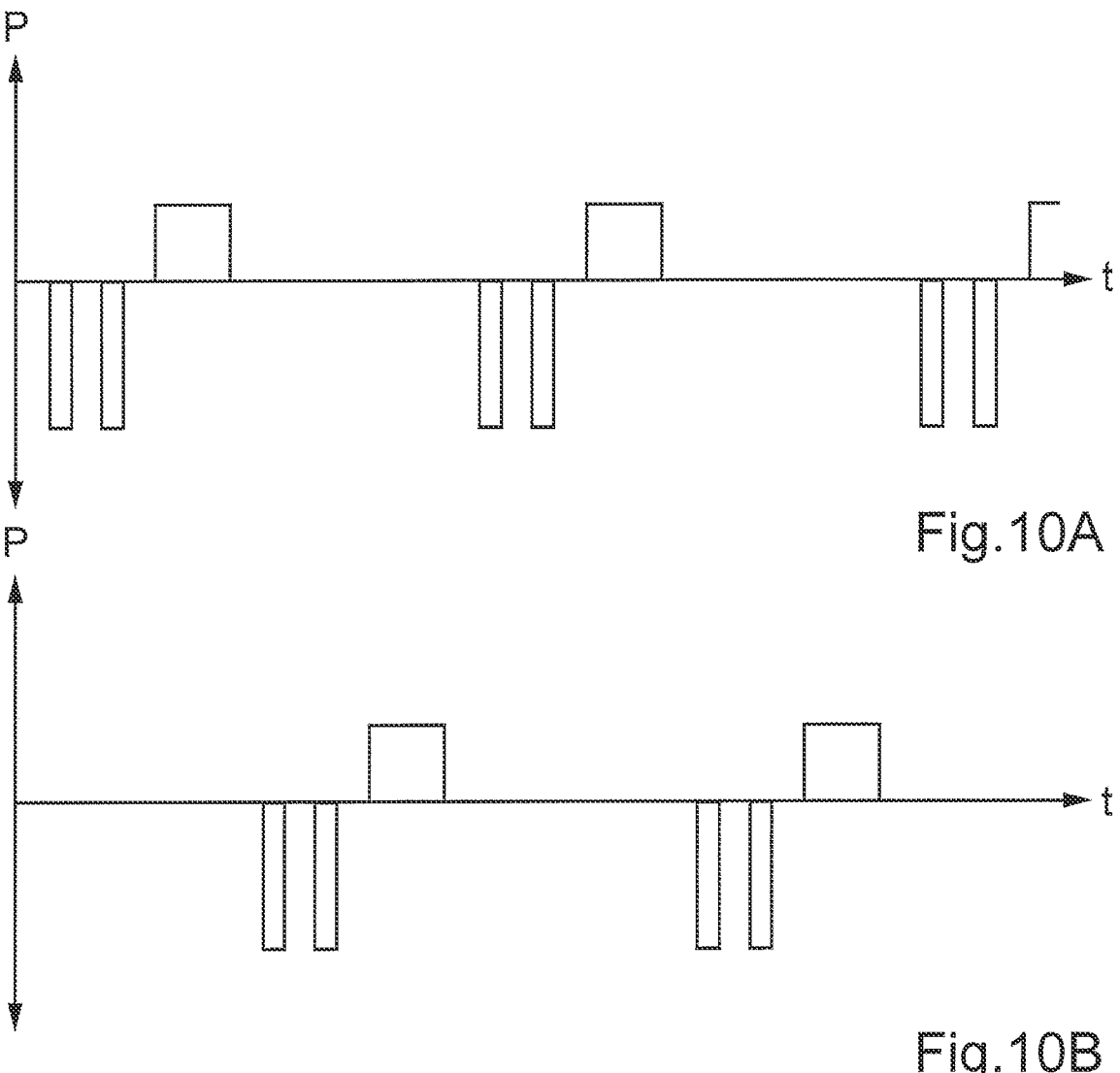
FIGS. 10A and 10B show the pulse/time diagrams of FIGS. 9A and 9B with modified pulse trains.

The pulse/time diagrams P/t of FIGS. 10A and 10B represent two different areas of the wall portion, which are stimulated with cyclically repeated pulse trains 18C and 18D, respectively, having the same configuration. Each pulse train 18C, 18D includes two initial negative pulses, each of which is of short duration and high amplitude (voltage), and one positive pulse of long duration and low amplitude following the two negative pulses. In this case, the pulse trains 18C and 18D are shifted relative to each other, so that they do not overlap each other. Thus, the off time period between adjacent pulse trains 18C is longer than the duration of pulse train 18D and the off time period between adjacent pulse trains 18D is longer than the duration of pulse train 18C.

The pulse trains 18A, 18B, 18C and 18D can be configured in many different ways. Thus, the control device 4 can control the stimulation device 2 to vary the length of each pulse train, the repetition frequency of the pulse trains, the number of pulses of each pulse train, and/or the off time periods between the pulse trains. Typically, the control device 4 controls each off time period between the pulse trains to last long enough to restore substantially normal blood circulation in the area that just has been stimulated before that area again is stimulated with electric pulses.

Figure 11B:
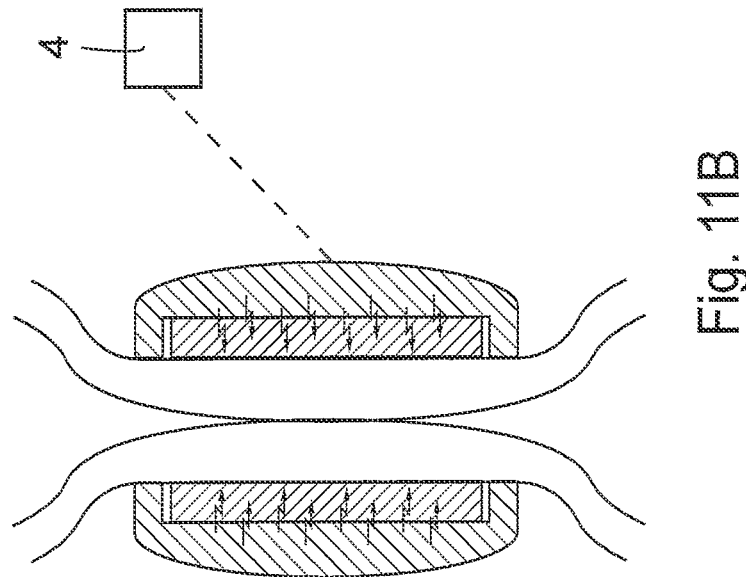
FIG. 11B is the same embodiment of FIG. 11A with the thermal stimulation device activated.
Figure 11A:
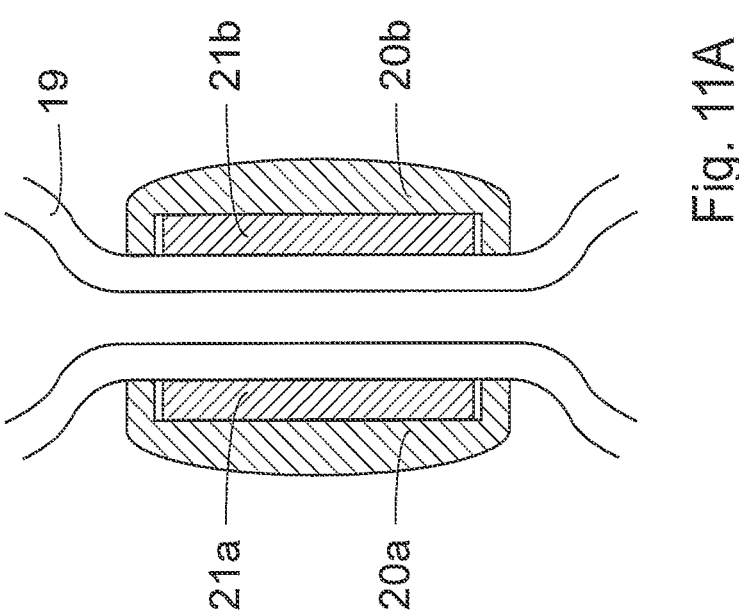
FIG. 11A is a longitudinal cross-section of an embodiment of the apparatus of the invention including a thermal stimulation device, wherein the apparatus is constricting a uterine tube wall of a patient's uterine tube.

FIGS. 11A and 11B show another embodiment of the invention that controls sperm flow in a uterine tube 19, comprising a constriction device with two clamping elements 20a and 20b, a stimulation device in the form of two thermal stimulation elements 21a and 21b integrated in the clamping elements 20a, 20b, respectively, and a control device 4 for controlling the clamping elements 20a, 20b and stimulation elements 21a, 21b. The clamping elements 20a and 20b are movable towards and away from each other in the same manner as described above in connection with the embodiment according to FIGS. 5A-5C. The thermal stimulation elements 21a and 21b, which may include Pertier elements, are positioned on the clamping elements 20a, 20b, so that the thermal elements 21a are facing the thermal elements 21b. FIG. 11A shows how the clamping elements 20a, 20b constrict the uterine tube 19, so that the sperm flow is restricted. FIG. 11B shows how the control device 4 controls the thermal stimulation elements 21a, 21b to cool the wall of the uterine tube 19, so that the wall contracts and closes the uterine tube 19. To release the uterine tube 19, the control device 4 controls the thermal stimulation elements 21a, 21b to heat the wall of the uterine tube 19, so that the wall expands.

Figure 12A:
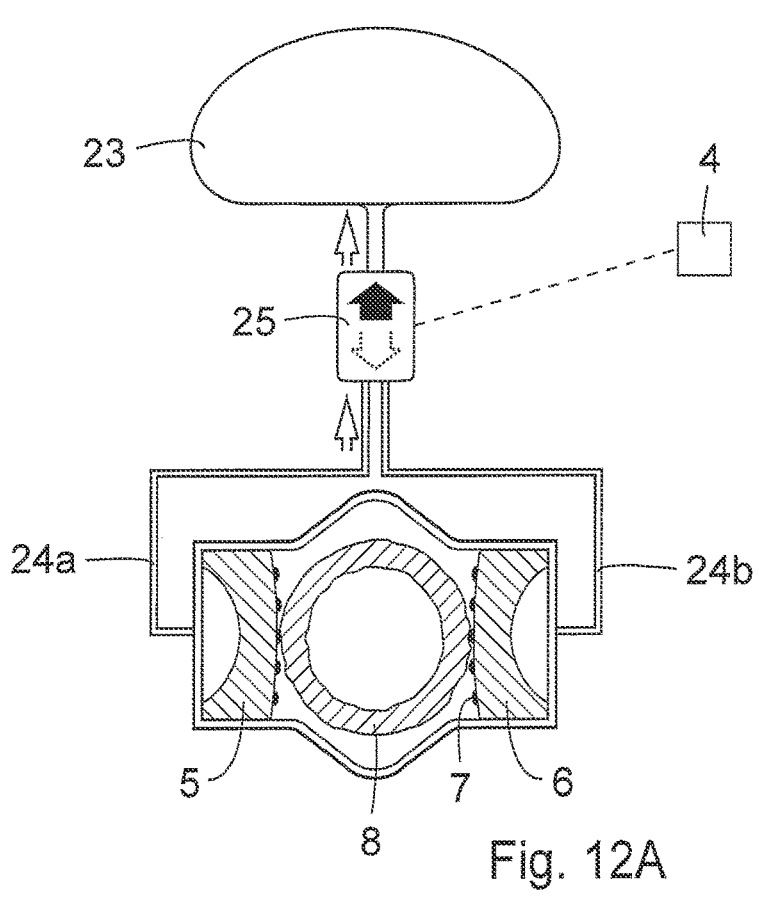
FIG. 12A is a schematic view of hydraulic operation means suited for operating the constriction device of the embodiments of FIGS. 2-11.
Figure 12B:
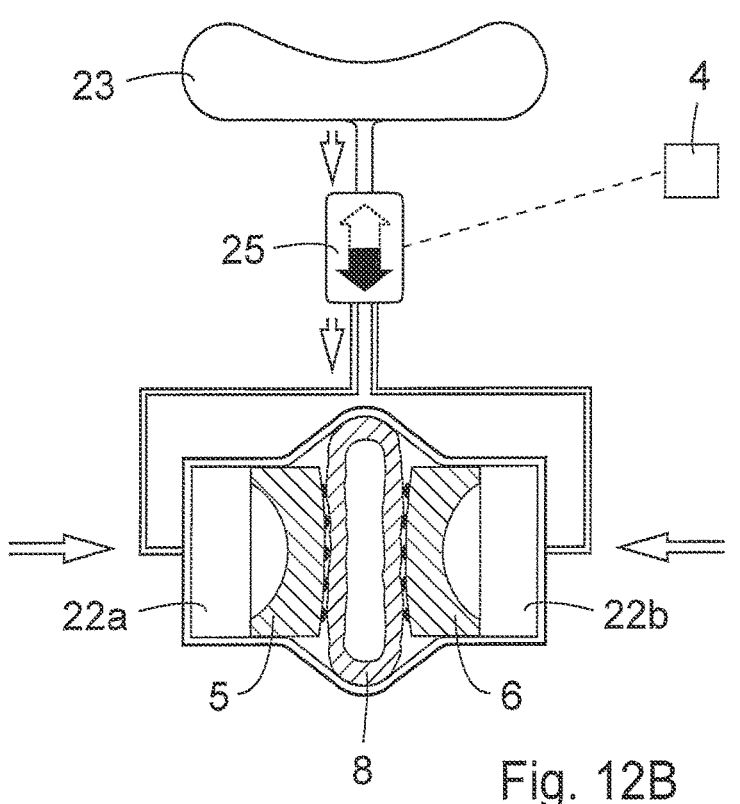
FIG. 12B shows the embodiment of FIG. 12A with the constriction device constricting a uterine tube wall of a patient's uterine tube.

FIGS. 12A and 12B show hydraulic operation means suited for operating the constriction device of the embodiments described above. Specifically, FIGS. 12A and 12B show the apparatus of FIG. 2 provided with such means for hydraulic operation of the constriction device 2. (The stimulation device is not shown.) Thus, the housing 1 forms two hydraulic chambers 22a and 22b, in which the two clamping elements 5, 6 are slidable back and forth relative to the tubular uterine tube wall portion 8 of a patient's uterine tubes. The hydraulic operation means include an expandable reservoir 23, such as an elastic balloon, containing hydraulic fluid, conduits 24a and 24b between the reservoir 23 and the hydraulic chambers 22a, 22b, and a two-way pump 25 for pumping the hydraulic fluid in the conduits 24a, 24b. The control device 4 controls the pump 25 to pump hydraulic fluid from the reservoir 23 to the chambers 22a, 22b to move the clamping elements 5, 6 against the wall portion 8, whereby the wall portion 8 is constricted, see FIG. 12B, and to pump hydraulic fluid from the chambers 22a, 22b to the reservoir 23 to move the clamping elements 5, 6 away from the wall portion 8, whereby the tubular wall 8 is released, see FIG. 12A.

Alternatively, the embodiment of FIGS. 12A and 12B may be manually operated by applying suitable manually operable hydraulic means for distributing the hydraulic fluid between the expandable reservoir 23 and the hydraulic chambers 22a, 22b. In this case the pump 25 is omitted.

Figure 13A:
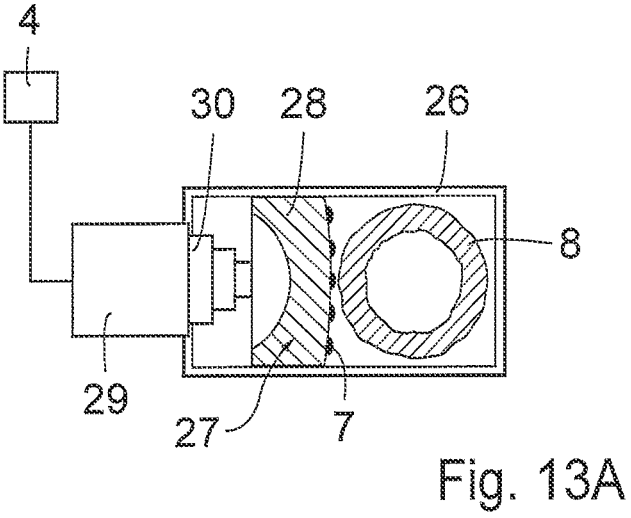
FIG. 13A is a schematic view of mechanical operation means suited for operating the constriction device of the embodiments of FIGS. 2-11.
Figure 13B:
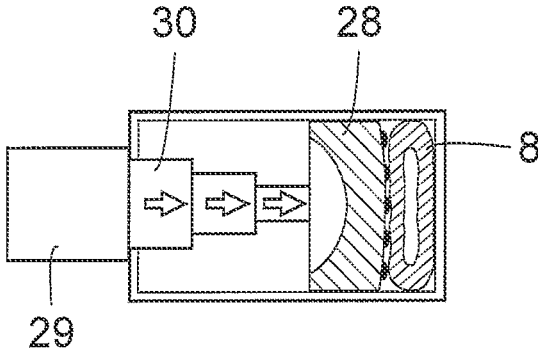
FIG. 13B shows the embodiment of FIG. 13A with the constriction device constricting a uterine tube wall of a patient's uterine tube.

FIGS. 13A and 13B schematically show a mechanically operable embodiment of the invention, comprising an open ended tubular housing 26 applied on the tubular uterine tube wall portion 8 of a patient's uterine tube, a constriction device 27 arranged in the housing 26 and a control device 4 for controlling the constriction device 27. A stimulation device (not shown) as described above is also provided in the housing 26. The constriction device 27 includes a clamping element 28, which is radially movable in the tubular housing 26 towards and away from the tubular wall portion 8 between a retracted position, see FIG. 13A, and a clamping position, see FIG. 13B, in which the clamping element 28 gently constricts the tubular wall portion 8. Mechanical operation means for mechanically operating the clamping element 28 includes an electric motor 29 attached to the housing 26 and a telescopic device 30, which is driven by the motor 29 and operatively connected to the clamping element 28. The control device 4 controls the electric motor 29 to expand the telescopic device 30 to move the clamping element 28 against the wall portion 8, whereby the tubular wall portion 8 is constricted, see FIG. 13B, and controls the motor 29 to retract the telescopic device 30 to move the clamping element 28 away from the wall portion 8, whereby the wall portion 8 is released, see FIG. 13A.

Figure 13C:
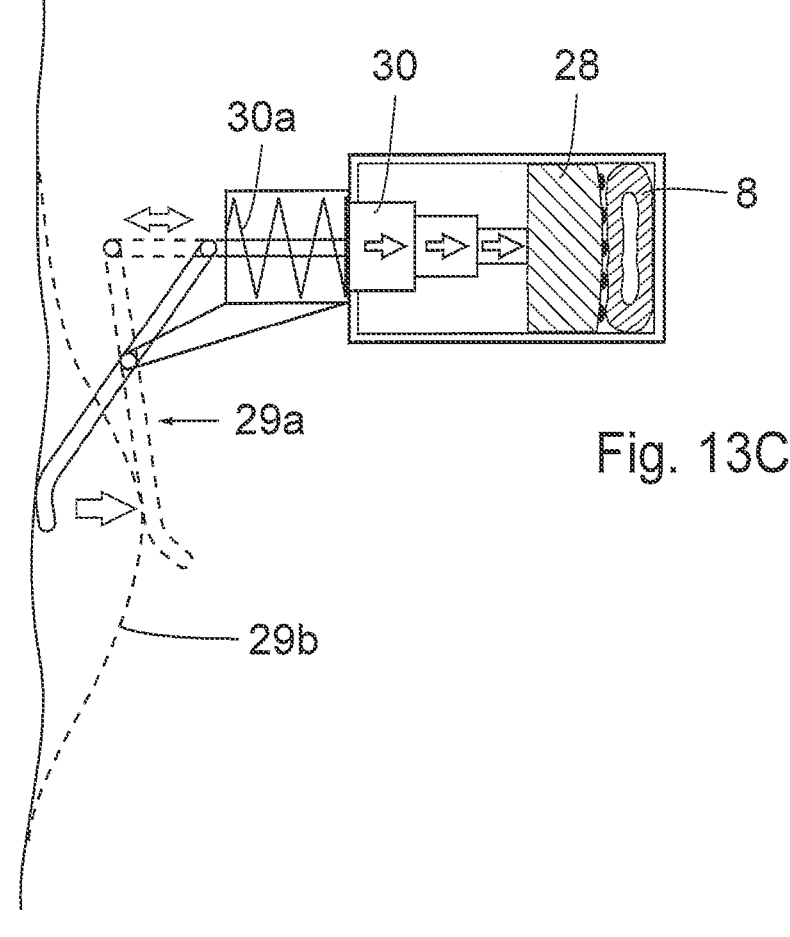
FIG. 13C shows a modification of the embodiment of FIG. 13B.

Alternatively, the motor 29 may be omitted and the telescopic device 30 be modified for manual operation, as shown in FIG. 13C. Thus, a spring 30a may be provided acting to keep the telescopic device 30 expanded to force the clamping element 28 against the wall portion 8. The mechanical operation means may include a subcutaneously implanted lever mechanism 29a that is operatively connected to the telescopic device 30. The patient may push the lever mechanism 29a through the patient's skin 29b to pull the telescopic device 30 against the action of the spring 30a to the retracted position of the telescopic device 30, as indicated in phantom lines. When the patient releases the lever mechanism 29a, the spring 30a expands the telescopic device 30, whereby clamping element 28 is forced against the wall portion 8.

The mechanical operation means as described above in connection with FIGS. 13A, 13B and 13C may also be implemented in the embodiments according to FIGS. 1-11.

Figure 14:
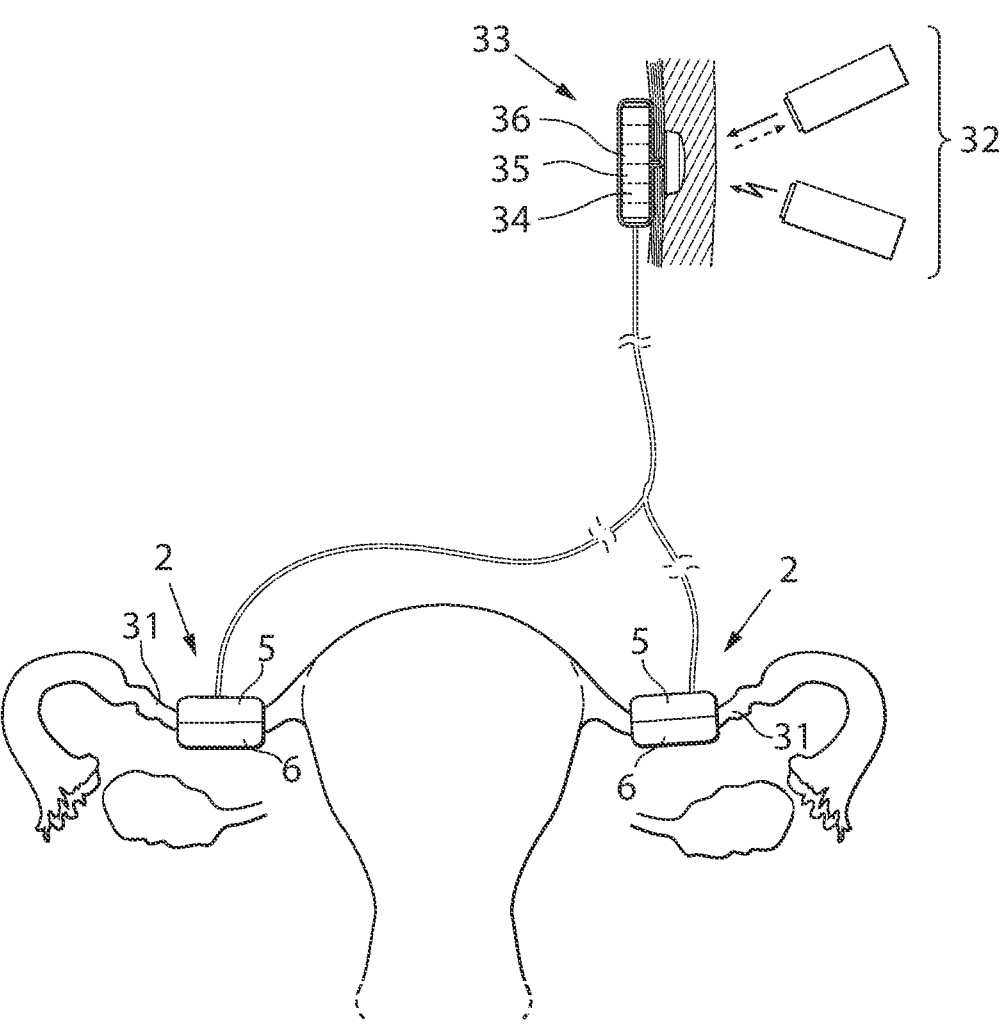
FIG. 14 illustrates the embodiment of FIG. 2 applied on the uterine tube of a patient.

FIG. 14 illustrates the embodiment of FIG. 2 applied on the uterine tube of a patient. The clamping elements 5, 6 of the constriction device 2 constrict the uterine tubes 31 and the stimulation device 3 is energized to close the uterine tube. (For the sake of clarity, the housing is not shown and the clamping elements 5, 6 are exaggerated.) In this embodiment, a control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the constriction device and/or the stimulation device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, also works as en energy receiver, i.e., for transforming wireless energy into electric energy and charging the implanted source of energy 35 (rechargeable battery) with the electric energy.

An implanted sensor 36 senses a physical parameter of the patient, such as the pressure in the uterine tubes, or a parameter that relates to the pressure in the uterine tubes, wherein the internal control unit 33 controls the constriction device 2 and/or the stimulation device 3 in response to signals from the sensor 36. In this embodiment the sensor 36 is a pressure sensor, wherein the internal control unit 33 controls the constriction device and/or stimulation device to change the constriction of the patient's intestines 31 in response to the pressure sensor 36 sensing a predetermined value of measured pressure. For example, the control unit 33 may control the constriction device and/or stimulation device to increase the constriction of the patient's uterine tubes 31 in response to the pressure sensor sensing an increased pressure. Alternatively or in combination, the remote control 32 controls the constriction device and/or stimulation device in response to signals from the sensor 36, in the same manner as the internal control unit 33.

The remote control 32 may be equipped with means for producing an indication, such as a sound signal or displayed information, in response to signals from the sensor 36. When the patient's attention is taken by such an indication indicating an increased pressure exceeding a threshold value, he or she may use the remote control to control the constriction device and stimulation device to pump sperms through the patient's uterine tubes towards the ovary. If pregnacy wants to be achieved or pump in the opposite direction to avoid pregnancy.

Of course, the constriction device 2 shown in FIG. 14 may be replaced by any one of the constriction devices described in the various embodiments of the present invention, where applicable.

Figure 15:
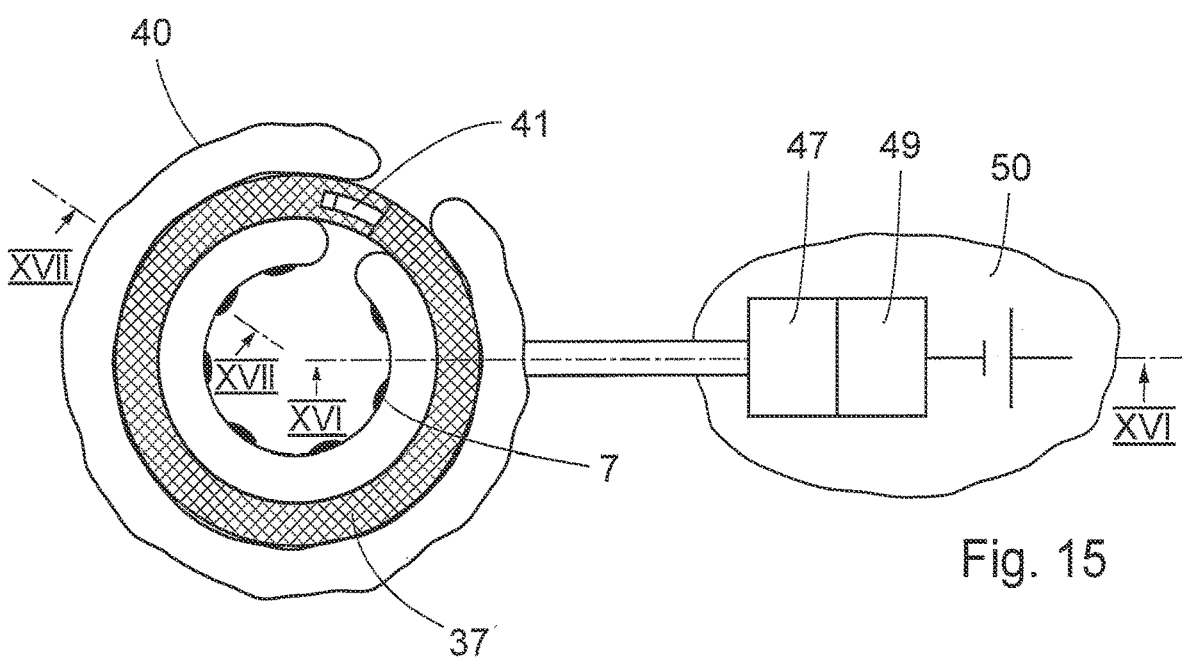
FIG. 15 is a schematic sectional view of a mechanically operable non-inflatable constriction device for use in accordance with the invention.
Figure 16:
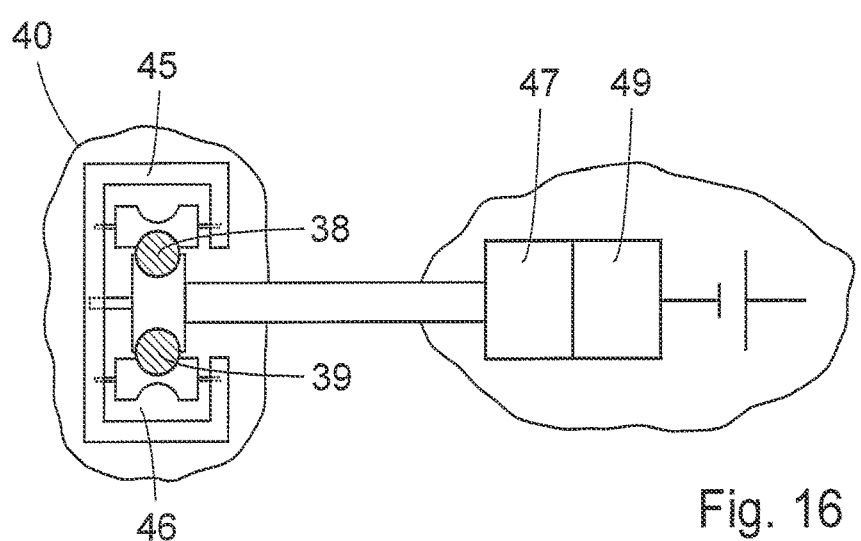
FIGS. 16 and 17 are cross-sectional views taken along the lines XVI-XVI and XVII-XVII, respectively, of FIG. 15.
Figure 17:
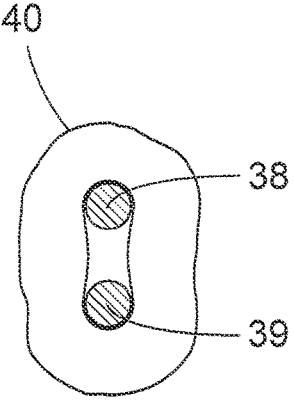

FIGS. 15-17 show a mechanically operable constriction device having an elongated constriction member in the form of a circular resilient core 37 with two overlapping end portions 38, 39. The core 37 defines a substantially circular restriction opening and is enclosed in an elastic soft hose 40 except at a releasable and lockable joint 41 of the core 37, which when released enables application of the core 37 with its hose 40 around a portion of a tubular uterine tube wall of a patient's uterine tubes. The materials of all of these elements are bio-compatible so that the patient' body will not reject them. An operation device 42 for mechanically operating the longitudinal extension of the core 37 to change the size of the restriction opening comprises a drive wheel 43 in frictional engagement with the overlapping end portions 38, 39 of the core 37. The drive wheel 43 is journalled on a holder 44 placed in the hose 40 and provided with two counter pressure rollers 45, 46 pressing the respective end portions 38, 39 of the core 37 against the drive wheel 43 to increase the frictional engagement there between. An electric motor 47 of the operation device is connected to the drive wheel 43 via a long flexible drive shaft 48, and is moulded together with a remote controlled power supply unit 49 in a body 50 of silicone rubber. The length of the flexible drive shaft 48 is selected so that the body 50 can be placed in a desired position in the patient's body, suitably in the abdomen.

The power supply unit 49 can be controlled to power the electric motor 47 to turn the drive wheel 43 in one direction to reduce the diameter of the core 37, so that the wall portion is constricted, or to turn the drive wheel 43 in the opposite direction to increase the diameter of the core 37, so that the wall portion is released.

In accordance with a first alternative, a rack gear may be formed on one of the end portions 38, 39 of the core 37 and the drive wheel 43 may be replaced by a drive gear wheel connected to the other end portion of the core 37 and in mesh with the rack gear.

In accordance with a second alternative, the operation device 42 may be designed as a worm-driven hose clamp, i.e., one of the end portions 38, 39 of the core 37 may be provided with threads and the other end portion of the core 37 may be provided with a worm, the threads of which interacts with the threads of said one end portion of the core 37. The threads of such a worm may also interact with threads provided on both end portions 38, 39 of the core 37. In this alternative, the electric motor 47 turns the worm in one direction to reduce the diameter of the core 37, so that the wall portion is constricted, or turn the worm in the opposite direction to increase the diameter of the core 37, so that the wall portion is released in one direction to reduce the diameter of the core 37, so that the wall portion is constricted, or turns the clamping screw in the opposite direction to increase the diameter of the core 37, so that the wall portion is released.

Figure 18:
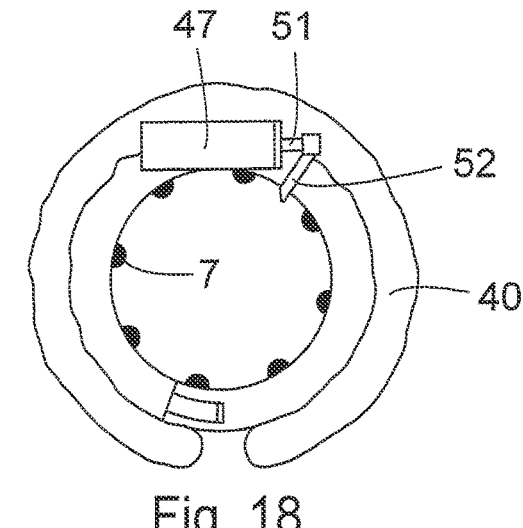
FIG. 18 schematically shows an alternative design of the embodiment of FIG. 15.

FIG. 18 shows a constriction device which is identical to the embodiment of FIGS. 15-17, except that the motor 47 is encapsulated in the hose so that it is fixed to the core 37 and has a short drive shaft 51, and that the motor 47 is positioned relative to the core 37, such that the drive shaft 51 extends substantially tangentially to the circular core 37. There is an angular gearing 52 connecting the drive shaft 51 to the drive wheel 43.

Figure 19:
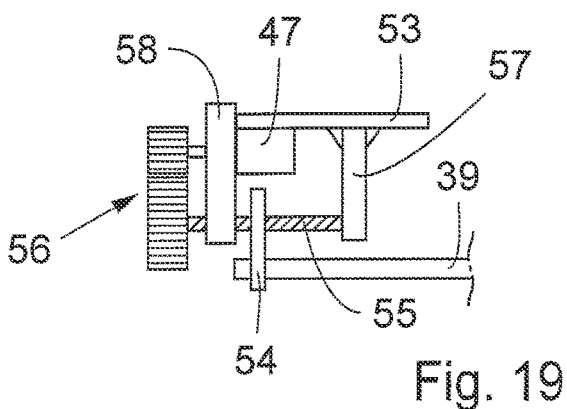
FIG. 19 schematically illustrates a motor arrangement for the design according to FIG. 18.

FIG. 19 shows a suitable alternative arrangement for the motor 47 in the embodiment of FIG. 18, comprising a first clamping member 53 secured to one end portion of the core 37 and a second clamping member 54 secured to the other end portion 39 of the core 37. The motor 47 is secured to the first clamping member 53 and is operatively connected to a worm gear 55 via a gear transmission 56. The worm gear is journalled at its opposite ends on holders 57 and 58, which are rigidly secured to the clamping member 53 and the motor 47, respectively. The second clamping member 54 has a pinion in mesh with the worm gear 55. When the motor 47 is powered, the worm gear 55 rotates, and will thereby pull the end portion 39 of the core 37 in one or the opposite longitudinal direction, so that the diameter of the substantially circular core 37 is either increased or decreased. The motor 47, worm gear 55, gear transmission 56 and second clamping member 54 constitute a servo system of the type that transfers a weak force acting on a moving element having a long stroke into a strong force acting on another moving element having a short stroke.

Figure 20:
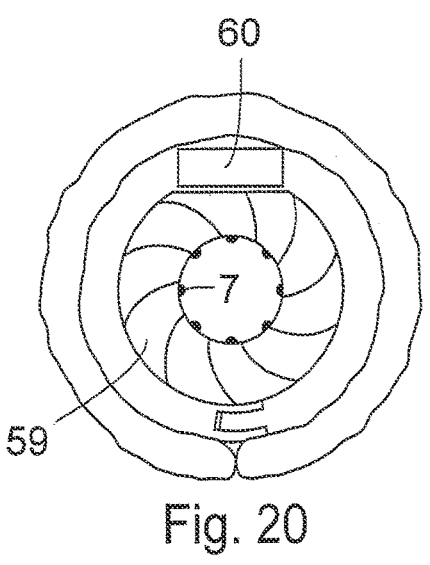
FIGS. 20 and 21 are schematic sectional views of two alternative designs of non-inflatable constriction devices of the invention.

FIG. 20 shows a constriction device including a plurality of arcuate lamellae 59 arranged like the conventional adjustable aperture mechanism of a camera. A motor 60 operates the lamellae 59 to change the size of a restriction opening defined by the lamellae 59.

Figure 21:
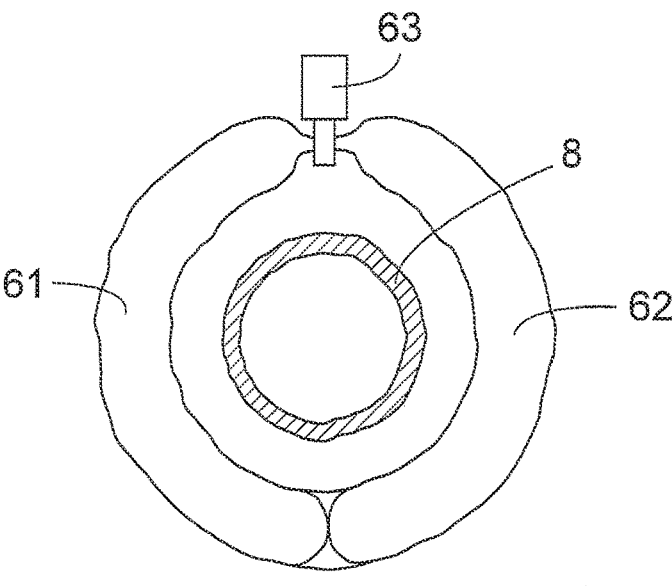
Figure 22:
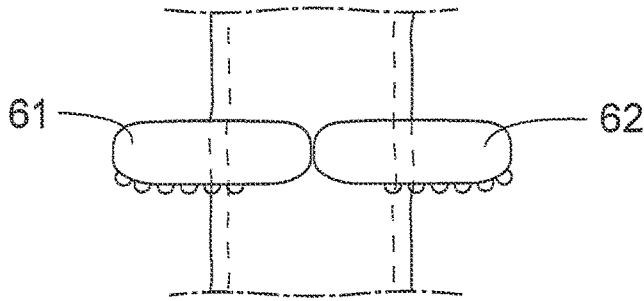
FIGS. 22 and 23 illustrate a fully open and a reduced constriction opening, respectively, of the embodiment of FIG. 21.
Figure 23:
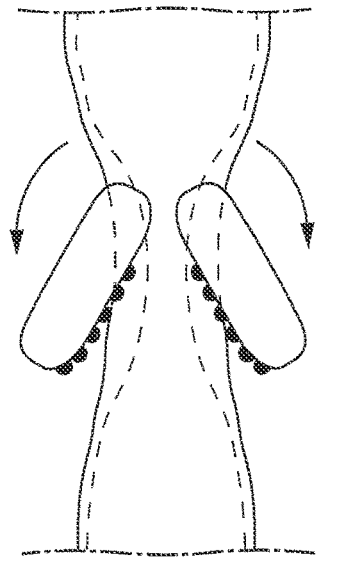

FIGS. 21-23 show a constriction device including two semi-circular elements 61 and 62, which are hinged together such that the semi-circular elements 61, 62 are swingable relative to each other between a fully open state in which they substantially form a circle, as illustrated in FIG. 22, and an angular state, in which the size of the restriction opening defined by the semi-circular elements 61, 62 is reduced, as illustrated in FIG. 23. A motor 63 operates the semi-circular elements 61, 62 to swing them relative to each other.

Figure 24:
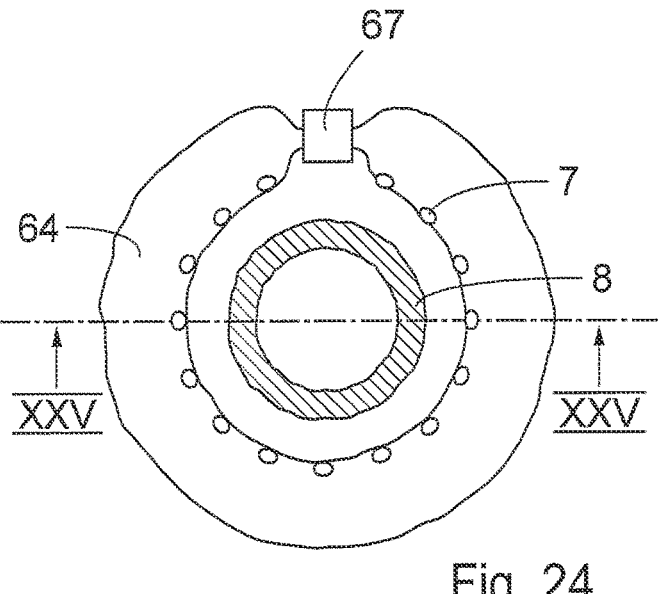
FIG. 24 is a schematic view of a further alternative design of a non-inflatable constriction device of the invention.
Figure 25:
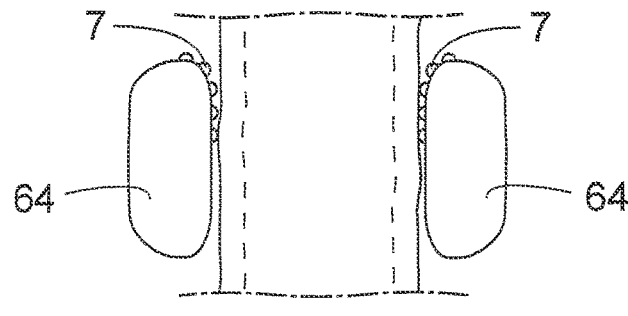
FIGS. 25 and 26 illustrate a fully open and a reduced constriction opening, respectively, of the embodiment of FIG. 24.
Figure 26:
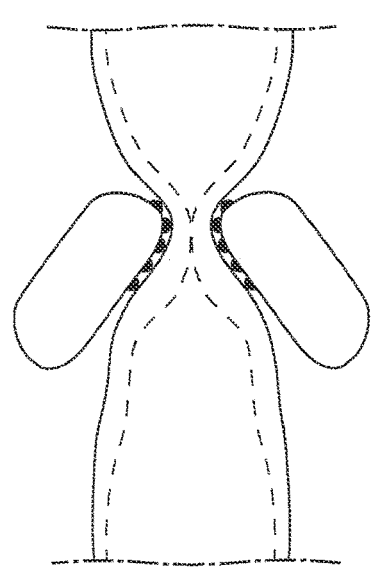

FIGS. 24-26 show a constriction device including an elastic belt 64 forming a circle and having a substantially oval cross-section. A motor 67 operates the belt 64 to turn around the longitudinal extension thereof between a fully open state, in which the inner broader side of the belt 64 forms a substantially cylindrical surface, as illustrated in FIG. 25, and a reduced open state, in which the inner broader side of the belt 64 forms a substantially conical surface, as illustrated in FIG. 26.

Figure 27:
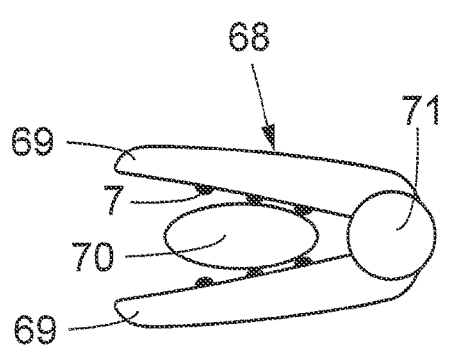
FIG. 27 is a schematic view of another alternative design of a non-inflatable constriction device of the invention.

FIG. 27 shows a constriction device 68 having two rigid articulated clamping elements 69 positioned on opposite sides of a portion of a tubular uterine tube wall 70 of a patient's organ. An operation device 71 turns the clamping elements 69 toward each other to clamp the wall portion 70 between the clamping elements 69 to thereby contract the wall portion, and turns the clamping elements 69 away from each other to release the wall portion from the clamping elements 69.

Figure 28:
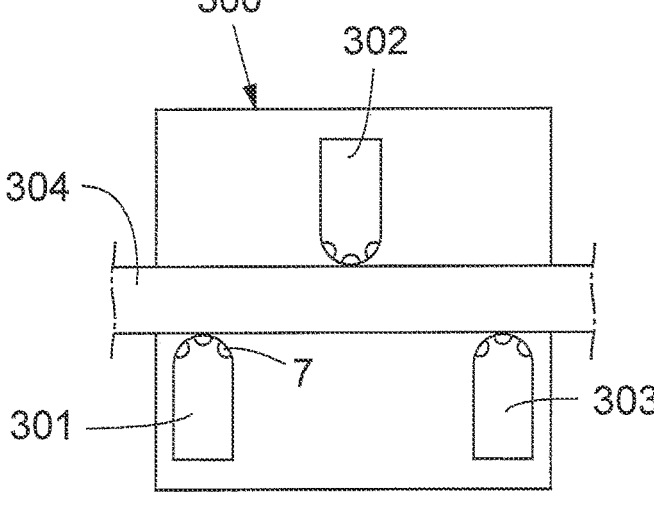
FIGS. 28 and 29 are schematic sectional views, respectively, of yet another alternative design of a non-inflatable constriction device of the invention.
Figure 29:
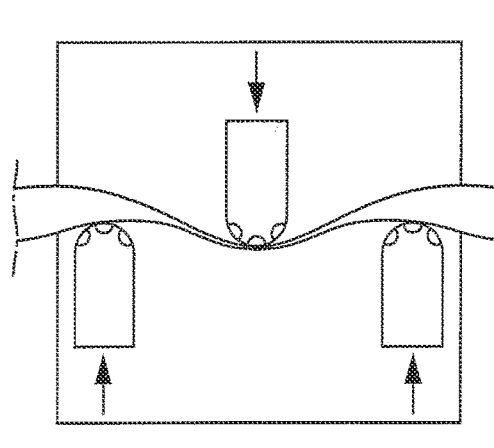

FIGS. 28 and 29 show an embodiment of the apparatus of the invention comprising a constriction device 300 having three bending members 301, 302 and 303 displaced relative to one another in a row along a portion of a tubular uterine tube wall 304 of a patient's uterine tubes and positioned alternately on opposite sides of the tubular wall 304. (Alternatively, each member 301, 302 and 303 may take the shape of an hour-glass.) An operation device (not shown) moves the two outer members 301, 303 laterally against the tubular wall 304 in one direction and the intermediate member 302 against the tubular wall 304 in the opposite direction to bend the tubular wall 304, to thereby constrict the tubular wall portion 304, as illustrated in FIG. 29. To release the wall portion 304 the operation device moves the members 301-303 away from the tubular wall portion 304 to the position shown in FIG. 28.

Figures 30A, 30B, 31A, 31B, 31C, 31D:
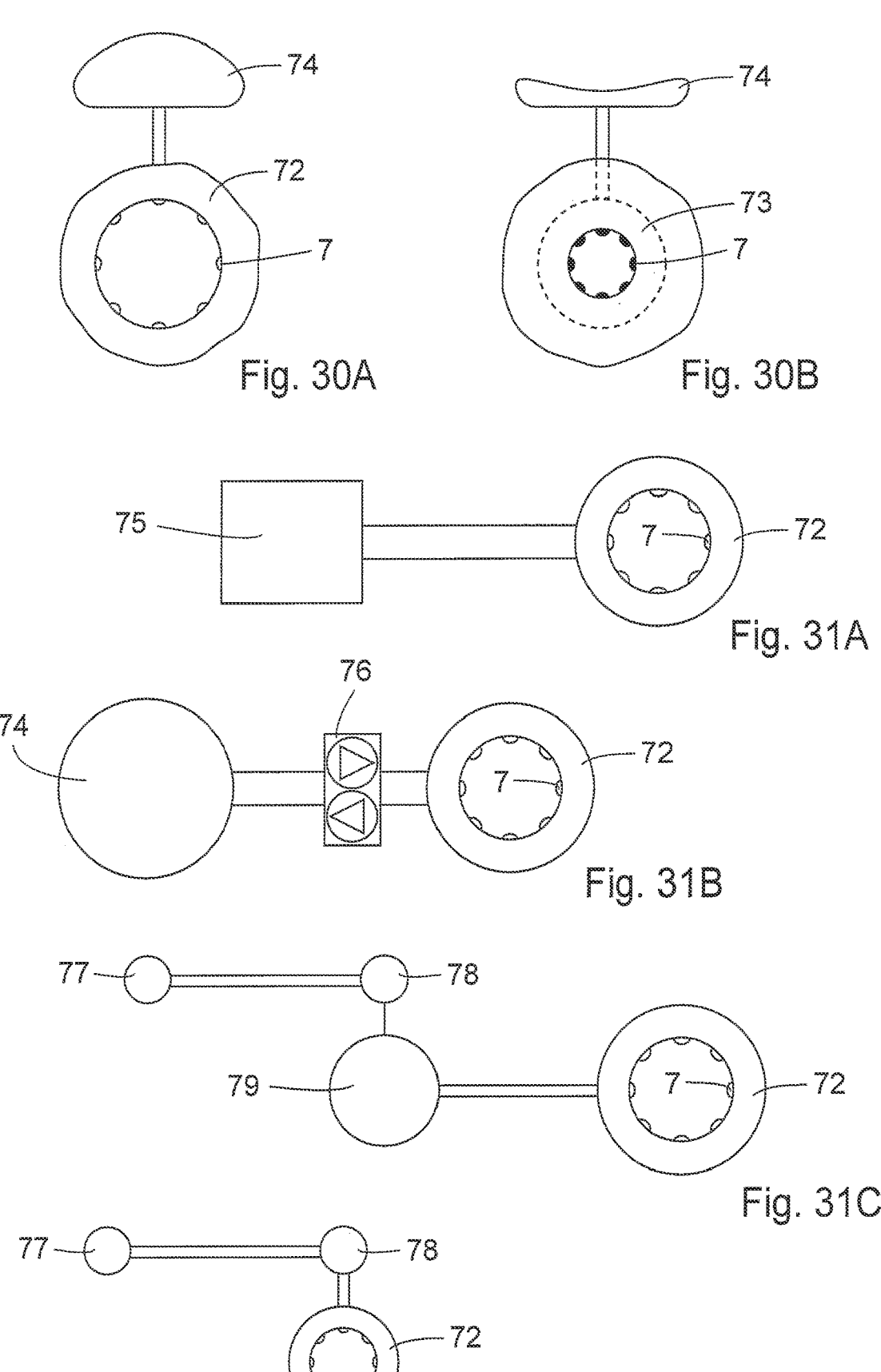
FIG. 30A is a schematic view of a hydraulically operable inflatable constriction device for use in accordance with the invention.
FIG. 30B is the same embodiment shown in FIG. 30A with the constriction device inflated.
FIGS. 31A, 31B, 31C and 31D are block diagrams illustrating four different principles for hydraulic operation of the constriction device shown in FIG. 30A.

FIGS. 30A and 30B show a hydraulically operable elongated constriction device in the form of a band 72 having an expandable/contractible cavity 73, which is in fluid communication with an adjustable reservoir 74 containing hydraulic fluid. FIG. 30A illustrates when the band is in a non-constriction state, whereas FIG. 30B illustrates when the band is in a constriction state, in which the cavity 73 is expanded by hydraulic fluid supplied by the reservoir 74.

FIGS. 31A, 31B, 31C and 31D are block diagrams of four differently operated hydraulic constriction devices. FIG. 31A shows the band 72 of FIG. 30A, the cavity 73 of which is in fluid communication with a reservoir 75. FIG. 31B shows the embodiment of FIG. 30A, in which the cavity 73 of the band 72 is in fluid communication with the reservoir 74 via an operation device in the form of a two-way pump 76. FIG. 31C shows an operation device in the form of a reverse servo system with a first closed system controlling a second system. The reverse servo system comprises an adjustable fluid supply reservoir 77 and an adjustable servo reservoir 78. The servo reservoir 78 controls a larger adjustable reservoir 79 which in connection with the band 72 applied around a portion of tubular uterine tube wall of a patient's uterine tubes varies the volume of the cavity 73 of the band 72, which in turn varies the constriction of the wall portion. FIG. 31D shows an embodiment identical to the embodiment of FIG. 31C, except that the larger reservoir 79 is omitted. Instead, the servo reservoir 78 is in fluid communication with the cavity of the band 72.

In all of the above embodiments according to FIGS. 12A through 30B, stimulation devices may be provided to form constriction/stimulation units, in which the stimulation devices include a multiplicity of electrical elements 7 (indicated in FIGS. 12A-15, 18, 20-23, 26-31B) positioned on the constriction devices.

FIG. 32 is a cross-sectional view of a fluid supply device including a bellows reservoir 80 defining a chamber 81, the size of which is variable by an operation device comprising a remote controlled electric motor 82. The reservoir 80 and the motor 82 are placed in a housing 83. Moving a large wall 84 varies the chamber 81. The wall 84 is secured to a nut 85, which is threaded on a rotatable spindle 86. The spindle 86 is rotated by the motor 82. A battery 89 placed in the housing 83 powers the motor 82. A signal receiver 90 for controlling the motor 82 is also placed in the housing 83. Alternatively, the battery 89 and the signal receiver 90 may be mounted in a separate place. The motor 82 may also be powered with energy transferred from transmitted signals.

Where applicable, the fluid supply device of FIG. 32 may be used for supplying hydraulic fluid for the operation of the constriction devices described in this specification. For example, the fluid supply device of FIG. 32 may be substituted for the reservoir 74 in the embodiment according to FIG. 30A.

FIGS. 33A and 33B show a reverse servo including a rectangular housing 91 and an intermediate wall 92, which is movable in the housing 91. A relatively large, substantially cylindrical bellows reservoir 93 is arranged in the housing 91 and is joined to the movable intermediate wall 92. Another cylindrical bellows reservoir 94, which is substantially smaller than reservoir 93, is arranged in the housing 91 at the other side of the intermediate wall 92 and is also joined to the wall 92. The small bellows reservoir 94 has a fluid supply pipe 95 and the large bellows reservoir 93 has a fluid supply pipe 96.

Referring to FIG. 33A, when a small amount of hydraulic fluid is conducted through the supply pipe 95 into the small bellows reservoir 94, the small bellows reservoir 94 expands and pushes the movable intermediate wall 92 towards the large bellows reservoir 93. As a result, the large bellows reservoir 93 is contracted by the intermediate wall 92, whereby a large amount of hydraulic fluid is forced out of the large bellows reservoir 93 through the supply pipe 96, as shown in FIG. 33B.

For example, the reverse servo of FIGS. 33A and 33B may be used in the embodiment of FIG. 31C, wherein the small bellows reservoir 94 corresponds to the small servo reservoir 78 and the large bellows reservoir 93 corresponds to the large reservoir 79. Also, the reverse servo of FIGS. 33A and 33B may be used in the embodiment of FIGS. 30A and 30B, wherein the small bellows reservoir 94 is connected to the adjustable reservoir 74, and the large bellows reservoir 93 is connected to the cavity 73 of the band 72.

Figure 34:
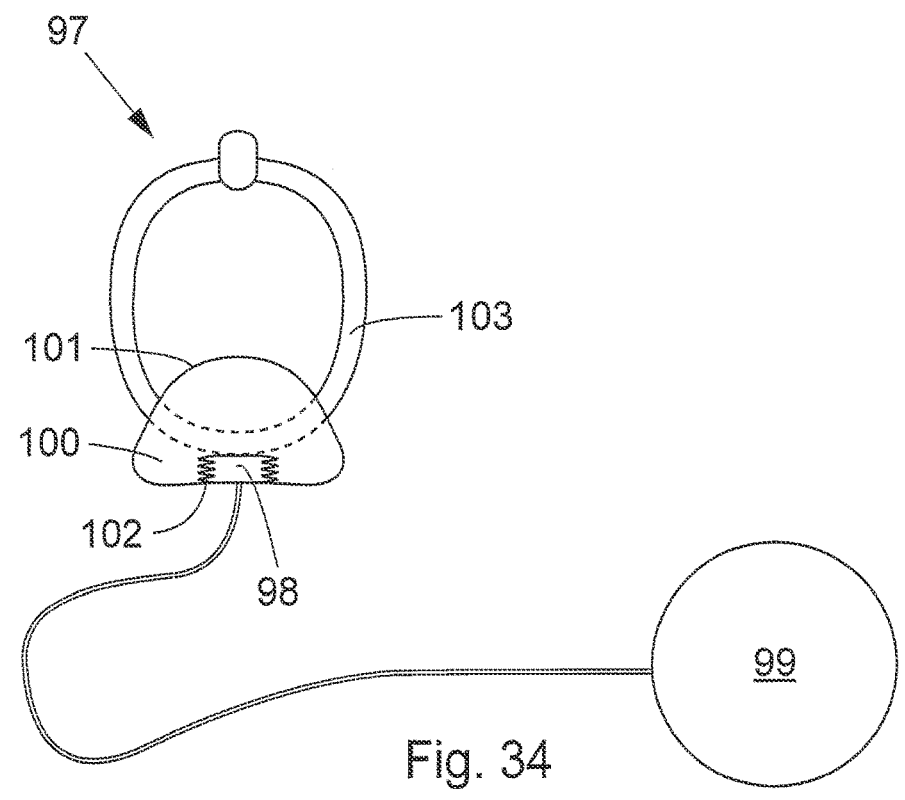
FIG. 34 is a schematic view of another hydraulically operable constriction device for use in accordance with the invention.

FIG. 34 schematically shows a hydraulically operable constriction device 97 of the apparatus of the invention, which is similar to the embodiment shown in FIG. 30A, except that the hydraulic system is designed differently. Thus, the constriction device 97 includes a relatively small inflatable cavity 98, which is in fluid communication with a reservoir 99 containing hydraulic fluid, and a relatively large cavity 100, which is displaceable by small cavity 98. Small cavity 98 is adapted to displace large cavity 100 to constrict the patient's tubular wall portion when small cavity 98 is inflated and to displace large cavity 100 to release the wall portion when small cavity 98 is deflated. Thus, a relatively small addition of hydraulic fluid from reservoir 99 to small cavity 98 causes a relatively large increase in the constriction of the wall portion.

Large cavity 100 is defined by a contraction element in the form of a big balloon 101, which may be connected to an injection port (not shown) for calibration of the volume of large cavity 100. Adding fluid to or withdrawing fluid from the injection port with the aid of a syringe calibrates the volume of balloon 101. Small cavity 98 is defined by a small bellows 102 attached to an annular frame 103 of constriction device 97 and at the opposite end is attached to balloon 101.

Figure 35A:
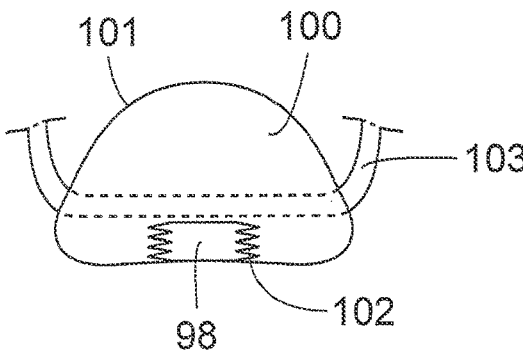
FIG. 35A illustrates the constriction device of FIG. 34 in a constricted state.
Figure 35B:
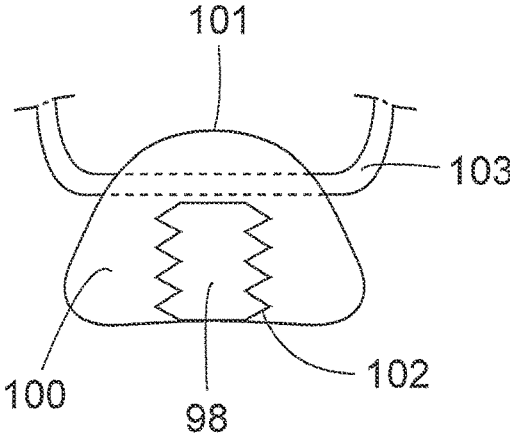
FIG. 35B illustrates the constriction device of FIG. 34 in a released state.

FIGS. 35A and 35B schematically illustrate the operation of constriction device 97, when annular frame 103 is applied around the tubular wall portion of the patient's organ. Referring to FIG. 35A, when small cavity 98 is deflated bellows 102 pulls balloon 101 inwardly into annular frame 103, so that constriction device 97 constricts the wall portion. Referring to FIG. 35B, when small cavity 98 is inflated bellows 102 pulls balloon 101 out of annular frame 103, so that constriction device 97 releases the wall portion.

As mentioned above, the constriction device and stimulation device can co-operate to actively move the sperms in the uterine tubes of a patient. This can be achieved using the constriction/stimulation unit shown in FIG. 2. Thus, in accordance with a first cooperation option, the clamping elements 5, 6 of the constriction device constricts the wall portion 8 without completely closing the uterine tube, whereby the flow in the uterine tube is restricted, and the control device 4 controls the electrical elements 7 to progressively stimulate the constricted wall portion in the downstream or upstream direction of the uterine tube to cause progressive contraction of the wall portion 8 to move the sperms in the uterine tube.

In accordance with a second cooperation option, the constriction device constricts the wall portion so that the flow in the uterine tube is restricted, and the control device 4 controls a few electrical elements 7 at one end of the elongate clamping elements 5, 6 to stimulate the constricted wall portion 8 to close the uterine tube either at an upstream end or a downstream end of the wall portion 8. With the uterine tube closed in this manner, the control device 4 controls the constriction device to increase the constriction of the wall portion, whereby the sperms in the uterine tube is moved downstream or upstream of the wall portion 8.

In another embodiment of the invention for performing the second cooperation option, the constriction device constricts the wall portion so that the flow in the uterine tube is restricted, and the control device 4 controls the stimulation device to stimulate the constricted wall portion while the constriction device varies the constriction of the different areas of the wall portion, such that the wall portion is progressively constricted in the downstream or upstream direction of the uterine tube. FIGS. 36A-36E show different operation stages of such an alternative embodiment, which comprises a constriction device 104 including two elongate constriction elements 105, 106 having convex surfaces 107, 108 that abut a length of the wall portion 8 on mutual sides thereof, and a multiplicity of electrical elements 7 (such as electrodes) that are positioned on the convex surfaces 107, 108. The control device 4 controls the electrical elements 7 during operation of the constriction device 104 and controls the elongate constriction elements 105, 106 to move relative to the tubular wall portion 8 so that the constriction elements 105, 106 progressively constrict the wall portion 8, as appears from FIGS. 36A to 36D.

Thus, in an initial position of the constriction elements 105, 106 shown in FIG. 36A, the wall portion is not constricted by the constriction elements 105, 106 and the electrical elements 7 are not energized. Starting from this initial position, the control device 4 controls the constriction elements 105, 106 to swing the left ends of the constriction elements 105, 106 toward the wall portion (indicated by arrows) to constrict the tubular wall portion 8, see FIG. 36B, while energizing the electrical elements 7, so that the electrical elements 7 that contact the wall portion 8 contract the latter. FIG. 36C shows how the uterine tube is completely closed by the thickened wall portion 8. Then, as shown in FIG. 36C, the control device 4 controls the constriction elements 105, 106 to move so that their right ends are moving towards each other (indicated by arrows), while the convex surfaces 107, 108 of the constriction elements 105, 106 are rolling on each other with the contracted wall portion 8 between them, see FIG. 36D. As a result, the sperm in the uterine tube of the organ is forced to the right (indicated by a white arrow). When the constriction elements 105, 106 have rolled on each other to the position shown in FIG. 36E, the control device 4 controls the right ends of the constriction elements 105, 106 to move away from each other (indicated by arrows in FIG. 36E) to the initial position shown in FIG. 36A. The operation stages described according to FIGS. 36A to 36E can be cyclically repeated a number of times until the desired amount of sperms has been moved in the uterine tube of the organ in a peristaltic manner.

Alternatively, only one of the constriction elements 105, 106 can be provided with a convex surface, whereas the other constriction element has a plane surface that abuts the wall portion. It is also possible to use a single constriction element with a convex surface that presses the tubular portion 8 of the organ against a bone of the patient.

In the embodiment according to FIGS. 36A to 36E, the control device 4 may control the electrical elements 7 to progressively stimulate the constricted wall portion 8 to cause progressive contraction thereof in harmony with the movement of the elongate constriction elements 105, 106, as the convex surfaces 107, 108 of the constriction elements 105, 106 are rolling on each other.

Figures 37, 38, 39, 40, 41:
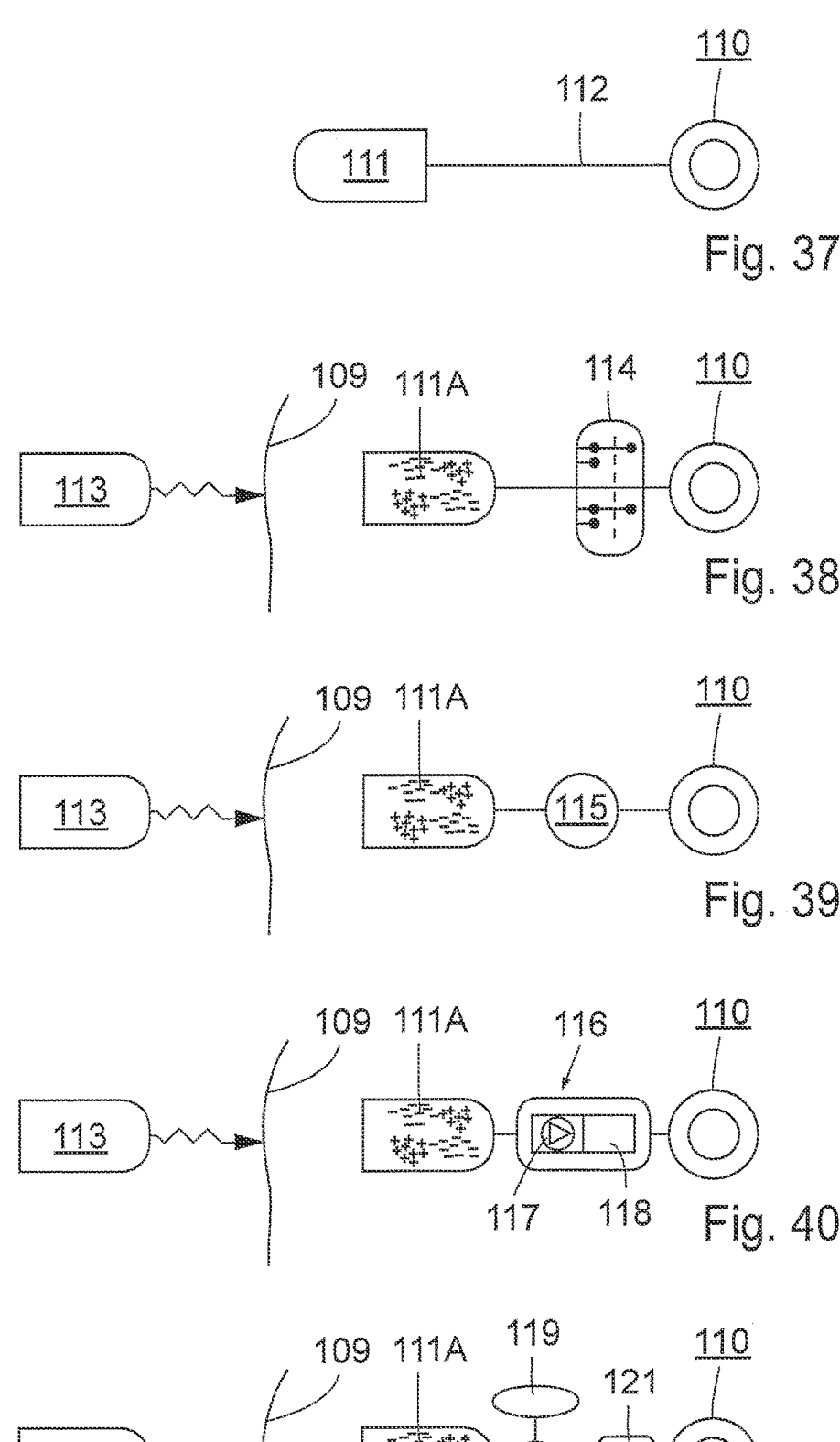
FIG. 37 is a schematic block diagram illustrating a general embodiment of the apparatus of the invention, in which energy is transferred to energy consuming components of the apparatus implanted in the patient.
FIGS. 38 to 49 are schematic block diagrams illustrating twelve embodiments, respectively, based on the general embodiment shown in FIG. 37, wherein wireless energy is transmitted from outside a patient's body to energy consuming components of the apparatus implanted in the patient.

FIG. 37 schematically shows a general embodiment of the apparatus of the invention, in which energy is transferred to energy consuming components of the apparatus implanted in the patient. The apparatus of FIG. 37 comprises an implanted constriction/stimulation unit 110, which is operable to gently constrict a portion of a tubular uterine tube wall of a patient and to stimulate different areas of the constricted portion to cause contraction of the wall portion. The constriction device of the constriction/stimulation unit 110 is capable of performing a reversible function, i.e., to constrict and release the wall portion.

A source of energy 111 is adapted to supply energy consuming components of the constriction/stimulation unit 110 with energy via a power supply line 112. A wireless remote control or a subcutaneously implanted switch operable by the patient to switch on or off the supply of energy from the source of energy may be provided. The source of energy may be an implantable permanent or rechargeable battery, or be included in an external energy-transmission device, which may be operable directly by the patient or be controlled by a remote control operable by the patient to transmit wireless energy to the energy consuming components of the constriction/stimulation unit. Alternatively, the source of energy may comprise a combination of an implantable rechargeable battery, an external energy-transmission device and an implantable energy-transforming device for transforming wireless energy transmitted by the external energy-transmission device into electric energy for the charge of the implantable rechargeable battery.

FIG. 38 shows a special embodiment of the general embodiment of FIG. 37 having some parts implanted in a patient and other parts located outside the patient's body. Thus, in FIG. 38 all parts placed to the right of the patient's skin 109 are implanted and all parts placed to the left of the skin 109 are located outside the patient's body. An implanted energy-transforming device 111A of the apparatus is adapted to supply energy consuming components of the constriction/stimulation unit 110 with energy via the power supply line 112. An external energy-transmission device 113 of the apparatus includes a wireless remote control transmitting a wireless signal, which is received by a signal receiver incorporated in the implanted energy-transforming device 111A. The implanted energy-transforming device 111A transforms energy from the signal into electric energy, which is supplied via the power supply line 112 to the constriction/stimulation unit 110.

The apparatus of FIG. 38 may also include an implanted rechargeable battery for energizing energy consuming implanted components of the apparatus. In this case, the implanted energy-transforming device 111A also charges the battery with electric energy, as the energy-transforming device transforms energy from the signal into the electric energy.

A reversing device in the form of an electric switch 114, such as a microprocessor, is implanted in the patient for reversing the constriction device of the constriction/stimulation unit 110. The wireless remote control of the external energy-transmission device 113 transmits a wireless signal that carries energy and the implanted energy-transforming device 111A transforms the wireless energy into a current for operating the switch 114. When the polarity of the current is shifted by the energy-transforming-device 111A the switch 114 reverses the function performed by the constriction device of the constriction/stimulation unit 110.

FIG. 39 shows an embodiment of the invention including the energy-transforming device 111A, the constriction/stimulation unit 110 and an implanted operation device in the form of a motor 115 for operating the constriction device of the constriction/stimulation unit 110. The motor 115 is powered with energy from the energy-transforming device 111A, as the remote control of the external energy-transmission device113 transmits a wireless signal to the receiver of the energy-transforming device 111A.

FIG. 40 shows an embodiment of the invention including the energy-transforming device 111A, the constriction/stimulation unit 110 and an implanted assembly 116 including a motor/pump unit 117 and a fluid reservoir 118. In this case the constriction device of the constriction/stimulation unit 110 is hydraulically operated, i.e., hydraulic fluid is pumped by the motor/pump unit 117 from the reservoir 118 to the constriction/stimulation unit 110 to constrict the wall portion, and hydraulic fluid is pumped by the motor/pump unit 117 back from the constriction/stimulation unit 110 to the reservoir 118 to release the wall portion. The implanted energy-transforming device 111A transforms wireless energy into a current, for powering the motor/pump unit 117.

FIG. 41 shows an embodiment of the invention comprising the external energy-transmission device 113. that controls the control unit 122 to reverse the motor 115 when needed, the constriction/stimulation unit 110, the constriction device of which is hydraulically operated, and the implanted energy-transforming device 111A, and further comprising an implanted hydraulic fluid reservoir 119, an implanted motor/pump unit 120, an implanted reversing device in the form of a hydraulic valve shifting device 121 and a separate external wireless remote control 111B. The motor of the motor/pump unit 120 is an electric motor. In response to a control signal from the wireless remote control of the external energy-transmission device 113, the implanted energy-transforming device 111A powers the motor/pump unit 120 with energy from the energy carried by the control signal, whereby the motor/pump unit 120 distributes hydraulic fluid between the reservoir 119 and the constriction device of the constriction/stimulation unit 110. The remote control 111B controls the shifting device 121 to shift the hydraulic fluid flow direction between one direction in which the fluid is pumped by the motor/pump unit 120 from the reservoir 119 to the constriction device of the constriction/stimulation unit 110 to constrict the wall portion, and another opposite direction in which the fluid is pumped by the motor/pump unit 120 back from the constriction device of the constriction/stimulation unit 110 to the reservoir 119 to release the wall portion.

Figure 42:
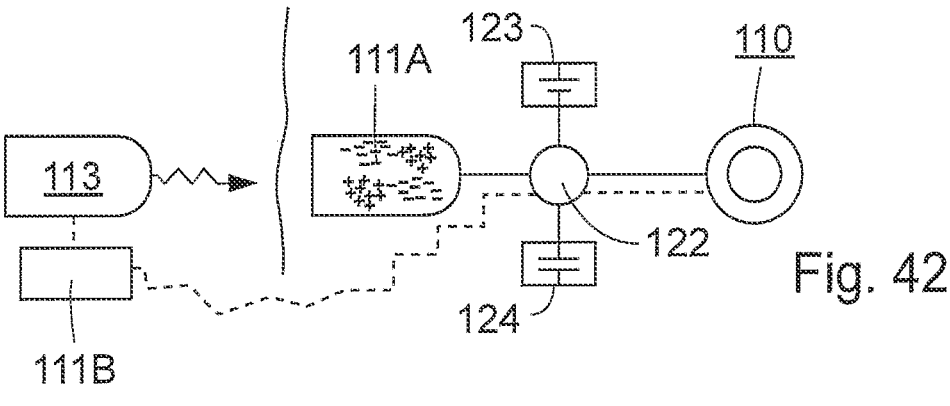

FIG. 42 shows an embodiment of the invention including the energy-transforming device 111A and the constriction/stimulation unit 110. A control unit 122, an accumulator 123 and a capacitor 124 are also implanted in the patient. A separate external wireless remote control 111B controls the control unit 122. The control unit 122 controls the energy-transforming device 111A to store electric energy in the accumulator 123, which supplies energy to the constriction/stimulation unit 110. In response to a control signal from the wireless remote control 111B, the control unit 122 either releases electric energy from the accumulator 123 and transfers the released energy via power lines, or directly transfers electric energy from the energy-transforming device 111A via the capacitor 124, which stabilises the electric current, for the operation of the constriction/stimulation unit 110.

In accordance with one alternative, the capacitor 124 in the embodiment of FIG. 42 may be omitted. In accordance with another alternative, the accumulator 123 in this embodiment may be omitted.

Figure 43:
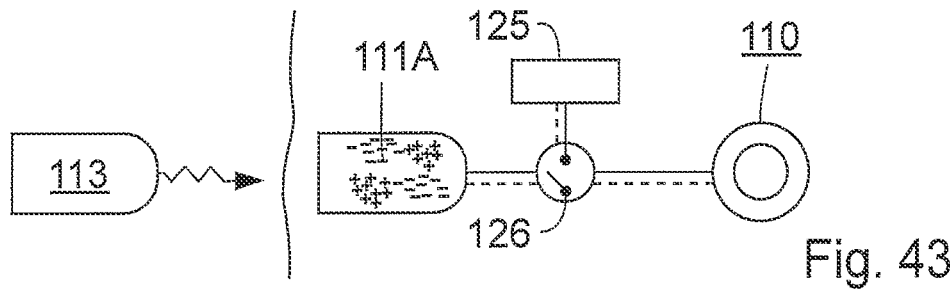

FIG. 43 shows an embodiment of the invention including the energy-transforming device 111A, the constriction/stimulation unit 110. A battery 125 for supplying energy for the operation of the constriction/stimulation unit 110 and an electric switch 126 for switching the operation of the constriction/stimulation unit 110 are also implanted in the patient. The switch 126 is operated by the energy supplied by the energy-transforming device 111A to switch from an off mode, in which the battery 125 is not in use, to an on mode, in which the battery 125 supplies energy for the operation of the constriction/stimulation unit 110.

Figure 44:
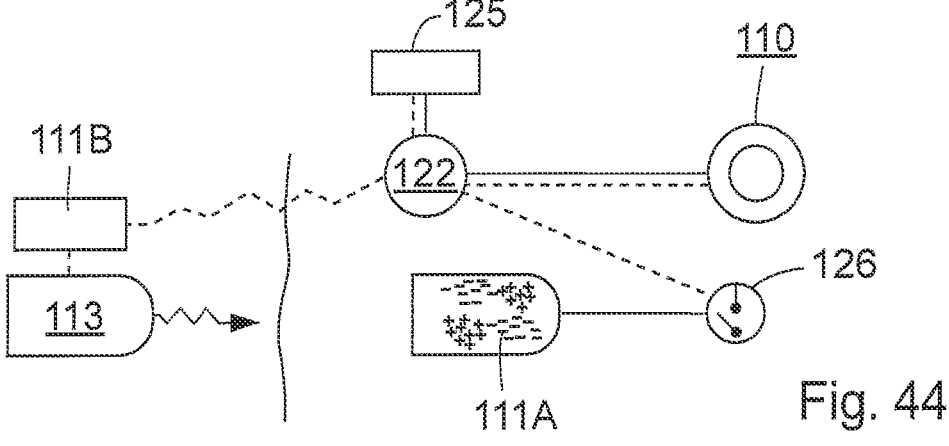

FIG. 44 shows an embodiment of the invention identical to that of FIG. 43, except that a control unit 122 also is implanted in the patient. A separate external wireless remote control 111B controls the control unit 122. In this case, the switch 126 is operated by the energy supplied by the energy-transforming device 111A to switch from an off mode, in which the wireless remote control 111B is prevented from controlling the control unit 122 and the battery 125 is not in use, to a standby mode, in which the remote control 111B is permitted to control the control unit 122 to release electric energy from the battery 125 for the operation of the constriction/stimulation unit 110.

Figure 45:
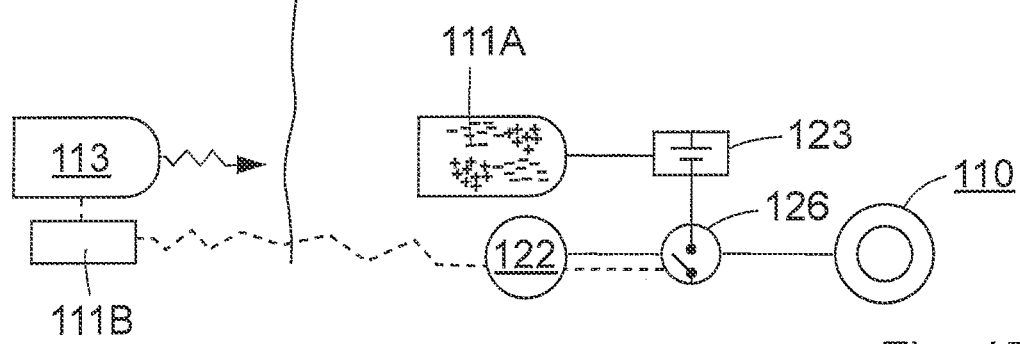

FIG. 45 shows an embodiment of the invention identical to that of FIG. 44, except that the accumulator 123 is substituted for the battery 125 and the implanted components are interconnected differently. In this case, the accumulator 123 stores energy from the energy-transforming device 111A. In response to a control signal from the wireless remote control 111B, the implanted control unit 122 controls the switch 126 to switch from an off mode, in which the accumulator 123 is not in use, to an on mode, in which the accumulator 123 supplies energy for the operation of the constriction/stimulation unit 110.

Figures 46, 47, 48, 49:
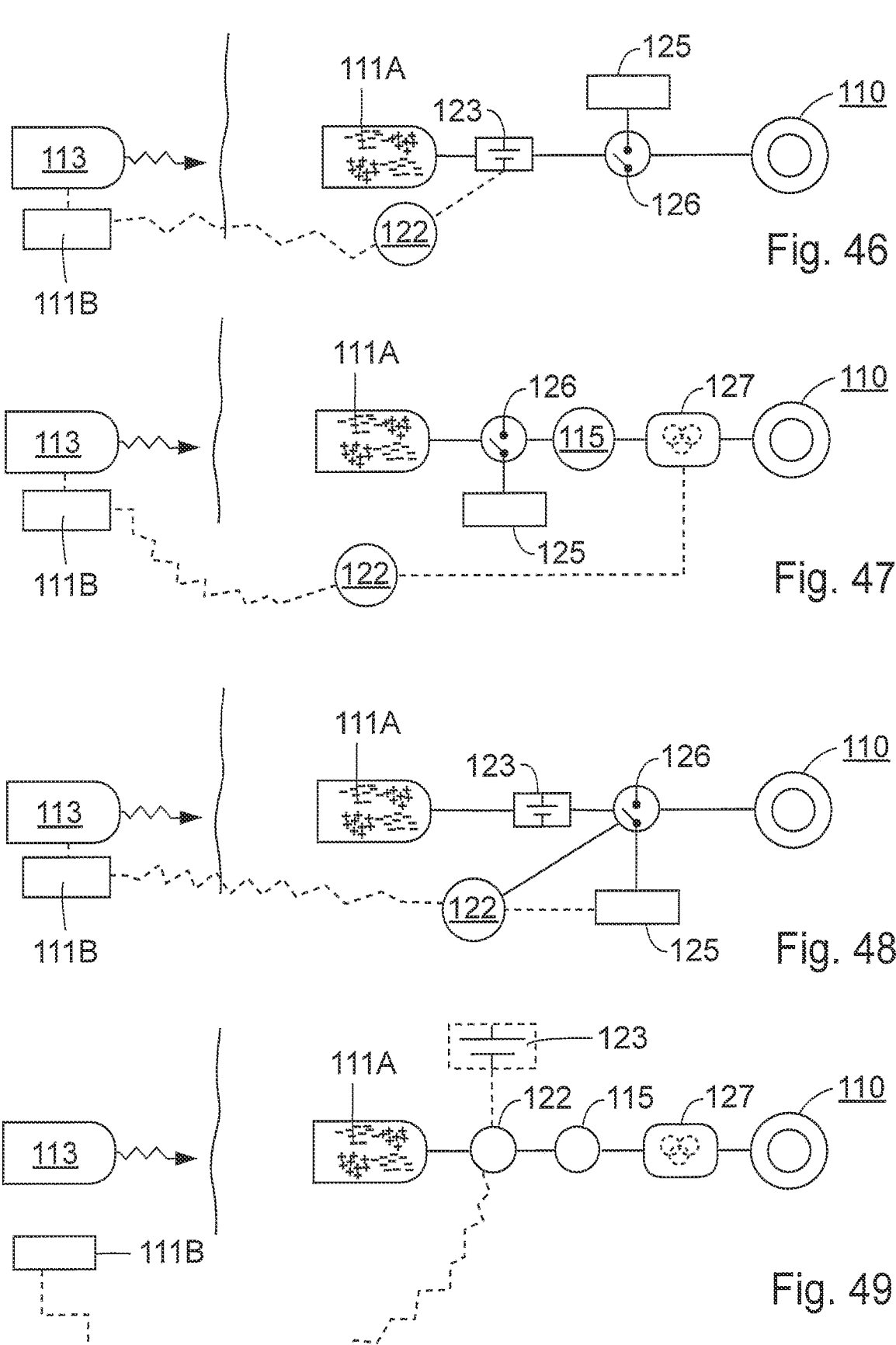

FIG. 46 shows an embodiment of the invention identical to that of FIG. 45, except that the battery 125 also is implanted in the patient, and the implanted components are interconnected differently. In response to a control signal from the wireless remote control 111B, the implanted control unit 122 controls the accumulator 123, which may be a capacitor, to deliver energy for operating the switch 126 to switch from an off mode, in which the battery 125 is not in use, to an on mode, in which the battery 125 supplies electric energy for the operation of the constriction/stimulation unit 110.

Alternatively, the switch 126 may be operated by energy supplied by the accumulator 123 to switch from an off mode, in which the wireless remote control 111B is prevented from controlling the battery 125 to supply electric energy and the battery 125 is not in use, to a standby mode, in which the wireless remote control 111B is permitted to control the battery 125 to supply electric energy for the operation of the constriction/stimulation unit 110.

FIG. 47 shows an embodiment of the invention identical to that of FIG. 43, except that a motor 115, a mechanical reversing device in the form of a gearbox 127 and a control unit 122 for controlling the gearbox 127 also are implanted in the patient. A separate external wireless remote control 111B controls the implanted control unit 122 to control the gearbox 127 to reverse the function performed by the constriction device (mechanically operated) of the constriction/stimulation unit 110.

FIG. 48 shows an embodiment of the invention identical to that of FIG. 46, except that the implanted components are interconnected differently. Thus, in this case, the battery 125 powers the control unit 122 when the accumulator 123, suitably a capacitor, activates the switch 126 to switch to an on mode. When the switch 126 is in its on mode the control unit 122 is permitted to control the battery 125 to supply, or not supply, energy for the operation of the constriction/stimulation unit 110.

FIG. 49 shows an embodiment of the invention identical to that of FIG. 39, except that a gearbox 127 that connects the motor 115 to the constriction/stimulation unit 110, and a control unit 122 that controls the energy-transforming device 111A to power the motor 115 also are implanted in the patient. There is a separate external wireless remote control 111B that controls the control unit 122 to reverse the motor 115 when needed.

Optionally, the accumulator 123 shown in FIG. 42 may be provided in the embodiment of FIG. 49, wherein the implanted control unit 122 controls the energy-transforming device 111A to store the transformed energy in the accumulator 123. In response to a control signal from the wireless remote control 111B, the control unit 122 controls the accumulator 123 to supply energy for the operation of the constriction/stimulation unit 110.

Those skilled in the art will realise that the above various embodiments according to FIGS. 38-49 could be combined in many different ways. For example, the energy operated switch 114 could be incorporated in any of the embodiments of FIGS. 39, 42-49, the hydraulic shifting device 121 could be incorporated in the embodiment of FIG. 40, and the gearbox 127 could be incorporated in the embodiment of FIG. 39. The switch 114 may be of a type that includes electronic components, for example a microprocessor, or a FGPA (Field Programmable Gate Array) designed for switching. Alternatively, however, the energy operated switch 114 may be replaced by a subcutaneously implanted push button that is manually switched by the patient between "on" and "off".

Alternatively, a permanent or rechargeable battery may be substituted for the energy-transforming devices 111A of the embodiments shown in FIGS. 38-49.

Figure 50:
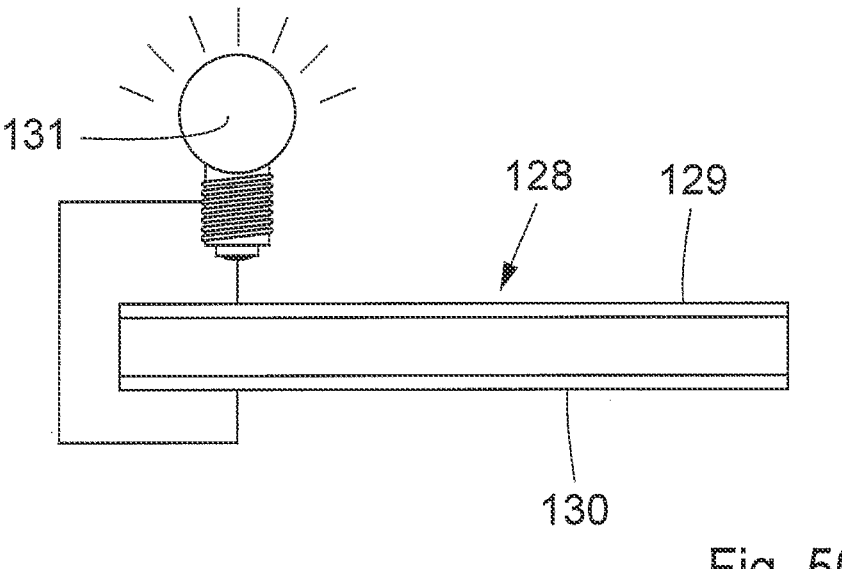
FIG. 50 illustrates an energy-transforming device in the form of an electrical junction element for use in the apparatus of the present invention.

FIG. 50 shows the energy-transforming device in the form of an electrical junction element 128 for use in any of the above embodiments according to FIGS. 37-49. The element 128 is a flat p-n junction element comprising a p-type semiconductor layer 129 and an n-type semiconductor layer 130 sandwiched together. A light bulb 131 is electrically connected to opposite sides of the element 128 to illustrate how the generated current is obtained. The output of current from such a p-n junction element 128 is correlated to the temperature. See the formula below.

$$I = I0 \ (\exp(qV/kT) - 1)$$

Where

I is the external current flow,

I0 is the reverse saturation current, q is the fundamental electronic charge of $1.602 \times 10\text{-}19$ coulombs, V is the applied voltage, k is the Boltzmann constant, and T is the absolute temperature.

Under large negative applied voltage (reverse bias), the exponential term becomes negligible compared to 1.0, and I is approximately −I0. I0 is strongly dependent on the temperature of the junction and hence on the intrinsic-carrier concentration. I0 is larger for materials with smaller bandgaps than for those with larger bandgaps. The rectifier action of the diode, that is, its restriction of current flow to only one direction, is in this particular embodiment the key to the operation of the p-n junction element 128.

The alternative way to design a p-n junction element is to deposit a thin layer of semiconductor onto a supporting material which does not absorb the kind of energy utilised in the respective embodiments. For use with wirelessly transmitted energy in terms of light waves, glass could be a suitable material. Various materials may be used in the semiconductor layers, such as, but not limited to, cadmium telluride, copper-indium-diselenide and silicon. It is also possible to use a multilayer structure with several layers of p and n-type materials to improve efficiency.

The electric energy generated by the p-n junction element 128 could be of the same type as generated by solar cells, in which the negative and positive fields create a direct current. Alternatively, the negative and positive semiconductor layers may change polarity following the transmitted waves, thereby generating the alternating current.

The p-n junction element 128 is designed to make it suited for implantation. Thus, all the external surfaces of the element 128 in contact with the human body are made of a biocompatible material. The p-n junction semiconductors are designed to operate optimally at a body temperature of 37° C. because the current output, which should be more than 1 μA, is significantly dependent upon such temperature, as shown above. Since both the skin and subcutis absorb energy, the relation between the sensitivity or working area of the element 128 and the intensity or strength of the wireless energy-transmission is considered. The p-n junction element 128 preferably is designed flat and small. Alternatively, if the element 128 is made in larger sizes it should be flexible, in order to adapt to the patient's body movements. The volume of the element 128 should be kept less than 2000 cm³.

Figure 51:
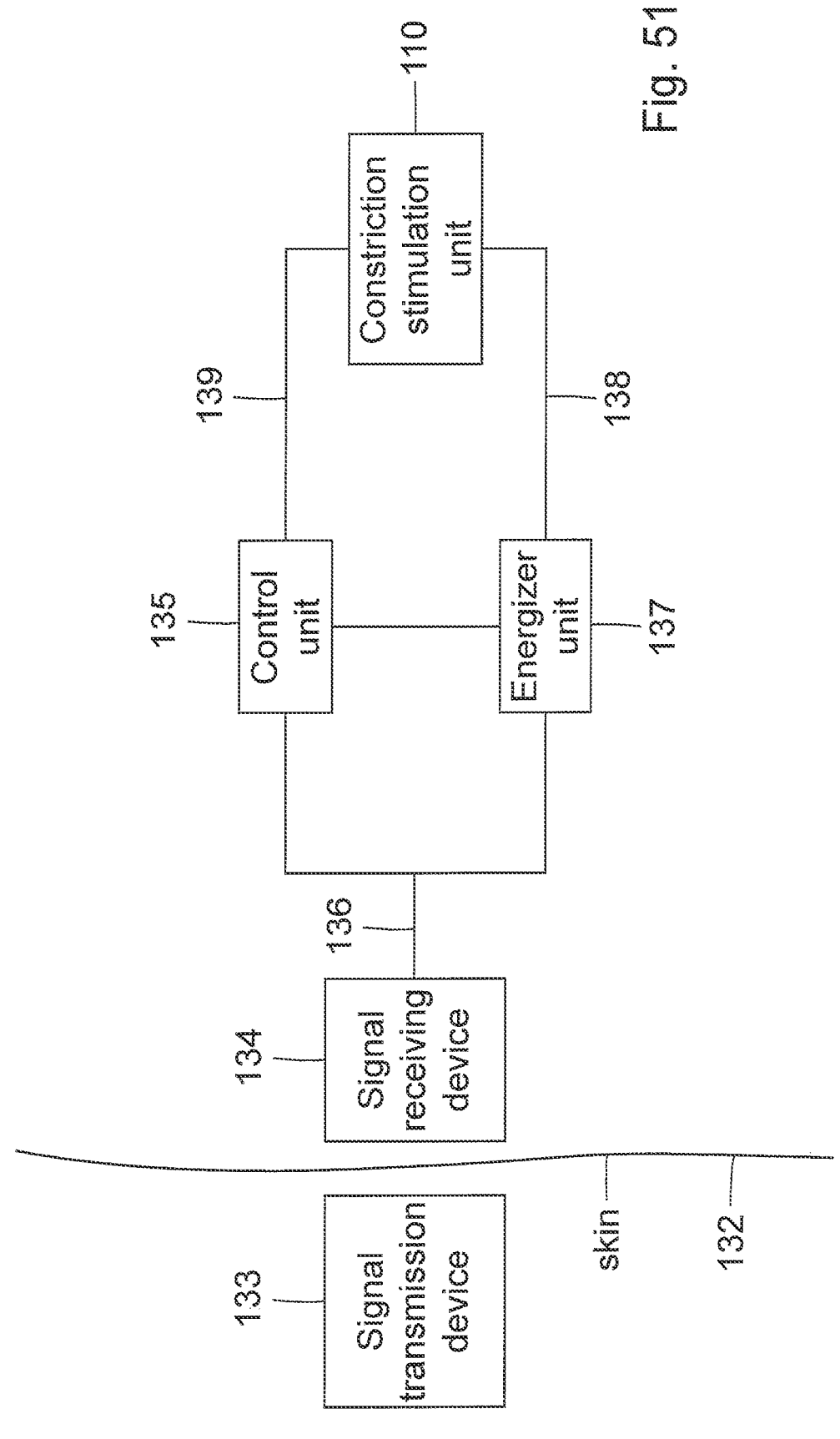
FIG. 51 is a block diagram illustrating control components of an embodiment of the invention.

FIG. 51 shows basic parts of a remote control of the apparatus of the invention for controlling the constriction/stimulation unit 110. In this case, the stimulation device of the constriction/stimulation unit stimulates the wall portion with electric pulses. The remote control is based on wireless transmission of electromagnetic wave signals, often of high frequencies in the order of 100 kHz-1 gHz, through the skin 132 of the patient. In FIG. 51, all parts placed to the left of the skin 132 are located outside the patient's body and all parts placed to the right of the skin 132 are implanted.

An external signal-transmission device 133 is to be positioned close to a signal-receiving device 134 implanted close to the skin 132. As an alternative, the signal-receiving device 134 may be placed for example inside the abdomen of the patient. The signal-receiving device 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The signal transmission device 133 comprises a coil having about the same size as the coil of the signal-receiving device 134 but wound with a thick wire that can handle the larger currents that is necessary. The coil of the signal transmission device 133 is tuned to the same specific high frequency as the coil of the signal-receiving device 134.

The signal-transmission device 133 is adapted to send digital information via the power amplifier and signal-receiving device 134 to an implanted control unit 135. To avoid that accidental random high frequency fields trigger control commands, digital signal codes are used. A conventional keypad placed on the signal transmission device 133 is used to order the signal transmission device 133 to send digital signals for the control of the constriction/stimulation unit. The signal transmission device 133 starts a command by generating a high frequency signal. After a short time, when the signal has energized the implanted parts of the control system, commands are sent to operate the constriction device of the constriction/stimulation unit 110 in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g., about 30 seconds or more). When a new constriction or release step is desired, the Count byte is increased by one to allow the implanted control unit 135 to decode and understand that another step is demanded by the signal transmission device 133. If any part of the digital packet is erroneous, its content is simply ignored.

Through a line 136, an implanted energizer unit 137 draws energy from the high frequency electromagnetic wave signals received by the signal-receiving device 134. The energizer unit 137 stores the energy in a source of energy, such as a large capacitor, powers the control unit 135 and powers the constriction/stimulation unit 110 via a line 138.

The control unit 135 comprises a demodulator and a microprocessor. The demodulator demodulates digital signals sent from the signal transmission device 133. The microprocessor receives the digital packet, decodes it and sends a control signal via a signal line 139 to control the constriction device of the constriction/stimulation unit 110 to either constrict or release the wall portion of the patient's organ depending on the received command code.

Figure 52:
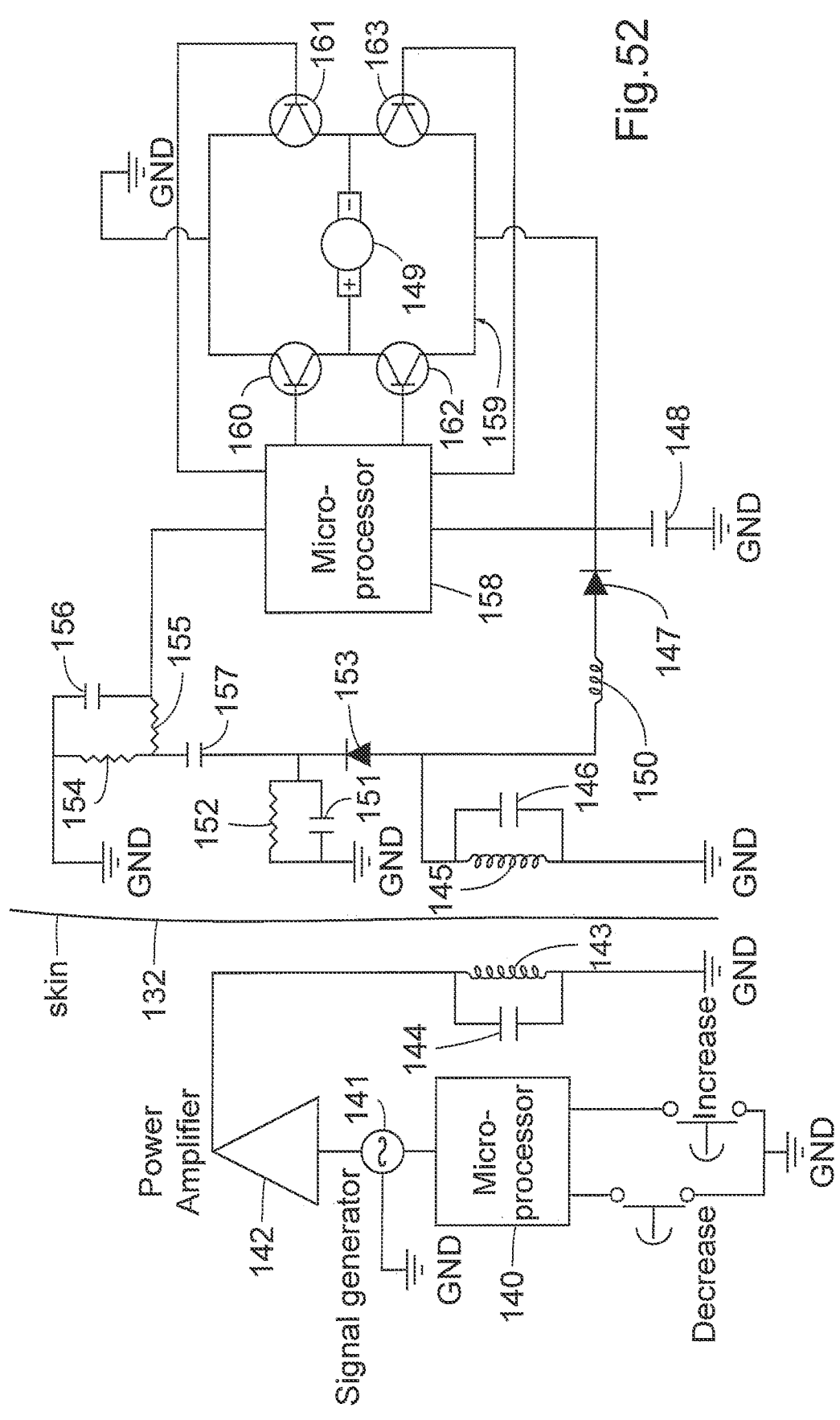
FIG. 52 is a schematic view of exemplary circuitry of an embodiment of the invention, in which wireless energy is transformed into a current.

FIG. 52 shows a circuitry of an embodiment of the invention, in which wireless energy is transformed into a current. External components of the circuitry include a microprocessor 140, a signal generator 141 and a power amplifier 142 connected thereto. The microprocessor 140 is adapted to switch the signal generator 141 on/off and to modulate signals generated by the signal generator 141 with digital commands. The power amplifier 142 amplifies the signals and sends them to an external signal-transmitting antenna coil 143. The antenna coil 143 is connected in parallel with a capacitor 144 to form a resonant circuit tuned to the frequency generated by the signal generator 141.

Implanted components of the circuitry include a signal receiving antenna coil 145 and a capacitor 146 forming together a resonant circuit that is tuned to the same frequency as the transmitting antenna coil 143. The signal receiving antenna coil 145 induces a current from the received high frequency electromagnetic waves and a rectifying diode 147 rectifies the induced current, which charges a storage capacitor 148. The storage capacitor 148 powers a motor 149 for driving the constriction device of the constriction/stimulation unit 110. A coil 150 connected between the antenna coil 145 and the diode 147 prevents the capacitor 148 and the diode 147 from loading the circuit of the signal-receiving antenna 145 at higher frequencies. Thus, the coil 150 makes it possible to charge the capacitor 148 and to transmit digital information using amplitude modulation.

A capacitor 151 and a resistor 152 connected in parallel and a diode 153 form a detector used to detect amplitude modulated digital information. A filter circuit is formed by a resistor 154 connected in series with a resistor 155 connected in series with a capacitor 156 connected in series with the resistor 154 via ground, and a capacitor 157, one terminal of which is connected between the resistors 154, 155 and the other terminal of which is connected between the diode 153 and the circuit formed by the capacitor 151 and resistor 152. The filter circuit is used to filter out undesired low and high frequencies. The detected and filtered signals are fed to an implanted microprocessor 158 that decodes the digital information and controls the motor 149 via an H-bridge 159 comprising transistors 160, 161, 162 and 163. The motor 149 can be driven in two opposite directions by the H-bridge 159.

The microprocessor 158 also monitors the amount of stored energy in the storage capacitor 148. Before sending signals to activate the motor 149, the microprocessor 158 checks whether the energy stored in the storage capacitor 148 is enough. If the stored energy is not enough to perform the requested operation, the microprocessor 158 waits for the received signals to charge the storage capacitor 148 before activating the motor 149.

Alternatively, the energy stored in the storage capacitor 148 may only be used for powering a switch, and the energy for powering the motor 149 may be obtained from another implanted energy source of relatively high capacity, for example a battery. In this case the switch is adapted to connect the battery to the motor 149 in an on mode when the switch is powered by the storage capacitor 148 and to keep the battery disconnected from the motor 149 in a standby mode when the switch is not powered.

Figure 53A:
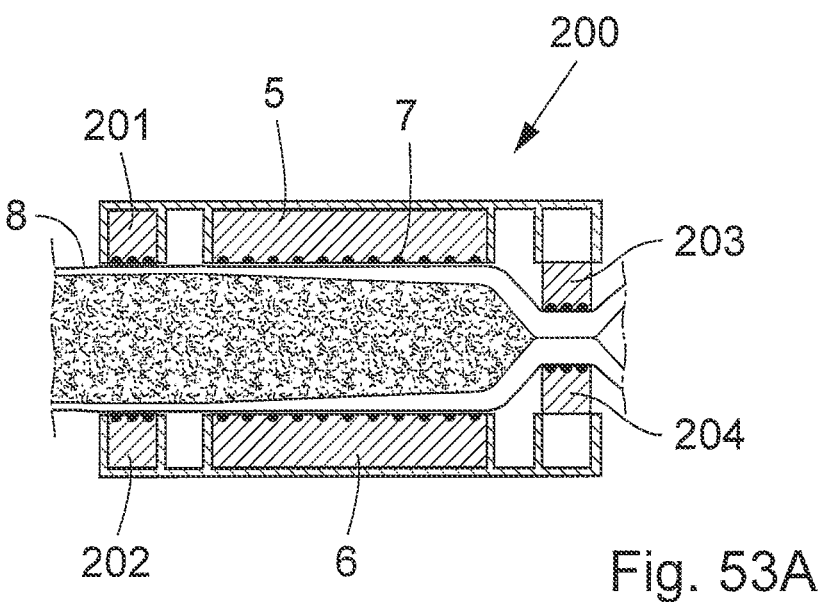
FIGS. 53A-53C schematically illustrate different operation stages of another embodiment of the invention of the type shown in FIG. 2, in which a constriction device and a stimulation device co-operate to move the sperms in the uterine tube of a patient's uterine tube.
Figure 53B:
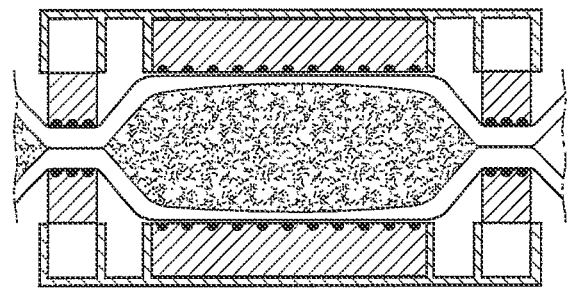
Figure 53C:
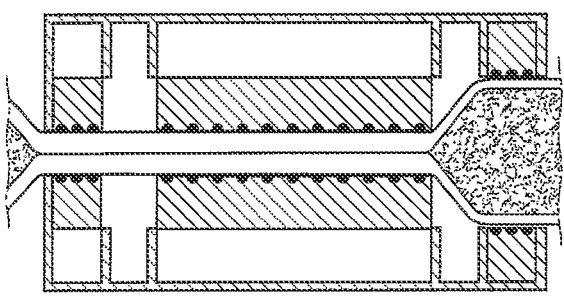

FIGS. 53A-53C show an embodiment of the invention, which is similar to the embodiment of FIG. 2, except that the constriction/stimulation unit, here denoted by reference numeral 200, is provided with additional clamping elements. The embodiment of FIGS. 53A-53C is suited for actively moving the sperms in the uterine tube of a patient. Thus, the constriction/stimulation unit 200 also includes a first pair of short clamping elements 201 and 202, and a second pair of short clamping elements 203 and 204, wherein the first and second pairs of clamping elements are positioned at mutual sides of the elongate clamping elements 5, 6. The two short clamping elements 201, 202 of the first pair are radially movable towards and away from each other between retracted positions (FIG. 53A) and clamping positions (FIGS. 53B and 53C), and the two short clamping elements 203, 204 of the second pair are radially movable towards and away from each other between retracted positions (FIG. 53C) and clamping positions (FIGS. 53A and 53B). The stimulation device 3 also includes electrical elements 7 positioned on the short clamping elements 201-204, so that the electrical elements 7 on one of the short clamping elements 201 and 203, respectively, of each pair of short elements face the electrical elements 7 on the other short clamping element 202 and 204, respectively, of each pair of short elements.

The constriction/stimulation unit 200 is applied on a wall portion 8 of a tubular uterine tube wall of a patient, so that the short clamping elements 201, 202 are positioned at an upstream end of the wall portion 8, whereas the short clamping elements 203, 204 202 are positioned at a downstream end of the wall portion 8. In FIGS. 53A to 53C the upstream end of the wall portion 8 is to the left and the downstream end of the wall portion 8 is to the right.

The control device 4 controls the pair of short clamping elements 201, 202, the pair of elongate clamping elements 5, 6 and the pair of short elements 203, 204 to constrict and release the wall portion 8 independently of one another. The control device also controls the electrical elements 7 on a clamping element that is constricting the wall portion to stimulate the constricted wall portion 8 with electric pulses to cause contraction of the wall portion 8, so that the uterine tube of the wall portion 8 is closed.

FIGS. 53A-53C illustrate how the control device 4 controls the operation of the constriction/stimulation unit 200 to cyclically move sperms downstream in the uterine tube of the wall portion 8. Thus, in FIG. 53A the short clamping elements 201, 202 and the elongate clamping elements 5, 6 are in their retracted positions, whereas the short clamping elements 203, 204 are in their clamping positions while the electrical elements 7 on elements 203, 204 electrically stimulate the wall portion 8. The electrical stimulation causes the wall portion 8 at the elements 203, 204 to thicken, whereby the uterine tube is closed. FIG. 53B illustrates how also the short clamping elements 201, 202 have been moved radially inwardly to their clamping positions, while the electrical elements 7 on elements 201, 202 electrically stimulate the wall portion 8, whereby a volume of bodily matter is trapped in the uterine tube between the upstream and downstream ends of the wall portion 8. FIG. 53C illustrates how initially the short clamping elements 203, 204 have been moved radially outwardly to their retracted positions, and then the elongate clamping elements 5, 6 have been moved radially inwardly to their clamping positions while the electrical elements 7 on elements 5, 6 electrically stimulate the wall portion 8. As a result, the sperms in the uterine tube between the upstream and downstream ends of the wall portion 8 have been moved downstream in the uterine tube Then, the control device 4 controls the constriction/stimulation unit 200 to assume the state shown in FIG. 53A.

Alternatively, the operation cycle of the constriction/stimulation unit 200 described above may be reversed, in order to move a sperm upstream in the uterine tube. In this case, the control device 4 controls the short clamping elements 203, 204 to constrict the wall portion 8 at the downstream end thereof to restrict the flow in the uterine tube and controls the electric elements 7 to stimulate the constricted wall portion 8 with electric pulses at the downstream end to close the uterine tube. With the uterine tube closed at the downstream end of the constricted wall portion 8 and the short clamping elements 201, 202 in their retracted positions, as shown in FIG. 53A, the control device 4 controls the elongate clamping elements 5, 6 to constrict the wall portion 8 between the upstream and downstream ends thereof. As a result, the sperm contained in the wall portion 8 between the upstream and downstream ends thereof is moved upstream in the uterine tube.

Although FIGS. 53A-53C disclose pairs of clamping elements, it should be noted that it is conceivable to design the constriction/stimulation unit 200 with only a single short clamping element 201, a single elongate clamping element 5 and a single short clamping element 203. In this case the bottom of the tubular wall portion 8 is supported by stationary elements of the constriction/stimulation unit 200 opposite to the clamping elements 201, 5, and 203.

Figures 54A, 54B:
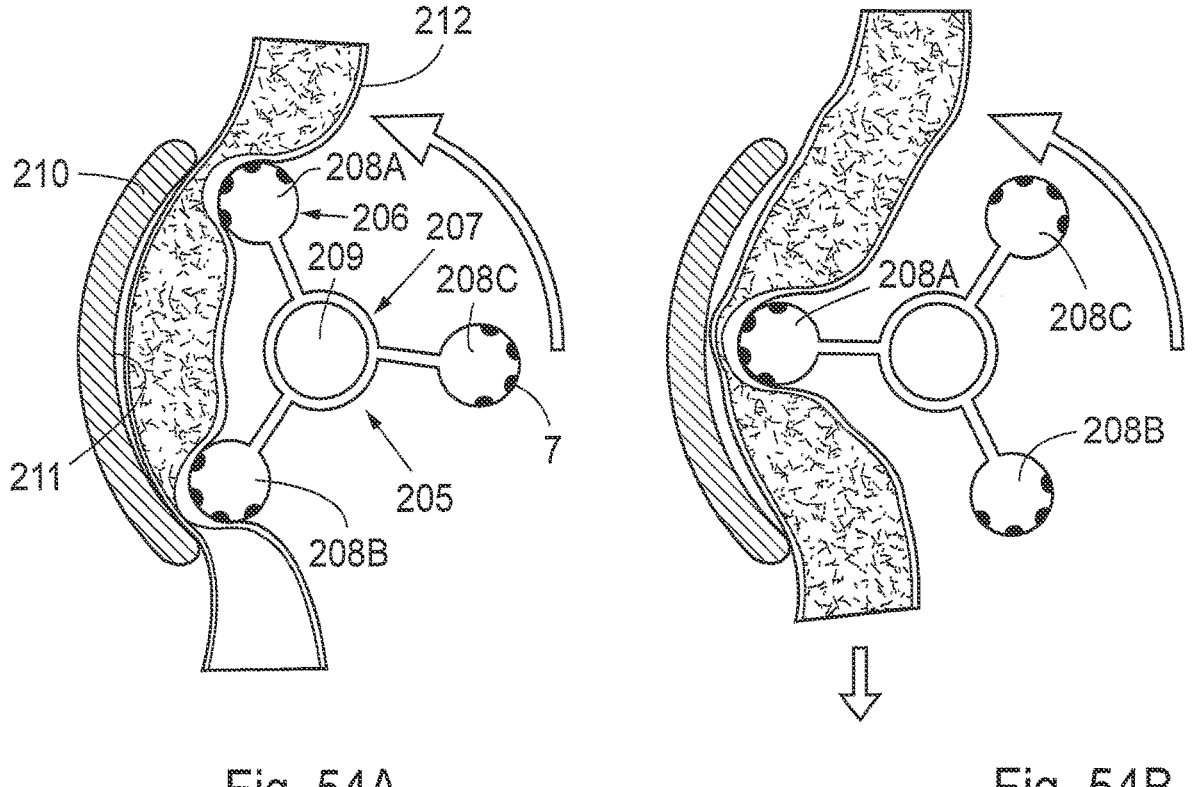
FIGS. 54A-54B schematically illustrate different operation stages of another embodiment of the invention of the type shown in FIGS. 36A-36E, in which a constriction device and a stimulation device co-operate to move the sperms in the uterine tube of a patient's uterine tube.

FIGS. 54A and 54B schematically show another embodiment of the invention, in which a constriction/stimulation unit 205 is designed for actively moving sperms in the uterine tube of a patient's tubular organ. The constriction device 206 of the constriction/stimulation unit 205 includes a rotor 207, which carries three cylindrical constriction elements 208A, 208B and 208C positioned equidistantly from the axis 209 of the rotor 207. The constriction elements 208A-208C may be designed as rollers. Each cylindrical element 208A-208C is provided with electrical elements 7. A stationary elongate support element 210 is positioned spaced from but close to the rotor 207 and has a part cylindrical surface 211 concentric with the axis 209 of the rotor 207. The constriction/stimulation unit 205 is applied on a patient's uterine tube 212, so that the organ 212 extends between the support element 210 and the rotor 207.

The control device 4 controls the rotor 207 of the constriction device to rotate, such that the constriction elements 208A-208C successively constrict wall portions of a series of wall portions of the uterine tube 212 against the elongate support element 210. The electrical elements 7 of the constriction elements 208A-208C stimulate the constricted wall portions with electric pulses so that the wall portions thicken and close the uterine tube 212. FIG. 54A illustrates how the constriction element 208A has started to constrict the wall of the uterine tube 212 and how the uterine tube 212 is closed with the aid of the electrical elements 7 on the constriction element 208A, whereas the constriction element 208B is about to release the uterine tube 212. FIG. 54B illustrates how the constriction element 208A has advanced about halfway along the elongate support element 210 and moved the sperm in the uterine tube in a direction indicated by an arrow. The constriction element 208B has released the uterine tube 212, whereas the constriction element 208C is about to engage the uterine tube 212. Thus, the control device 4 controls the rotor 207 to cyclically move the constriction elements 208A-208C, one after the other, along the elongate support element 210, while constricting the wall portions of the uterine tube 212, so that the sperm in the 212 is moved in a peristaltic manner.

Figures 55, 55A, 55B:
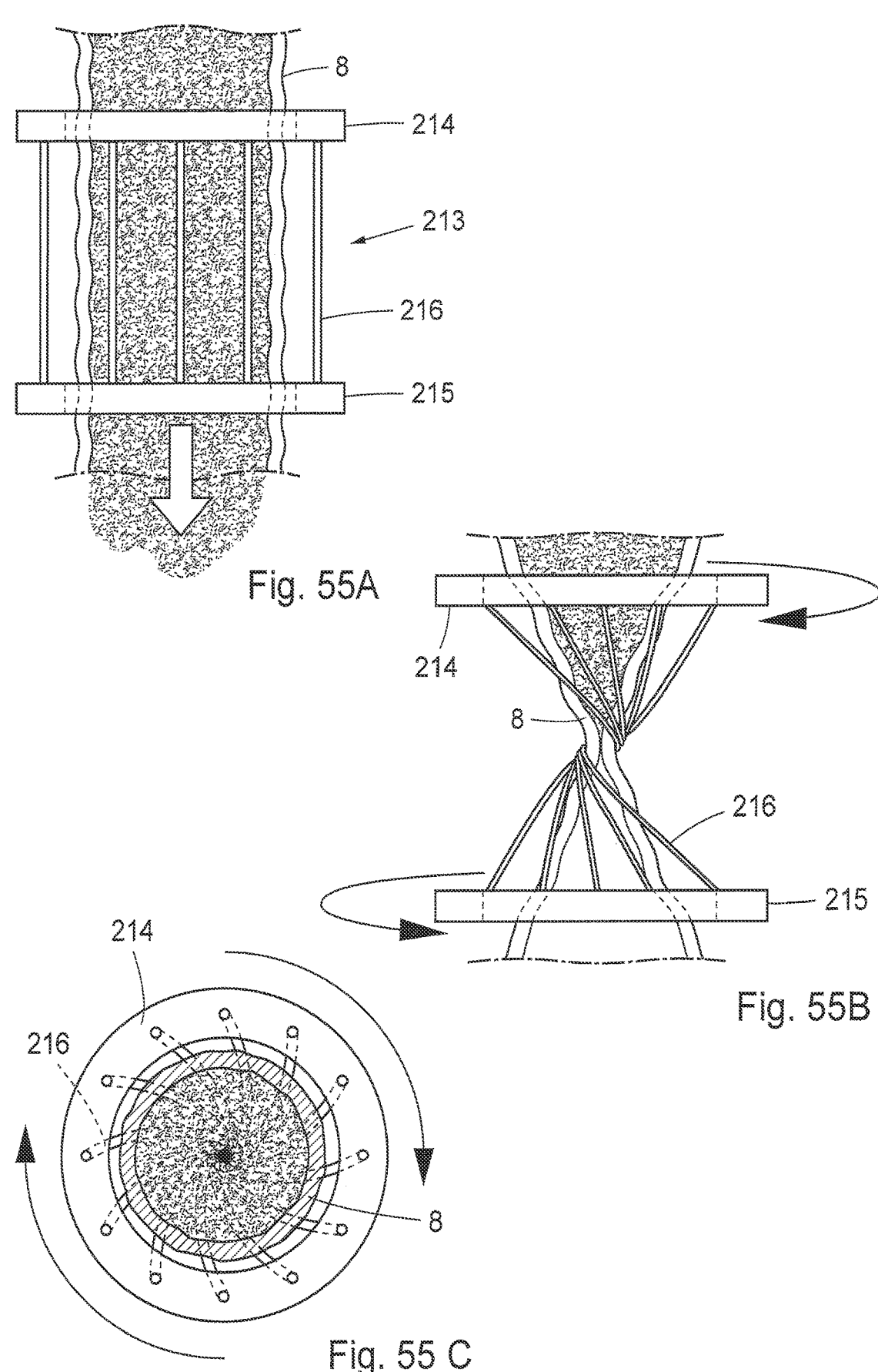
FIG. 55A is a schematic view of another mechanically operable non-inflatable constriction device for use in accordance with the invention.
FIG. 55B shows the constriction device of FIG. 55A in a constricted state.

FIGS. 55A, 55B and 55C show another mechanically operable constriction device 213 for use in the apparatus of the invention. Referring to FIG. 55A, the constriction device 213 includes a first ring-shaped holder 214 applied on a uterine tube 8 of a patient and a second ring-shaped holder 215 also applied on the uterine tube 8 spaced apart from holder 214. There are elastic strings 216 (here twelve strings) that extend in parallel along the uterine tube 8 and interconnect the two holders 213, 214 without contacting the uterine tube 8. FIG. 55A illustrate an inactivated state of the constriction device 213 in which the uterine tube 8 is not constricted.

Referring to FIGS. 55B and 55C, when the uterine tube 8 is to be constricted the ring-shaped holders 213 and 214 are rotated by an operation means (not shown) in opposite directions, whereby the elastic strings 216 constrict the uterine tube 8 in a manner that appears from FIGS. 55B and 55C. For the sake of clarity, only five strings 216 are shown in FIG. 55B.

In accordance with the present invention, electrodes for electrically stimulating the uterine tube 8 to cause contraction of the wall of the uterine tube 8 are attached to the strings 216 (not shown in FIGS. 55A-55C).

Figures 56, 57:
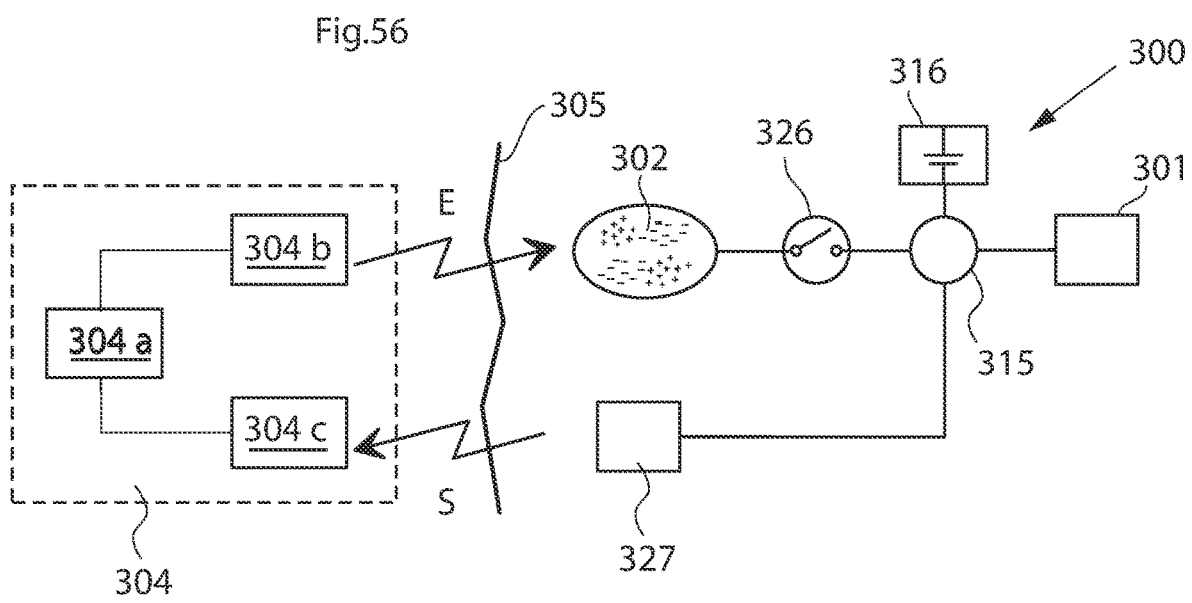
FIG. 56 is a schematic block diagram illustrating an arrangement for supplying an accurate amount of wireless energy used for the operation of the constriction/stimulation unit as described above.
FIG. 57 schematically shows an embodiment of the system, in which the apparatus is operated with wire bound energy.

FIG. 56 schematically illustrates an arrangement of the apparatus that is capable of sending information from inside the patient's body to the outside thereof to give information related to at least one functional parameter of the apparatus, and/or related to a physical parameter of the patient, in order to supply an accurate amount of energy to an implanted internal energy receiver 302 connected to energy consuming components of an implanted constriction/stimulation unit 301 of the apparatus of the invention. Such an energy receiver 302 may include a source of energy and/or an energy-transforming device. Briefly described, wireless energy is transmitted from an external source of energy 304*a* located outside the patient and is received by the internal energy receiver 302 located inside the patient. The internal energy receiver is adapted to directly or indirectly supply received energy to the energy consuming components of the constriction/stimulation unit 301 via a switch 326. An energy balance is determined between the energy received by the internal energy receiver 302 and the energy used for the constriction/stimulation unit 301, and the transmission of wireless energy is then controlled based on the determined energy balance. The energy balance thus provides an accurate indication of the correct amount of energy needed, which is sufficient to operate the constriction/stimulation unit 301 properly, but without causing undue temperature rise.

In FIG. 56 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external source of energy 304*a* provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external source of energy 304*a* and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted source of energy, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304*b* that controls the external source of energy 304*a* based on the determined energy balance to regulate the amount of transferred energy. In order to transfer the correct amount of energy, the energy balance and the required amount of energy is determined by means of a determination device including an implanted internal control unit 315 connected between the switch 326 and the constriction/stimulation unit 301. The internal control unit 315 may thus be arranged to receive various measurements obtained by suitable sensors or the like, not shown, measuring certain characteristics of the constriction/stimulation unit 301, somehow reflecting the required amount of energy needed for proper operation of the constriction/stimulation unit 301. Moreover, the current condition of the patient may also be detected by means of suitable measuring devices or sensors, in order to provide parameters reflecting the patient's condition. Hence, such characteristics and/or parameters may be related to the current state of the constriction/stimulation unit 301, such as power consumption, operational mode and temperature, as well as the patient's condition reflected by parametyers such as: body temperature, blood pressure, heartbeats and breathing. Other kinds of physical parameters of the patient and functional parameters of the device are described elsewhere.

Furthermore, a source of energy in the form of an accumulator 316 may optionally be connected to the implanted energy-transforming device 302 via the control unit 315 for accumulating received energy for later use by the constriction/stimulation unit 301. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the constriction/stimulation unit 301, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus, or the patient, or an implanted source of energy if used, or any combination thereof. The internal control unit 315 is further connected to an internal signal transmitter 327, arranged to transmit a control signal reflecting the determined required amount of energy, to an external signal receiver 304*c* connected to the external control unit 304*b*. The amount of energy transmitted from the external source of energy 304*a* may then be regulated in response to the received control signal.

Alternatively, the determination device may include the external control unit 304*b*. In this alternative, sensor measurements can be transmitted directly to the external control unit 304*b* wherein the energy balance and/or the currently required amount of energy can be determined by the external control unit 304*b*, thus integrating the above-described function of the internal control unit 315 in the external control unit 304*b*. In that case, the internal control unit 315 can be omitted and the sensor measurements are supplied directly to the internal signal transmitter 327 which sends the measurements over to the external signal receiver 304*c* and the external control unit 304*b*. The energy balance and the currently required amount of energy can then be determined by the external control unit 304b based on those sensor measurements.

Hence, the present solution according to the arrangement of FIG. 56 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted source of energy or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external source of energy 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 56 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external source of energy 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external source of energy 304a, such as voltage, current, amplitude, wave frequency and pulse characteristics. This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

With reference to FIG. 57, although wireless transfer of energy for operating the apparatus has been described above to enable non-invasive operation, it will be appreciated that the apparatus can be operated with wire bound energy as well. Such an example is shown in FIG. 57, wherein an external switch 326 is interconnected between the external source of energy 304a and an operation device, such as an electric motor 307 operating the constriction/stimulation unit 301. An external control unit 304b controls the operation of the external switch 326 to effect proper operation of the constriction/stimulation unit 301.

Figure 58:
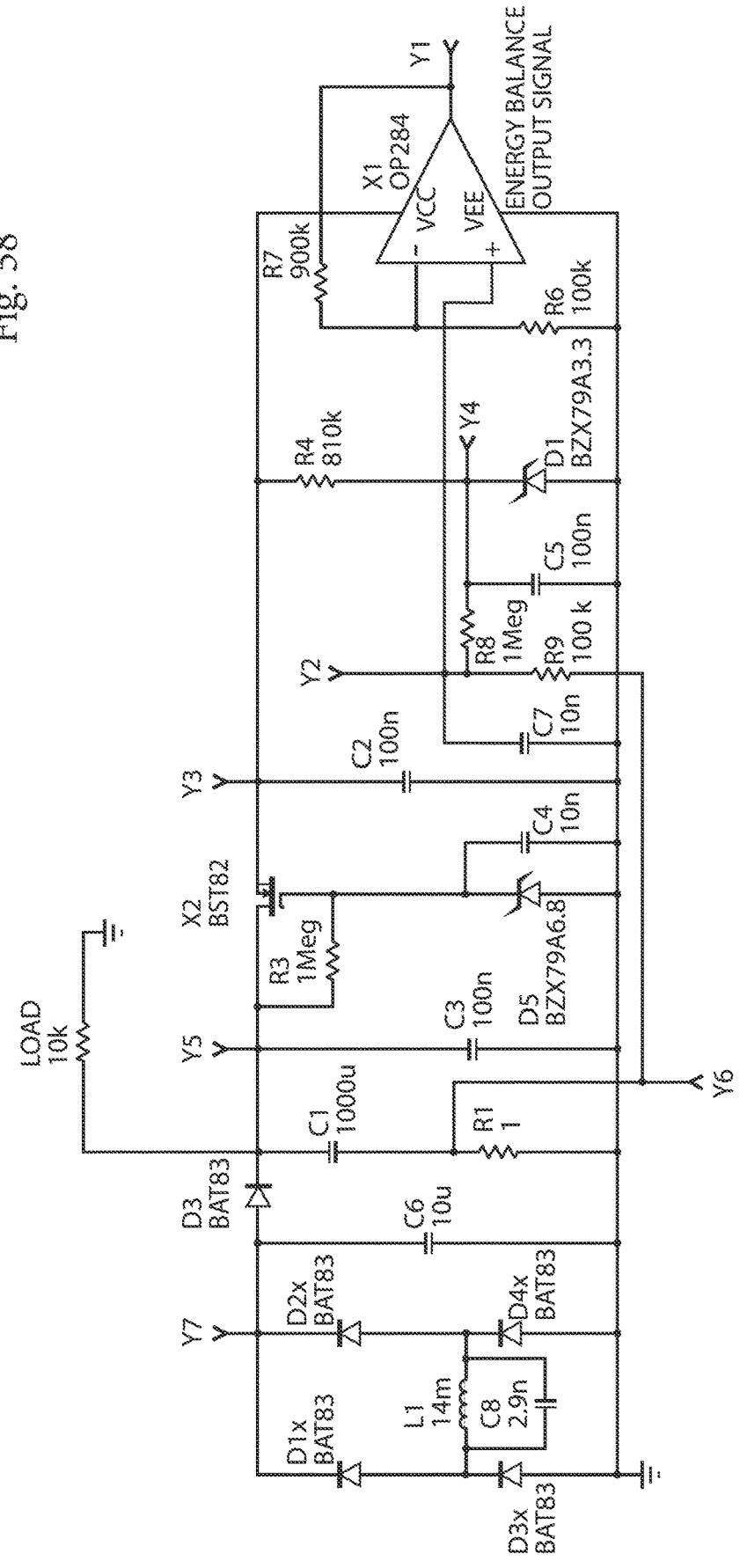
FIG. 58 is a more detailed block diagram of an arrangement for controlling the transmission of wireless energy used for the operation of the constriction/stimulation unit as described above.

FIG. 58 illustrates different embodiments for how received energy can be supplied to and used by the constriction/stimulation unit 301. Similar to the example of FIG. 56, an internal energy receiver 302 receives wireless energy E from an external source of energy 304a which is controlled by a transmission control unit 304b. The internal energy receiver 302 may comprise a constant voltage circuit, indicated as a dashed box "constant V" in FIG. 58, for supplying energy at constant voltage to the constriction/ stimulation unit 301. The internal energy receiver 302 may further comprise a constant current circuit, indicated as a dashed box "constant C" in the figure, for supplying energy at constant current to the constriction/stimulation unit 301.

The constriction/stimulation unit 301 comprises an energy consuming part 301*a*, which may be a motor, pump, restriction device, or any other medical appliance that requires energy for its electrical operation. The constriction/ stimulation unit 301 may further comprise an energy storage device 301*b* for storing energy supplied from the internal energy receiver 302. Thus, the supplied energy may be directly consumed by the energy consuming part 301*a*, or stored by the energy storage device 301*b*, or the supplied energy may be partly consumed and partly stored. The constriction/stimulation unit 301 may further comprise an energy stabilizing unit 301*c* for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the constriction/ stimulation unit 301, before being consumed and/or stored by the constriction/stimulation unit 301. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 56 and FIG. 58 illustrate some possible but non-limiting implementation options regarding how the various shown functional components and elements can be arranged and connected to each other. However, the skilled person will readily appreciate that many variations and modifications can be made within the scope of the present invention.

Figure 59:
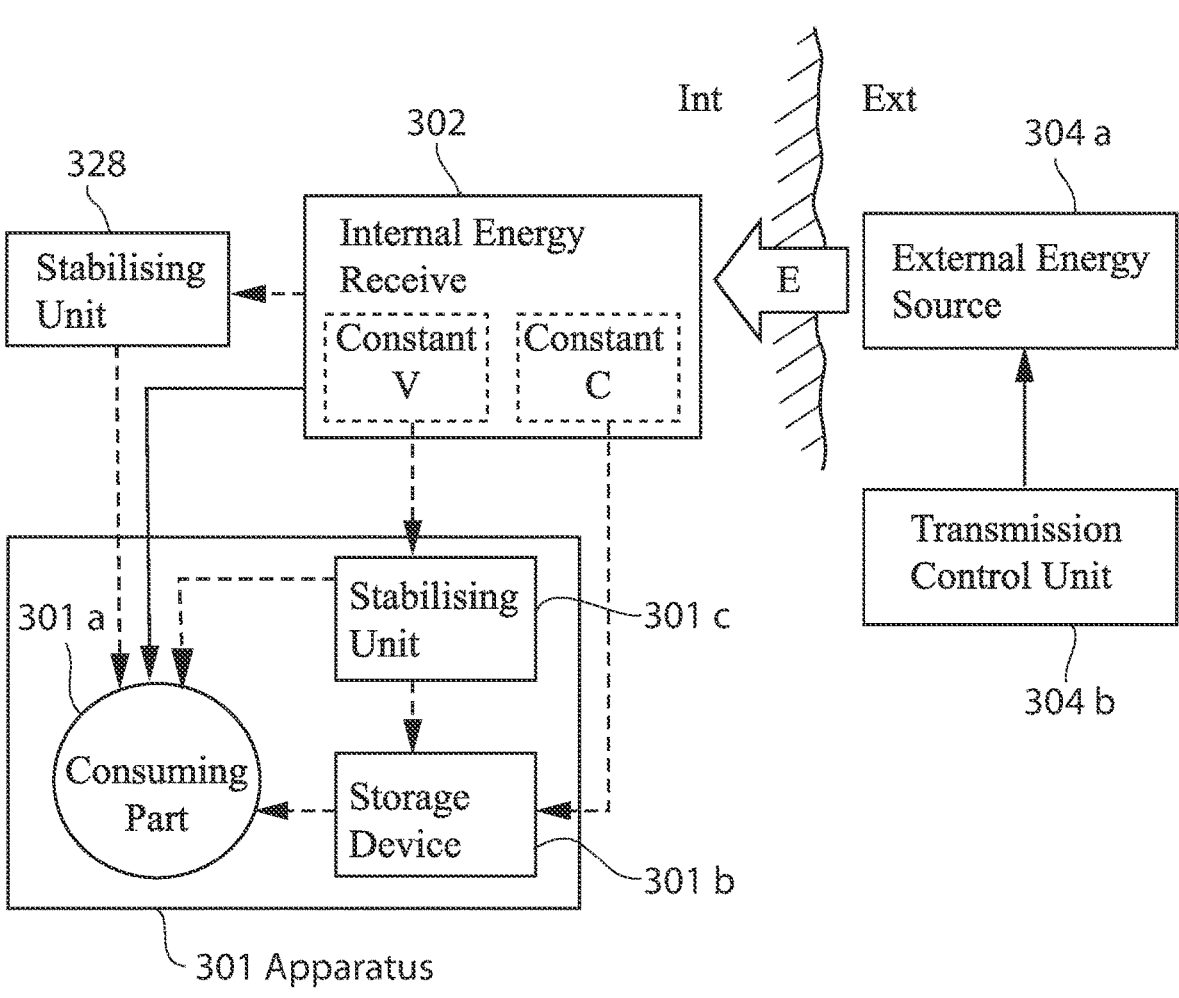
FIG. 59 is a circuit for the arrangement shown in FIG. 19, according to a possible implementation example.

FIG. 59 schematically shows an energy balance measuring circuit of one of the proposed designs of the apparatus for controlling transmission of wireless energy, or energy balance. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the source of energy. The output signal from the circuit is typically fed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 59 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 59; the transmitting parts of the system are excluded.

The implementation of the general concept of energy balance and the way the information is transmitted to the external energy transmitter can of course be implemented in numerous different ways. The schematic FIG. 20 and the above described method of evaluating and transmitting the information should only be regarded as examples of how to implement the control system.

Circuit Details

In FIG. 59 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

The embodiments described in connection with FIGS. 56, 58 and 59 identify a general method for controlling transmission of wireless energy to implanted energy consuming components of the apparatus of the present invention. Such a method will be defined in general terms in the following.

A method is thus provided for controlling transmission of wireless energy supplied to implanted energy consuming components of an apparatus as described above. The wireless energy E is transmitted from an external source of energy located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the operation of the implanted parts of the apparatus. The transmission of wireless energy E from the external source of energy is then controlled based on the determined energy balance.

The wireless energy may be transmitted inductively from a primary coil in the external source of energy to a secondary coil in the internal energy receiver. A change in the energy balance may be detected to control the transmission of wireless energy based on the detected energy balance change. A difference may also be detected between energy received by the internal energy receiver and energy used for the operation of the implanted parts of the apparatus, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the operation of the implanted parts of the apparatus be consumed to operate the implanted parts of the apparatus and/or stored in at least one implanted energy storage device of the apparatus.

When electrical and/or physical parameters of the implanted parts of the apparatus and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external source of energy may be controlled by applying to the external source of energy electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external source of energy may have a first characteristic time period or first time constant, and when effectively varying the transmitted energy, such frequency time period may be in the range of the first characteristic time period or time constant or shorter.

The embodiments described in connection with FIGS. 56, 58 and 59 also identify general features for controlling transmission of wireless energy to implanted energy consuming components of the apparatus of the present invention. Such features of the apparatus will be defined in general terms in the following.

In its broadest sense, the apparatus comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The apparatus further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the apparatus of the invention may comprise any of the following features:

A primary coil in the external source of energy adapted to transmit the wireless energy inductively to a secondary coil in the internal energy receiver.

The determination device is adapted to detect a change in the energy balance, and the control device controls the transmission of wireless energy based on the detected energy balance change.

The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for implanted parts of the apparatus is consumed to operate the implanted parts, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

A contriction device can be arranged to delay the movement of the sperms towards the egg for a predetermined amount of time in order to avoid pregnancy. This can be acheived in many different ways, of which two will be described below.

Figures 60, 61A, 61B, 61C:
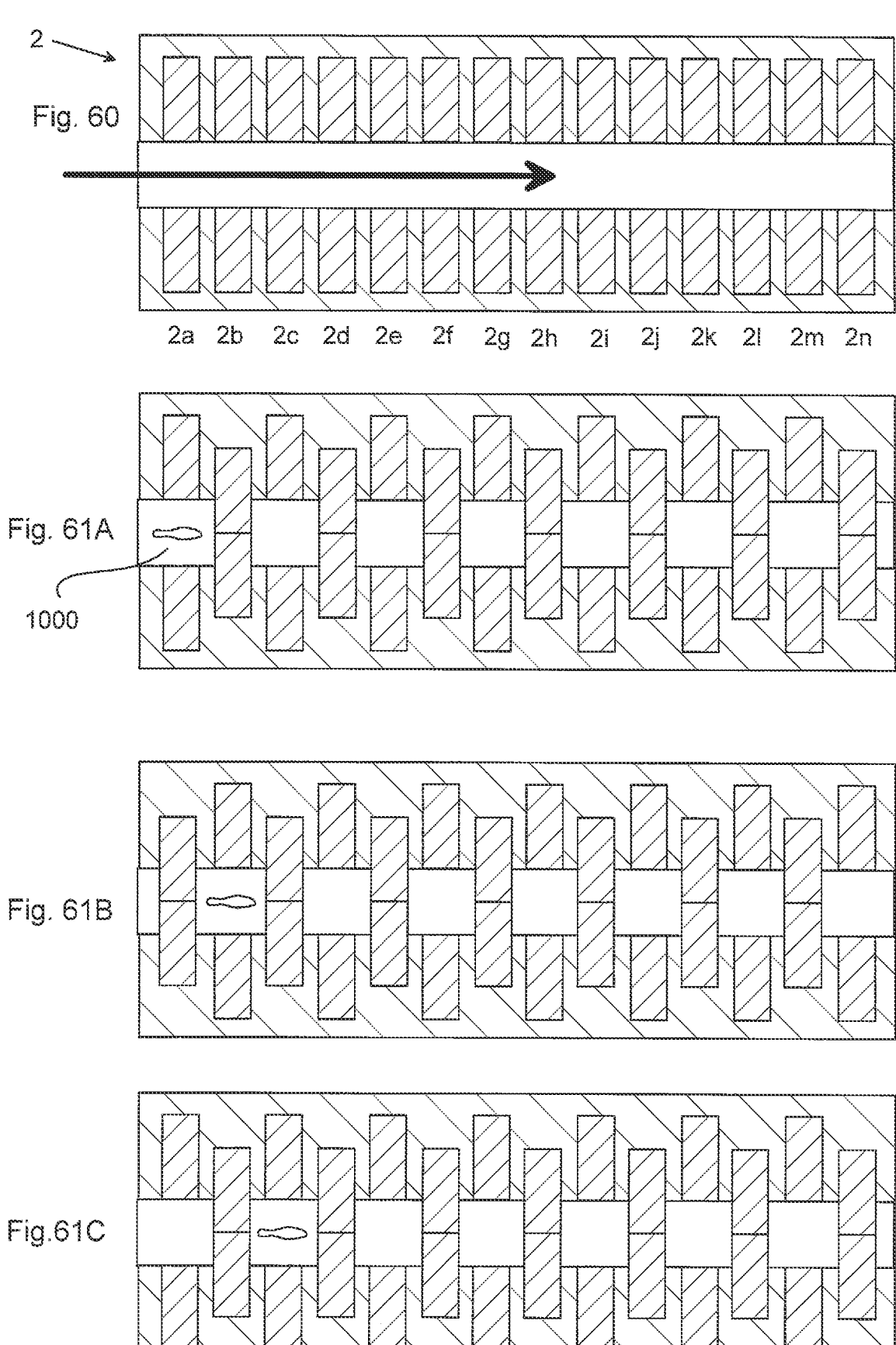
FIG. 60 is a sectional view through a constriction device adapted to restrict or stop the flow through an uterine tube.
FIG. 61A illustrates the constriction device of FIG. 60 in a first interrupting stage
FIG. 61B illustrates the constriction device of FIG. 60 in a second interrupting stage.
FIG. 61C illustrates the constriction device of FIG. 60 in a third interrupting stage.

FIG. 60 is a sectional view through a constriction device 2 adapted to restrict or stop the flow through an uterine tube. The general flow direction is illustrated by an arrow. The constriction device comprises an array of constriction elements 2a-2m, each arranged to restrict or close a part of the uterine tube. The constriction device illustrated in FIG. 56 is in an open or non-operative position wherein the flow is uninterrupted FIG. 61A illustrates the constriction device of FIG. 60 in a first interrupting stage, wherein every other constriction element is in a closed position. A sperm, generally designated 1000, is allowed to enter the space formed by the first, non-closed constriction element. It is stopped there by the second constriction element, which is in a closed position. This operative state can remain for a desired period of time, such as one day.

FIG. 61B illustrates the constriction device of FIG. 60 in a second interrupting stage, wherein every constriction element that was closed in the first interrupting stage is in an open position and vice versa. The sperm is then allowed to enter the space formed by the second, non-closed constriction element. It is stopped there by the third constriction element, which is in a closed position. This operative state can remain for a desired period of time, such as one day.

FIG. 61A illustrates the constriction device of FIG. 60 in a third interrupting stage, wherein every other constriction element is in a closed position, exactly as in the first interrupting stage. The sperm shown in FIGS. 61A and 61B, is allowed to enter the space formed by the third, non-closed constriction element. It is stopped there by the fourth constriction element, which is in a closed position. This operative state can remain for a desired period of time, such as one day.

Repeating this process, the movement of a sperm can be delayed for a desired period of time until it reaches the other end of the constriction device. Since the life of a sperm is less than about five days, delaying a sperm in this way will ensure that it does not reach an egg in the uterine tube and thereby the constriction device functions to prevent undesired pregnancy. By altering the constricted area of the uterine tube, this will not be harmed like if the same area were constricted for a longer period of time.

FIGS. 62A-D show a second embodiment of a constriction device. This operates in a way similar to the first embodiment of a constriction device shown in FIGS. 61A-C. However, in this embodiment, two consecutive constriction elements are in an open position at a time when allowing progress of the sperm.

It will thus be realized that the above described control of sperms in the uterine tube is also applicable to eggs moving through a uterine tube.

What is claimed is:
1. An apparatus for controlling flow of sperms in a uterine tube of a female patient, the apparatus comprising:
an implantable constriction device comprising at least one constriction element for constricting at least one wall portion of the uterine tube,
an internal source of energy for supplying energy to the operation of the constriction device, and a control device for controlling the constriction device to constrict the at least one wall portion of the uterine tube with a force delivered by the at least one constriction element to the at least one wall portion to thereby at least restrict the flow of sperms in the uterine tube.
2. The apparatus according to claim 1, wherein the control device is configured to calibrate the constriction device by controlling the constriction device to adjust the force of constriction of the wall portion until a desired restriction of the flow in the uterine tube is obtained.
3. The apparatus according to claim 1, wherein the constriction device is adapted to constrict the wall portion to substantially stop the flow in the uterine tube while the blood circulation in the constricted wall portion is substantially unrestricted.

4. The apparatus according to claim 1, further comprising a sensor for sensing at least one of a physical parameter of the patient and a functional parameter of the apparatus, wherein the control device is configured to control the constriction device to adjust the force of constriction of the wall portion in response to the sensed parameter of the patient or apparatus.

5. The apparatus according to claim 4, wherein the physical parameter is at least one of motility of sperm or a pressure in the patient's body.

6. The apparatus according to claim 4, further comprising a transmitter for sending feedback information from inside the patient's body to the outside thereof, the feedback information being related to at least one of the physical parameter of the patient and the functional parameter of the apparatus.

7. The apparatus according to claim 4, wherein the control device is configured to control the constriction device to increase the force of constriction of the wall portion in response to a sensed pressure increase in the uterine tube, such that the flow in the uterine tube remains stopped when a pressure increase occurs.

8. The apparatus according to claim 1, wherein the control device is configured to control the constriction device to change the force delivered by the at least one constriction element to the wall portion in response to the sensor sensing a predetermined threshold value of the physical parameter or functional parameter in the uterine tube.

9. The apparatus according to claim 1, wherein the control device comprises a wireless remote control for wirelessly controlling the constriction device from outside the patient's body.

10. The apparatus according to claim 1, wherein the constriction device comprises a plurality of constriction elements, each of which is positioned along a series of wall portions of the uterine tube to enable successively constriction of the wall portions of the series of wall portions of the uterine tube.

11. The apparatus according to claim 10, wherein the control device is configured to control the plurality of constriction elements to intermittently and individually constrict different portions of the wall portions, such that at least two wall portions are constricted at different points of time.

12. The apparatus according to claim 10, wherein the control device is configured to control the plurality of constriction elements to intermittently constrict each of the different wall portions during successive time periods, each time period being short enough to maintain over time satisfactory blood circulation in each respective wall portion until the lapse of the time period.

13. The apparatus according to claim 10, wherein the control device is configured to control the plurality of constriction elements to intermittently constrict the wall portions, such that a wall portion that currently is not constricted has time to restore substantially normal blood circulation before the corresponding constriction element constricts the wall portion again.

14. The apparatus according to claim 10, wherein the control device is configured to control the plurality of constriction elements to cyclically propagate the constriction of the wall portions along the patient's uterine tube in the same or opposite direction of the flow in the patient's uterine tube.

15. The apparatus according to claim 10, wherein the control device is configured to control the plurality of constriction elements to cyclically vary the force delivered to the different wall portions.

16. The apparatus according to claim 10, wherein the plurality of constriction elements comprises a first constriction element for constricting the wall portion of the uterine tube at an upstream end thereof, a second constriction element for constricting the wall portion at a downstream end thereof, and a third constriction element for constricting the wall portion between the upstream and downstream ends thereof, and the control device is configured to control the first, second and third constriction elements to constrict and release the wall portions independently of one another.

17. The apparatus according to claim 1, further comprising an operation device comprising a reservoir having an adjustable internal volume comprising a hydraulic fluid therein, and a motor being connected to the reservoir, wherein the control device is configured to control the motor to adjust the internal volume of the reservoir for hydraulically operating the constriction device.

18. The apparatus according to claim 17, wherein at least one constriction element of the apparatus comprises an expandable cavity in fluid connection with the reservoir and wherein a volume of the cavity is adjustable by movement of hydraulic fluid between the cavity and the reservoir.

19. The apparatus according to claim 1, wherein the control device comprises a manually operable switch for switching on and off the constriction device, the switch being adapted for subcutaneous implantation in the patient to be manually operated from outside the patient's body.

20. The apparatus according to claim 1, wherein the source of energy is one of a primary battery and a rechargeable battery.

* * * * *